(12) United States Patent
Gormley et al.

(10) Patent No.: US 11,970,695 B2
(45) Date of Patent: Apr. 30, 2024

(54) SAMPLE PREPARATION ON A SOLID SUPPORT

(71) Applicant: Illumina Cambridge Limited, Cambridge (GB)

(72) Inventors: Niall Gormley, Cambridge (GB); Geoffrey Paul Smith, Cambridge (GB)

(73) Assignee: Illumina Cambridge Limited, Cambridge (GB)

( * ) Notice: Subject to any disclaimer, the term of this patent is extended or adjusted under 35 U.S.C. 154(b) by 248 days.

(21) Appl. No.: 17/197,852

(22) Filed: Mar. 10, 2021

(65) Prior Publication Data

US 2021/0222157 A1 Jul. 22, 2021

Related U.S. Application Data

(63) Continuation of application No. 16/027,052, filed on Jul. 3, 2018, now Pat. No. 10,988,760, which is a (Continued)

(51) Int. Cl.
| | |
|---|---|
| *C12N 15/10* | (2006.01) |
| *B01J 19/00* | (2006.01) |
| *C12Q 1/6834* | (2018.01) |
| *C12Q 1/6869* | (2018.01) |
| *C12Q 1/6874* | (2018.01) |

(Continued)

(52) U.S. Cl.
CPC ...... *C12N 15/1065* (2013.01); *B01J 19/0046* (2013.01); *C12N 15/1093* (2013.01); *C12Q 1/6834* (2013.01); *C12Q 1/6869* (2013.01); *C12Q 1/6874* (2013.01); *B01J 2219/00286* (2013.01); *B01J 2219/00608* (2013.01); *B01J 2219/00722* (2013.01); *C40B 40/08* (2013.01); *C40B 50/14* (2013.01); *C40B 50/18* (2013.01)

(58) Field of Classification Search
None
See application file for complete search history.

(56) References Cited

U.S. PATENT DOCUMENTS

| | | | |
|---|---|---|---|
| 5,130,238 | A | 7/1992 | Malek et al. |
| 5,185,243 | A | 2/1993 | Ullman et al. |
| (Continued) | | | |

FOREIGN PATENT DOCUMENTS

| | | | |
|---|---|---|---|
| CN | 102264914 | A | 11/2011 |
| CN | 103443338 | A | 12/2013 |
| (Continued) | | | |

OTHER PUBLICATIONS

Van Berkum et al., "Hi-C: A method to study the three-dimensional architecture of genomes," J Vis Exp. 2010, 39, 1869.
(Continued)

*Primary Examiner* — Kaijiang Zhang
(74) *Attorney, Agent, or Firm* — McNeill Baur PLLC

(57) ABSTRACT

Presented are methods and compositions for using immobilized transposase and a transposon end for generating an immobilized library of 5'-tagged double-stranded target DNA on a surface. The methods are useful for generating 5'- and 3'-tagged DNA fragments for use in a variety of processes, including massively parallel DNA sequencing.

11 Claims, 25 Drawing Sheets

Related U.S. Application Data continuation of application No. 14/671,071, filed on Mar. 27, 2015, now Pat. No. 10,041,066, which is a continuation of application No. 13/790,220, filed on Mar. 8, 2013, now Pat. No. 9,683,230.

(60) Provisional application No. 61/750,682, filed on Jan. 9, 2013.

(51) Int. Cl.
  *C40B 40/08* (2006.01)
  *C40B 50/14* (2006.01)
  *C40B 50/18* (2006.01)

(56) References Cited

U.S. PATENT DOCUMENTS

| | | |
|---|---|---|
| 5,223,414 A | 6/1993 | Zarling et al. |
| 5,455,166 A | 10/1995 | Walker |
| 5,573,907 A | 11/1996 | Carrino et al. |
| 5,599,675 A | 2/1997 | Brenner |
| 5,641,658 A | 6/1997 | Adams et al. |
| 5,679,524 A | 10/1997 | Nikiforov et al. |
| 5,750,341 A | 5/1998 | Macevicz |
| 5,858,671 A | 1/1999 | Jones |
| 5,965,443 A | 10/1999 | Reznikoff et al. |
| 6,210,891 B1 | 4/2001 | Nyren et al. |
| 6,214,587 B1 | 4/2001 | Dattagupta et al. |
| 6,258,568 B1 | 7/2001 | Nyren |
| 6,261,782 B1 | 7/2001 | Lizardi et al. |
| 6,274,320 B1 | 8/2001 | Rothberg et al. |
| 6,355,431 B1 | 3/2002 | Chee et al. |
| 6,383,754 B1 | 5/2002 | Kaufman et al. |
| 6,437,109 B1 | 8/2002 | Reznikoff et al. |
| 6,480,791 B1 | 11/2002 | Strathmann |
| 6,593,113 B1 | 7/2003 | Tenkanen et al. |
| 6,777,187 B2 | 8/2004 | Makarov et al. |
| 6,828,098 B2 | 12/2004 | Langmore et al. |
| 6,846,658 B1 | 1/2005 | Vaisvila et al. |
| 7,001,792 B2 | 2/2006 | Sauer et al. |
| 7,057,026 B2 | 6/2006 | Barnes et al. |
| 7,115,400 B1 | 10/2006 | Adessi et al. |
| 7,138,267 B1 | 11/2006 | Jendrisak et al. |
| 7,211,414 B2 | 5/2007 | Hardin et al. |
| 7,244,559 B2 | 7/2007 | Rothberg et al. |
| 7,315,019 B2 | 1/2008 | Turner et al. |
| 7,329,492 B2 | 2/2008 | Hardin et al. |
| 7,399,590 B2 | 7/2008 | Piepenburg et al. |
| 7,405,281 B2 | 7/2008 | Xu et al. |
| 7,537,897 B2 | 5/2009 | Brenner et al. |
| 7,582,420 B2 | 9/2009 | Oliphant et al. |
| 7,595,883 B1 | 9/2009 | Gamal et al. |
| 7,611,869 B2 | 11/2009 | Fan |
| 7,670,810 B2 | 3/2010 | Gunderson et al. |
| 7,741,463 B2 | 6/2010 | Gormley et al. |
| 8,003,354 B2 | 8/2011 | Shen et al. |
| 8,383,345 B2 | 2/2013 | Shendure et al. |
| 8,563,477 B2 | 10/2013 | Smith et al. |
| 8,829,171 B2 | 9/2014 | Steemers et al. |
| 9,074,251 B2 | 7/2015 | Steemers et al. |
| 9,644,198 B2 | 5/2017 | Walder et al. |
| 9,644,199 B2 | 5/2017 | Belyaev |
| 10,246,746 B2 | 4/2019 | Fisher et al. |
| 10,550,426 B2 | 2/2020 | Yotani et al. |
| 11,299,730 B2 | 4/2022 | Shendure et al. |
| 2001/0046669 A1 | 11/2001 | McCobmie et al. |
| 2002/0055100 A1 | 5/2002 | Kawashima et al. |
| 2004/0002090 A1 | 1/2004 | Mayer et al. |
| 2004/0096853 A1 | 5/2004 | Mayer |
| 2004/0110191 A1 | 6/2004 | Winkler et al. |
| 2004/0259229 A1 | 12/2004 | Thevelein et al. |
| 2005/0100932 A1 | 5/2005 | Lapidus et al. |
| 2005/0191698 A1 | 9/2005 | Chee et al. |
| 2006/0024681 A1 | 2/2006 | Smith et al. |
| 2006/0040297 A1 | 2/2006 | Leamon et al. |
| 2006/0216309 A1 | 9/2006 | Holden |
| 2006/0236413 A1 | 10/2006 | Ivics et al. |
| 2006/0257905 A1 | 11/2006 | Freije et al. |
| 2006/0292611 A1 | 12/2006 | Berka et al. |
| 2007/0128610 A1 | 6/2007 | Buzby |
| 2007/0128624 A1 | 6/2007 | Gormley et al. |
| 2008/0009420 A1 | 1/2008 | Schroth et al. |
| 2008/0108082 A1 | 5/2008 | Rank et al. |
| 2008/0234136 A1 | 9/2008 | Drmanac et al. |
| 2008/0242560 A1 | 10/2008 | Gunderson et al. |
| 2009/0026082 A1 | 1/2009 | Rothberg et al. |
| 2009/0032401 A1 | 2/2009 | Ronaghi et al. |
| 2009/0047680 A1 | 2/2009 | Lok |
| 2009/0127589 A1 | 5/2009 | Rothberg et al. |
| 2009/0176234 A1 | 7/2009 | Drmanac et al. |
| 2009/0298075 A1 | 12/2009 | Travers et al. |
| 2010/0009871 A1 | 1/2010 | Reed et al. |
| 2010/0022403 A1 | 1/2010 | Kum et al. |
| 2010/0069263 A1 | 3/2010 | Shendure et al. |
| 2010/0111768 A1 | 5/2010 | Banerjee et al. |
| 2010/0120098 A1 | 5/2010 | Grunenwald et al. |
| 2010/0137143 A1 | 6/2010 | Rothberg et al. |
| 2010/0222238 A1 | 9/2010 | Smith et al. |
| 2010/0282617 A1 | 11/2010 | Rothberg et al. |
| 2011/0014657 A1 | 1/2011 | Rigatti et al. |
| 2011/0059865 A1 | 3/2011 | Smith et al. |
| 2011/0124518 A1 | 5/2011 | Cantor |
| 2011/0311506 A1 | 12/2011 | Craig |
| 2012/0053063 A1 | 3/2012 | Rigatti et al. |
| 2012/0065081 A1 | 3/2012 | Chee |
| 2012/0129704 A1 | 5/2012 | Gunderson et al. |
| 2012/0208705 A1 | 8/2012 | Steemers et al. |
| 2012/0208724 A1 | 8/2012 | Steemers et al. |
| 2012/0270305 A1 | 10/2012 | Reed et al. |
| 2013/0005585 A1 | 1/2013 | Anderson et al. |
| 2013/0017978 A1 | 1/2013 | Kavanagh et al. |
| 2013/0203605 A1 | 8/2013 | Shendure et al. |
| 2013/0323732 A1 | 12/2013 | Anderson et al. |
| 2013/0338042 A1 | 12/2013 | Shen et al. |
| 2014/0079923 A1 | 3/2014 | George et al. |
| 2014/0093916 A1 | 4/2014 | Belyaev |
| 2014/0194324 A1 | 7/2014 | Gormley et al. |
| 2015/0284714 A1 | 10/2015 | Gormley et al. |
| 2016/0138097 A1 | 5/2016 | Yotani et al. |
| 2019/0276821 A1 | 9/2019 | Steemers et al. |
| 2019/0309360 A1 | 10/2019 | Fisher et al. |

FOREIGN PATENT DOCUMENTS

| | | |
|---|---|---|
| EP | 0320308 A3 | 6/1990 |
| EP | 0439182 A2 | 7/1991 |
| EP | 0336731 B1 | 5/1994 |
| EP | 2635679 A1 | 9/2013 |
| EP | 2712931 A1 | 4/2014 |
| EP | 2670894 A4 | 10/2014 |
| JP | 2012506704 A | 3/2012 |
| JP | 2014506788 A | 3/2014 |
| JP | 2013150611 A1 | 10/2015 |
| JP | 2016508715 A | 3/2016 |
| WO | 8909835 A1 | 10/1989 |
| WO | 8910977 A1 | 11/1989 |
| WO | 8912696 A1 | 12/1989 |
| WO | 9001069 A1 | 2/1990 |
| WO | 1991006678 A1 | 5/1991 |
| WO | 9523875 A1 | 9/1995 |
| WO | 1998044151 A1 | 10/1998 |
| WO | 2004042078 A1 | 5/2004 |
| WO | 2004018497 A3 | 6/2004 |
| WO | 2005065814 A1 | 7/2005 |
| WO | 2005100585 A2 | 10/2005 |
| WO | 2006047183 A2 | 5/2006 |
| WO | 2008087040 A2 | 7/2008 |
| WO | 2007098279 A3 | 9/2008 |
| WO | 2007123744 A3 | 11/2008 |
| WO | 2010048605 A1 | 4/2010 |
| WO | 2010002883 A3 | 10/2010 |
| WO | 2011106314 A2 | 9/2011 |
| WO | 2012025250 A1 | 3/2012 |
| WO | 2012027572 A2 | 3/2012 |

(56) References Cited

FOREIGN PATENT DOCUMENTS

| WO | 2012058096 | A1 | | 5/2012 | |
|---|---|---|---|---|---|
| WO | 2012061832 | A1 | | 5/2012 | |
| WO | 2012103545 | A1 | | 8/2012 | |
| WO | 2012106546 | A2 | | 8/2012 | |
| WO | 2012108864 | A1 | | 8/2012 | |
| WO | WO-2012106546 | A2 | * | 8/2012 | ......... C12N 15/1093 |
| WO | 2013131962 | A1 | | 9/2013 | |
| WO | 2013177220 | A1 | | 11/2013 | |
| WO | 2013184796 | A1 | | 12/2013 | |
| WO | 2014124338 | A1 | | 8/2014 | |
| WO | 2014108810 | | | 9/2014 | |
| WO | 2014142850 | A1 | | 9/2014 | |
| WO | 2014189957 | A2 | | 11/2014 | |

OTHER PUBLICATIONS

Vincent et al., "Helicase-dependent isothermal DNA amplification", EMBO Reports 2004, 5(8), 795-800.
Voordouw et al., "Studies on Co!El-plasmid DNA and its interactions with histones; sedimentation velocity studies of monodisperse complexes reconstituted with calf-thymus histones," Nucleic Acids Research, 1977, 4(5), 1207-1223.
Walker et al., "A Chemiluminescent DNA Probe Test Based on Strand Displacement Amplification", Molecular Methods for Vims Detection, 1995, Academic Press Inc. Ch 15, pp. 329-349, 1995.
Walker et al., "Strand displacement amplification—an isothermal, in vitro DNA amplification technique", Nucleic Acids Res. 1992, 20(7), 1691-1696.
Wang et al., "Calling Cards enable multiplexed identification of genomic targets of DNA-binding proteins," Genome Research 2011, 21(5), 748-755.
Waterston et al., "Initial sequencing and comparative analysis of the mouse genome," Nature, 420(6915), 2002, 520-62.
Waterston et al., "More on the sequencing of the human genome," Proc. Natl. Acad. Sci. USA 2003, 100(6), 3022-3024.
Waterston et al., "On the sequencing of the human genome," Proc Natl Acad Sci USA. 99(6), 2002, 3712-6.
Wilson et al., "New transposon delivery plasmids for insertional mutagenesis in Bacillus anthracis", Journal of Microbiological Methods, 71, 2007, 332-335.
Wold et al., "Sequence Census Methods for Functional Genomics", Nature Methods, 5(1 ), 2008, 19-21.
Wong et al., "ChiP'ing the mammalian genome: technical advances and insights into functional elements," Genome Med 2009, 1, 89.
Xu, "Extracting Haplotypes from Diploid Organisms," Current Issues in Molecular Biology, vol. 8, Jul. 2006, 113-122.
Zee et al., "Increasing cloning possibilities using artificial zinc finger nucleases," Proceedings of the National Academy of Sciences, USA, vol. 105, Nov. 35, 2008, 12785-12790.
Zeng et al., "High-performance single cell genetic analysis using microfluidic emulsion generator arrays.," Anal Chem. 32 (8), 2010, 3183-90.
Zerbino et al., "Velvet: Algorithms for De Novo Short Read Assembly Using de Bruijn Graphs", Genome Research, 18(5), 2008, 821-829.
Zhang et al., "A Novel Mechanism of Transposon-Mediated Gene Activation", PLOS Genetics el000689. Epub Oct. 16, 2009.
Zhou et al., "A Single Molecule Scaffold for the Maize Genome," PLOS Genet 2009, 5(11), el000711.
Zhou et al., "Molecular genetic analysis of transposase-end DNA sequence recognition: Cooperativity of three adjacent base-pairs in specific interaction with a mutant Tn5 transposase," Journal of Molecular Biology, vol. 276, 1998, 913-925.
Zhou et al., "Validation of rice genome sequence by optical mapping," BMC Genomics 8(1), 2007, 278.
Zilberman et al., "Genome-wide analysis of DNA methylation patterns.," Development 134(22), 2007, 3959-3965.
McCloskey et al., "Encoding PCR Products with Batch-stamps and Barcodes," Biochem Genet 45:761, 2007, 761-767.

Meissner et al., "Reduced representation bisulfite sequencing for comparative high-resolution DNA methylation analysis," Nucleic Acids Research, 33, 2005, 5868-5877.
Miner et al., "Molecular barcodes detect redundancy and contamination in hairpin-bisulfite PCR," Nucleic Acids Research, 2004, vol. 32, No. 17, el35, 4 pages.
Mitra et al., "Fluorescent in situ sequencing on polymerase colonies," Analytical Biochemistry—320 (2003) 55-65, 2003, 55-65.
Mizuuchi, "In vitro transposition of bacteriophase Mu: a biochemical approach to a novel replication reaction", Cell, 35, 1983, 785-94.
Mizuuchi, "Transpositional Recombination: Mechanistic Insights from Studies of Mu and Other Elements", Annu. Rev. Biochem. 61, 1992, 1011-51.
Mortaza Vi et al., "Mapping and quantifying mammalian transcriptomes by RNA-seq," Nature Methods, 5(7), 2008, 621-8.
Nextera™ DNA Sample Prep Kits, printed on Feb. 13, 2012, 1 pg., http://www.epibio.com/nextera.
Ng et al., "Targeted capture and massively parallel sequencing of 12 human exomes," Nature 461 (7261), 2009, 272-6.
Numan et al., "Mutation discovery by targeted genomic enrichment of multiplexed barcoded samples," Nature Methods, vol. 7, No. 11, 2010, 913-915.
Oh et al., "A Robust Platform for High-Throughput Genomics in Microorganisms," A dissertation submitted to the department of genetics and the committee on graduate studies of Stanford University in partial fulfillment of the requirements for the degree of doctor of philosophy, Mar. 2010, i, ii and 10-30.
Oh et al., "A universal TagModule collection for parallel genetic analysis of microorganisms," Nucleic Acids Research, vol. 38, No. 14, May 21, 2010, 146.
Ohtsubo et al., "Bacterial insertion sequences", Curr. Top. Microbial. Immunol. 204, 1996, 1-26.
Old et al., "Recognition sequence of restriction endonuclease III from Hemophilus influenzae," J. Mo !. Biol. 1975, 331-339.
Ooka et al., "Inference of the impact of insertion sequence (IS) elements on bacterial genome diversification through analysis of small-size structural polymorphisms in Escherichia coli 0157 genomes," Genome Research, vol. 19, 2009, 1809-1816.
Oroskar et al., "Detection of immobilized amplicons by ELISA-like techniques", Clinical Chemistry 42, 1996, 1547-1555.
Parkinson et al., "Preparation of high-quality next-generation sequencing libraries from pico gram quantities of target DNA," Genome Res. 2012, 22(1), 125-133.
Paul et al., "Single-molecule dilution and multiple displacement amplification for molecular haplotyping," BioTechniques 38, Apr. 2005, 553-559.
Peck et al., "A method for high-throughput gene expression signature analysis," Genome Biology 7.7 (2006) R61.
Plasterk, "The Tel/mariner transposon family", Curr Top Micro biol Immunol, 204, 1996, 125-43.
Pobigaylo et al., "Construction of a large signature-tagged min0Tn5 transposon library and its application to mutagenesis of Sinorhizobium meliloti," Applied and Environmental Microbiology, vol. 72, No. 6, Jun. 2006, 4329-4337.
Ramanathan et al., "An integrative approach for the optical sequencing of single DNA molecules," Analytical Biochemistry, vol. 330, No. 2, 2004, 227-241.
Raymond et al., "Targeted, haplotype-resolved resequencing of long segments of the human genome," Genomics 86 (2005) 759-766.
Reinhardt et al., "De Novo Syringae pv. Assembly Oryzae", Using Genome Low-Coverage Research Short 2009, Read 19(2), Sequence 294-305. Data from the Rice Pathogen Pseudomonas syringae pv. Oryzae, Genome Research 2009, 19(2), 294-305.
Riehn et al., "Restriction mapping in nanofluidic devices.," Proceedings of the National Academy of Sciences of the United States of America 102(29): 2005, 10012-10016.
Ritz et al., "Structural variation analysis with strobe reads," Bioinformatics, 26(10), 2010, 1291-8.
Rode et al., "New tools for integrated genetic and physical analyses of the Escherichia coli chromosome," Gene 1995, 1-9.
Ronaghi et al., "A Sequencing Method Based on Real-Time Phyrophosphate", Science 1998, 281 (5375):363-365.

(56) References Cited

OTHER PUBLICATIONS

Ronaghi et al., "Real-time DNA sequencing using detection of pyrophosphate release", Anal. Biochem. 1996, 242 (!), 84-89.
Ronaghi, "Pyrosequencing sheds light on DNA sequencing", Genome Res, 11(1), 2001, 3-11.
Savilahti et al., "The Phage Mu transpososome core: DNA requirements for assembly and function," EMBO J., 14, 1995, 4893-4903.
Schatz et al., "Assembly of large genomes using second-generation sequencing," Genome Res. 2010, 20(9), 1165-1173.
Schwartz et al., "Catpuring native long-range contiguity by in situ library construction and optical sequencing," Proc. Natl. Acad. Sci. USA 2012, 109(46), 18749-1875.
Schwartz et al., "Ordered restriction maps of *Saccharomyces cerevisiae* chromosomes constructed by optical mapping," Science 262 (5130), 1993, 110-4.
Seong et al., "Measurement of Enzyme Kinetics Using a Continuous-Flow Microfluidic System," Anal. Chem., 2003, 75 (13), pp. 3161-3167.
Shendure et al., "Accurate Multiplex Polony Sequencing of an Evolved Bacterial Genome," Science, vol. 309, Sep. 9, 2005, 1728-1732.
Shendure et al., "Advanced sequencing technologies: methods and goals," Nature Rev. Genet., 5, 2004, 335-344.
Shendure et al., "Next-generation DNA sequencing," Nature Biotechnology 26(10), 2008, 1135-1145.
Shevchenko et al., "Systematic sequencing of cDNA clones using the transposon Tn5," Nucleic Acids Res. 30, 2002, 2469-2477.
Simon et al., "Short-Read Sequencing Technologies for Transcriptional Analysis," Annual review of plant biology 60 (2009): 305-333.
Sipos et al., "An Improved Protocol for Sequencing of Repetitive Genomic Regions and Structural Variations Using Mutagenesis and Next Generation Sequencing," PLOS One 7(8), published online doi:10.1371/journal.pone.0043359, Aug. 17, 2012, e43359.
Smith et al., "Direct Mechanical Measurements of the Elasticity of Single DNA Molecules by Using Magnetic Beads", Science, 258, 1992, p. 1122.
Soni et al., "Progress toward Ultrafast DNA Sequencing Using Solid-State Nanopores", Clin Chem, 53(11), 2007, 1996-2001.
Sorber et al., "The Long March: A Sample Preparation Technique That Enhances Contig Length and Coverage by High-Throughput Short-Read Sequencing", PLoS ONE 2(10):e3495, Oct. 2008, 9 pages.
Steensel et al., "Genomics tools for unraveling chromosome architecture," Nature Biotechnology, Oct. 13, 2010.
Strahl et al., "The language of covalent histone modifications," Nature 2000, vol. 403, pp. 41-45.
Syed et al., "Optimized library preparation method for next-generation sequencing," Nature Methods, 6(10), 2009, i-ii.
Syed, "Next-generation sequencing library preparation: simultaneous fragmentation and tagging using in vitro transposition," Application Notes, Nature Methods, Epicentre Biotech, Nov. 2009, i-ii.
Taylor et al., "Characterization of chemisorbed monolayers by surface potential measurements", J. Phys. D: Appl. Phys., 24, 1991, 1443.
The protocol for Roche 454 FLX Titanium emPCR.
Adey et al., "Rapid, low-input, low-bias construction of shotgun fragment libraries by high-density in vitro transposition," Genome Biology vol. 11(12) (2010) R119.
Adey et al., "Ultra-low-input, tagmentation-based whole-genome bisulfiete sequencing", Genome Research, vol. 22, 2012, pp. 1139-1143.
Amini et al., "Haplotype-resolved whole-genome sequencing by contiguity-preserving transposition and combinatorial indexing", Nature Genetics, vol. 46 No. 12, Dec. 2014, 134 3-13 4 9.
Amini et al., "Supplementary information for: Haplotype-resolved whole-genomes sequencing by contiguity-preserving transposition and combinatorial indexing", Nature Genetics, vol. 46 No. 12, Dec. 2014, 1-16.

Bains et al., "A novel method for nucleic acid sequence determination", J. Theor Biol., 135(3), 1998, 303-307.
Ball et al., "Targeted and genome-scale strategies reveal gene-body methylation signatures in human cells," Nat Biotechnol 27(4), 2009, 361-368.
Bansal et al., "HapCUT: An efficient and accurate algorithm for the haplotype assembly problem," Bioinformatics; 24 (16), 2008, i153-9.
Batzoglou et al., "ARACHNE: a whole-genome shotgun assembler," Genome Research, 12(1), 2002, 177-189.
Benetti et al., "A mammalian microRNA cluster controls DNA methylation and telomere recombination via Rb12-dependent regulation of DNA methvitransferases," Nat Struct Mo! Bio 15(3), 2008, 268-279.
Bentley et al., "Accurate whole human genome sequencing using reversible terminator chemistry," Nature, vol. 456, No. 7218, 2008, 53-59.
Bimber et al., "Whole-genome characterization of human and simian immunodeficiency vims intrahost diversity bv ultradeep pvroseauencing," Journal of Virology, vol. 84, No. 22, 2010, 12087-12092.
Bloch et al., "Purification of *Escherichia coli* chromosomal segments without cloning," Biochemical and Biophvsical Research Communications, vol. 223, 1996, 104-111.
Boeke et al., "Transcription and reverse transcription of retrotransposons," Ann. Rev. Micro biol. 1989, 43, 403-434.
Branton et al., "The potential and challenges of nanopore sequencing," Nature Biotechnology, vol. 26, No. 10, Oct. 2008, 1146-1153.
Braslavsky et al., "Sequence information can be obtained from single DNA molecules," PNAS, 100(7), 2003, 3960-3964.
Brown et al., "Retroviral Integration: Structure of the Initial Covalent Product and Its Precursor, and a Role for the Viral IN Protein", PNAS, 86, 1989, 2525-9.
Brownlie et al., "The Caenorhabditis briggsae genome contains active CbmaTI and Tcbl transposons," Molecular Genetics and Genomics, vol. 273, 2005, 92-101.
Caruccio et al., "Preparation of next-generation sequencing libraries using Nextera(TM) technology: simultaneous DNA fragmentation and adaptor tagging by in vitro transposition," Methods in Molecular Biology, 733, 2011, 241-255.
Chernoff et al., "Molecular Analysis of the von Hippei-Lindau Disease Gene," Methods Mol. Med. 2001, 53:193-216.
Clark et al., "High sensitivity mapping of methylated cytosines," Nucleic Acids Research, vol. 22, No. 15, 1994, 2990-2997.
Cockroft et al., "A single-molecule nanopore device detects DNA polymerase activity with single-nucleotide resolution", J. Am. Chem. Soc, 130(3), 2008, 818-820.
Cokus et al., "Shotgun Bisulphite Sequencing of the *Arabidopsis* Genome Reveals DNA Methylation Patterning," Nature 452(7184), 2008, 215-219.
Colegio et al., "In vitro transposition system for efficient generation of random mutants of Campylobacter jejuni", J. Bacterial, 183, 2001, 2384-8.
Craig, "Transposon Tn7", Review in: Curr Top Microbial Immunol, 204, 1996, 27-48.
Craig, "V(D)J Recombination and Transposition: Closer Than Expected", Science, 271, 5255, 1996, 1512.
De Vries et al., "PCR on Cell Lysates Obtained from Whole Blood Circumvents DNA Isolation," Clin. Chem. 2001, 47, 1701-1702.
Deamer et al., "Characterization of nucleic acids by nanopore analysis", ACC Chem Res, 35(10), 2002, 817-825.
Deamer et al., "Nanopores and nucleic acids: prospects for ultrarapid sequencing", Trends Biotechnol, 18(4), 2000, 147-151.
Dean et al., "Comprehensive human genome amplification using multiple displacement amplification", PNAS, 99, 2002, 5261-5266.
Deng et al., "Targeted bisulfite sequencing reveals changes in DNA methylation associated with nuclear reprogramming," Nat Biotechnol 27(4), 2009, 353-360.
Down et al., "A Bayesian deconvolution strategy for immunoprecipitation-based DNA methylome analysis," Nat Biotechnol 26(7), 2008, 779-785.

(56) References Cited

OTHER PUBLICATIONS

Dressman et al., "Transforming single DNA molecules into fluorescent magnetic particles for detection and enumeration of genetic variations," PNAS, 100(15), 2003, 8817-8822.
Drmanac et al., "Accurate sequencing by hybridization for DNA diagnostics and individual genomics", Nature Biotechnology 16(1), 1998, 54-8.
Drmanac et al., "Human genome sequencing using unchained base reads on self-assembling DNA nanoarrays," Science 327(5961), 2009, 78-81.
Duan et al., "A three-dimensional model of the yeast genome," Nature 465(7296), 2010, 363-7.
Duitama et al., Proceedings of the First ACM International Conference on Bioinformatics and Computational Biology, 160-169, 2010.
Eid et al., "Real-Time DNA Sequencing from Single Polymerase Molecules," Science 323, 2009, 133-138.
Ewing, et al., "Base-calling of automated sequencer traces usingphred. II. Error probabilities", Genome Research, 8, 1998, 186-194.
Fan et al., "Whole-genome molecular haplotyping of single cells.," Nat Biotech 29(1), 2011, 51-57.
Filee et al., "Insertion Sequence Diversity in Archaea," Microbiology and Molecular Biology Reviews, vol. 71, No. I, 2007, 121-157.
Fodor et al., "Light-Directed, Spatially Addressable Parallel Chemical Synthesis", Science, vol. 251, 1991, 767-773.
Fullwood et al., "An oestrogen-receptor-a-bound human chromatin interactome," Nature 462, 2009, 58-64.
Fullwood et al., "Chromatin interaction analysis using paired-end tag sequencing," Current Protocols in Molecular Biology, Supplement 89, Jan. 21, 2010, 21.15.1-21.15.25.
Gal et al., "Directional cloning of native PCR products with preformed sticky ends (autosticky PCR)," Molecular & General Genetics, vol. 260, No. 6, Jan. 1999, 569-573.
Geiss et al., "Direct multiplexed measurement of gene expression with color coded probe pairs," Nat Biotechnol. 26 (3), 2008, 317-25.
Gloor, "Gene targeting in *Drosophila*", Methods Mol Biol. 260, 2004, 97-114.
Gnerre et al., "High-quality draft assemblies of mammalian genomes from massively parallel sequence data," Proc Natl Acad Sci USA., [Epub ahead of print] PubMed PMID: 21187386, Dec. 27, 2010.
Goodman et al., "Identifying genetic determinants needed to establish a human gut symbiont in its habit," Cell Host & Microbe, vol. 6, Sep. 2009, 279-289.
Goryshin et al., "Tn5 in Vitro Transposition," J. Biol. Chem. 1998, vol. 273, No. 13, 7367-7374.
Grunenwald et al., "Nextera PCR-Free DNA Library Preparation for Next-Generation Sequencing," (Poster Presentation, AG8T) 2011.
Grunenwald et al., "Rapid, high-throughput library preparation for next-generation sequencing, Nature Methods, Application Notes," Aug. 2010, iii-iv.
GS FLX Titanium L V emPCR Kit (Lib-L) protocol, Aug. 2008, 1-2.
Gu et al., "Preparation of reduced representation bisulfite sequencing libraries for genome-scale DNA methylation profiling," Nat Protoc 6(4), 2011, 468-481.
Haapa, et al., "An efficient and accurate integration of mini-Mu transposons in vitro: a general methodology for functional genetic analysis and molecular biology applications", Nucleic Acids Research vol. 27, No. 13, 1999, 2777-2784.
Handelsman, J. et al., "Metagenomics: Application of Genomics to Uncultured Microorganisms", Microbiology and Molecular Biology Reviews, 68(4), Dec. 2004, 669-685.
Harris et al., "Comparison of sequencing-based methods to profile DNA methylation and identification of monoallelic epigenetic modifications.," Nat Biotechnol 28(10), 2010, 1097-1105.
Healy, "Nanopore-based single-molecule DNA analysis", Nanomed. 2(4), 2007, 459-481.
Heredia et al., "In vitro double transposition for DNA identification," Analytical Biochemistry 3992010, 78-83.
Hiatt et al., "Tag-directed assembly of locally derived short sequence reads," Nat Methods. 7(2), 2010, 119-22.

Ichikawa, et al., "In vitro transposition of transposon Tn3", J Biol Chem, 265, 1990, 18829-32.
International Preliminary Report on Patentability mailed in PCT application No. PCT/IB2014/000610, dated Jul. 14, 2015.
Ivics et al., "Targeted Sleeping Beauty Transposition in Human Cells," Molecular Therapy, vol. 15, No. 6, pp. 1137-1144, Jun. 2007.
Jackson et al., "Plasmid tagging for efficient large-scale sequence completion of entire clone inserts," BioTechniques, vol. 34, Mar. 2003, 604-608.
Johnson et al., "DNA sequences at the ends of transposon Tn5 required for transposition," Nature, vol. 304, No. 6923, pp. 280-282, Jul. 1983.
Johnson et al., "Genome-wide mapping of in vivo protein-DNA interactions," Science 316(5830), 2007, 1497-502.
Joos, "Covalent attachment of hybridizable oligonucleotides to glass supports", Analytical Biochemistry, 247, 1997, 96-101.
Keith et al., "Algorithms for Sequence Analysis via Mutagenesis," Bioinformatics, vol. 20 No. 15; published online doi:10.1093/bioinformatics/bth258, May 14, 2004, 2401-2410.
Keith et al., "Unlocking Hidden Genomic Sequence," Nucleic Acids Research, vol. 32, No. 3, published online DOI: 10.1093/nar/gnh022, Feb. 18, 2004, e35.
Khandjian, "UV crosslinking of RNA to nylon membrane enhances hybridization signals", Mo !. Bio. Rep, 11, 1986, 107-115.
Kidd et al., "Mapping and sequencing of structural variation from eight human genomes," Nature 453 (7191), 2008, 56-64.
Kirby, "in vivo mutagenesis using EZ-Tn5ATM.," Methods in Enzymology, vol. 421, 2007, 17-21.
Kirby, et al., "Cryptic plasmids of *Mycobacterium avium* Tn552 to the rescue", Molecular Microbiology, 43, 2002, 173-86.
Kitzman et al., "Haplotype-resolved genome sequencing of a Gujarati Indian individual," Nature Biotechnology, vol. 29(1), Jan. 2011, 59-63.
Kleckner, et al., "TnIO and ISIO transposition and chromosome rearrangements: mechanism and regulation in vivo and in vitro", Curr Top Microbial Immunol., 204, 1996, 49-82.
Korlach, et al., "Selective aluminum passivation for targeted immobilization of single DNA polymerase molecules in zero-mode waveguide nanostructures", PNAS, 105(4), 2008, 1176-1181.
Kramer, "cDNA Library Construction from Single Cells," Current Protocols in Neuroscience, 2002, 4.27.1-4.27.19.
Lage, Jose M. et al., "Whole genome analysis of genetic alterations in small DNA samples using hyperbranched strand displacement amplification and array-CGH", Genome Research 2003, vol. 13 ., Issue 2, 294-307.
Lai et al., "A shotgun optical map of the entire Plasmodium falcipamm genome," Nat Genet. 23(3), 1999, 309-13.
Lampe, et al., "A purified mariner transposase is sufficient to mediate transposition in vitro", EMBO J., 15, 1996, 5470-5479.
Lander et al., "Initial sequencing and analysis of the human genome," Nature, 409(6822), 2001, 860-921.
Lehoux et al., "Defined oligonucleotide tag pools and PCR screening in signature-tagged mutagenesis of essential genes from bacteria," Biotechniques 1999, vol. 26, No. 3, 473-478,480.
Levene et al., "Zero-Mode Waveguides for Single-Molecule Analysis at high concentrations", Science 299, 2003, 682-686.
Levy et al., "The Diploid Genome Sequence of an Individual Human," PLOS Biology, vol. 5, Issue 10, 2007, 2113-2144.
Li et al., "De novo assembly of human genomes with massively parallel short read sequencing," Genome Res. 20 (2), 2010, 265-72.
Li et al., "DNA molecules and configurations in a solid-state nanopore microscope", Nature Mater, 2(9), 2003, 611-615.
Li et al., "Primasebased whole genome amplification," Nucleic Acids Res. 36(13), 2008, e79.
Li et al., "The DNA methylome of human peripheral blood mononuclear cells," PLOS Biol 8(11), 2010, el000533.
Li, et al., "Fast and accurate short read alignment with Burrows-Wheeler transform," Bioinformatics 25:1754-1760, 2009.
Lieberman-Aid En et al., "Comprehensive mapping of long-range interactions reveals folding principles of the human genome," Science, 326(5950), 2009, 289-93.

(56) References Cited

OTHER PUBLICATIONS

Lim et al., "Shotgun optical maps of the whole *Escherichia coli* 0157:H7 genome," Genome Res. 11(9), 2001, 1584-93.
Lin et al., "Whole genome shotgun optical mapping of Deinococcus radiodurans. ," Science 285 ( 54 3 3): 1999, 1558-62.
Lister, et al., "Human DNA methylomes at base resolution show widespread epigenomic differences," Nature, 462 (7271), Nov. 19, 2009, 315-322.
Lizardi, "Mutation detection and single-molecule counting using isothermal rolling-circle amplification", Nature Genetics, vol. 19, 1998, 225-232.
Lundquist et al., "Parallel confocal detection of single molecules in real time", Opt. Lett. 33(9), 2008, 1026-1028.
Mahillon et al., "Insertion Sequences," Microbiology and Molecular Biology Reviews, vol. 62, No. 3, 725-774, Sep. 1998.
Mardis, "Next-Generation DNA Sequencing Methods," Annu Rev Genomics Hum Genet. 2008, 9:3 87-402.
Mardis, E.R., "The impact of next-generation sequencing technology on genetics", Trends in Genetics 24, 2008, 133-141.
Margulies et al., "Genome sequencing in microfabricated high-density picolitre reactors," Nature, vol. 437, 2005, 376-380 and Supplemental Materials.
Marine et al., "Evaluation of a transposase protocol for rapid generation of shotgun high-throughput sequencing libraries from nano gram quantities of DNA," Appl. Environ. Microbial, vol. 77 (22), Nov. 2011, 8071-8079.
Mazutis et al., "Droplet-based microfluidic systems for high-throughput single DNA molecule isothermal amplification and analysis," Anal Chem. 81 (12), 2009, 4813-21.
ASHG Meetings, Book of Abstracts for the 64th Annual Meeting of ASHG, ASHG Meetings Oct. 2014, San Diego, CA, Abstract Publication Date, Electronic Email, 2 pgs.
Brouilette, et al., "A Simple and Novel Method for RNA-Seq Library Preparation of Single Cell cDNA Analysis by Hyperactive Tn5 Transposase," Developmental Dynamics, 2012, pp. 1584-1590.
Choi et al., "Applications of Transposon-Based Gene Delivery System in Bacteria," Journal of Microbiology and Biotechnology, 2009, pp. 217-228.
Cline et al., "PCR Fidelity of Pfu DNA Polymerase and Other Thermostable DNA Polymerases," Nucleic Acids Reseach, 1996, vol. 24, No. 18, pp. 3546-3551.
Goryshin et al., "Tn5/IS50 Target Recognition," Proceedings of the National Academy of Sciences, 1998, vol. 5, pp. 10716-10721.
Head et al., "Library Construction for Next-Generation Sequencing: Overview and Challenges," Biotechniques, 2014, vol. 56, No. 2, pp. 61-64, 66, 68.
Lamble et al., "Improved Workflows for High Throughput Library Preparation Using the Transposome-Based Nextera System", BMC Biotechnolgy, 2013, vol. 13, p. 104.
Leschziner et al., "Tn552 Transposase Catalyzes Concerted Stand Transfer In Vitro," Proc. Natl. Acad. Sci., 1998, vol. 95, pp. 7345-7350.
Mazurkiewicz et al., "Signature-Tagged Mutagenesis: Barcoding Mutants for Genome-Wide Screens," Nature Reviews, Genetics, 2006, vol. 7, pp. 929-939.
Perez-Arnaiz et al., "Functional Importance of Bacteriophage phi29 DNA Polymerase Residue Tyr148 in Primer-terminus Stabilisation at the 3'-5' Exonuclease Active Site," Journal of Molecular Biology, 2009, pp. 797-807.
Picelli et al., "Full-Length RNA-seq From Single Cells Using Smart-seq2", Nature Protocols, Nature Publishing Group, GB, 2014, vol. 9, No. 1, pp. 171-181.
Rahnenfuhrer et al., "Hybrid Clustering for Microarray Image Analysis Combining Intensity and Shape Features"; BMC Bioinformatics, 2004, vol. 5, Article 47, pp. 1-11.
Silander et al., "Chapter 1: Whole Genome Amplification with Phi29DNA Polymerase to Enable Genetic or Genomic Analysis of Samples of Low DNA Yield," Methods in Molecular Biology, Genomics Protocols: Second Edition, 2008, vol. 439, pp. 1-18.
Skoko et al., "Micromechanical Analysis of the Binding of DNA-Bending Proteins HMGB1, NHP6A, and HU Reveals Their Ability to Form Highly Stable DNA-Protein Complexes," Biochemistry, 2004, vol. 43, pp. 13867-73874.
Steiniger et al., "Defining Characteristics of Tn5 Transposase Non-Specific DNA Binding," Nucleic Acids Research, 2006, vol. 34, No. 9, pp. 2820-2832.
Zhang et al., "An Industrial Solution to Automatic Robot Calibration and Workpiece Pose Estimation for Semiconductor and Gene-Chip Microarray Fabrication," Ind. Robot, 2006, vol. 33, pp. 88-96.

\* cited by examiner

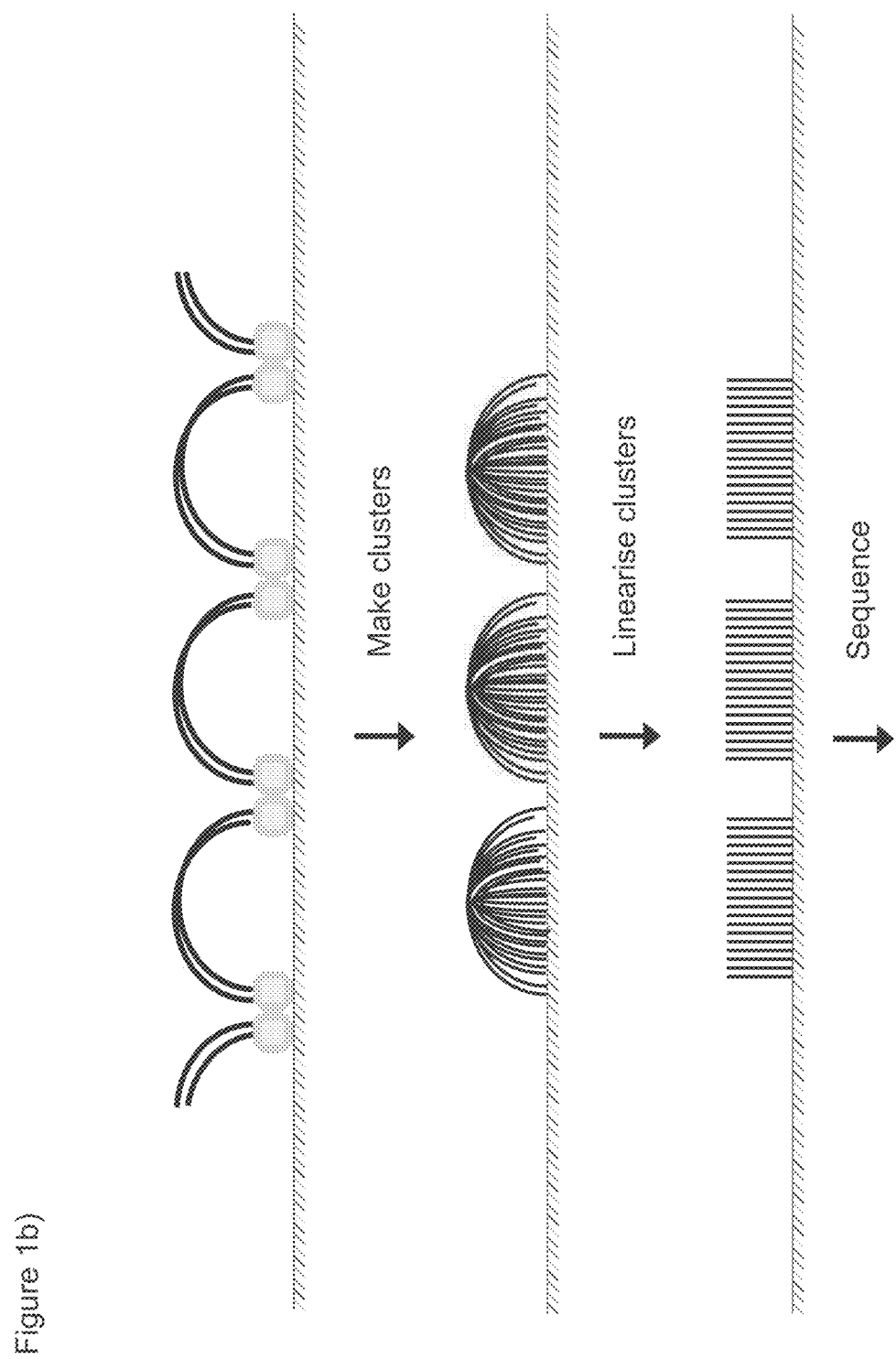

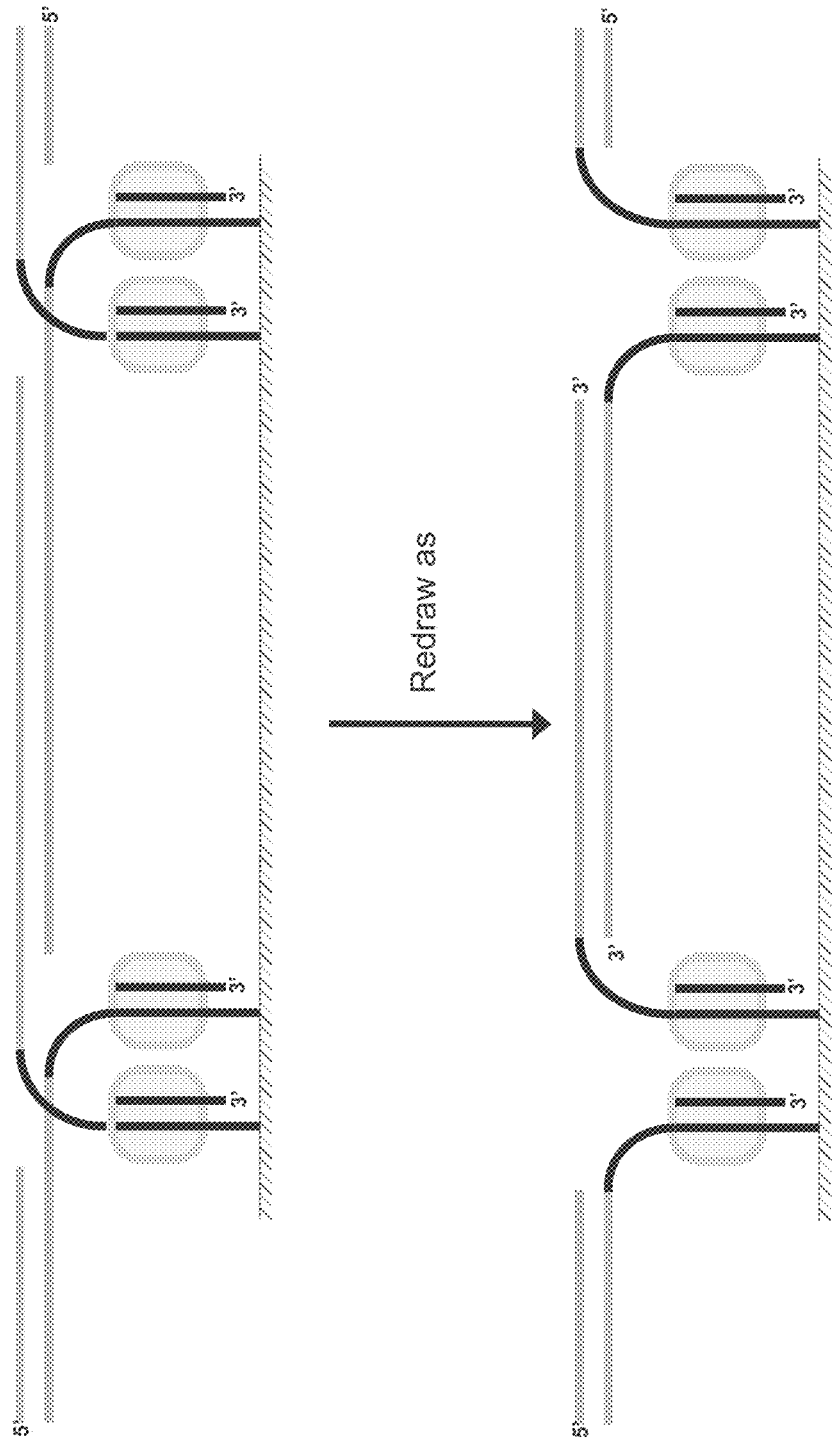

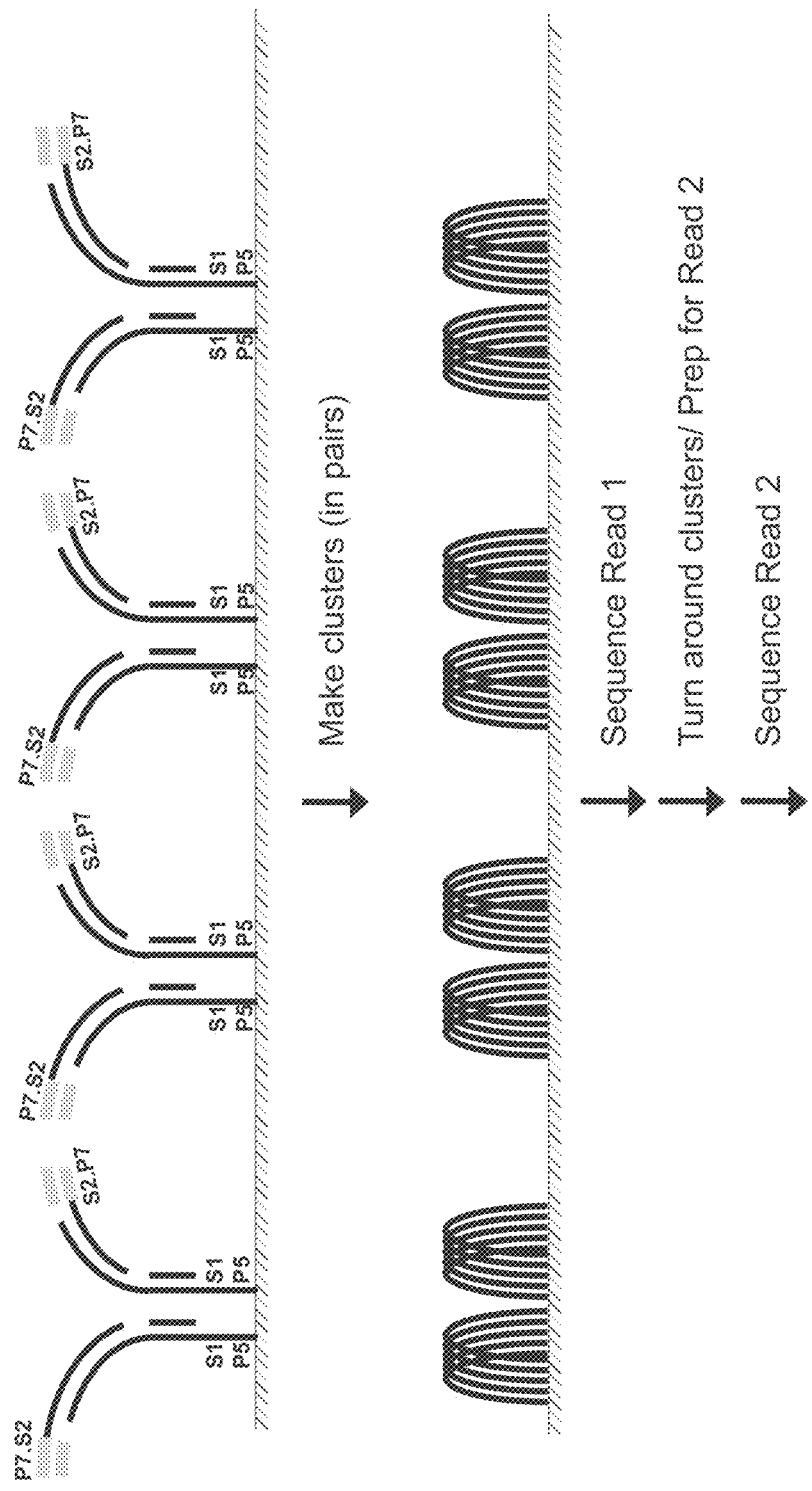

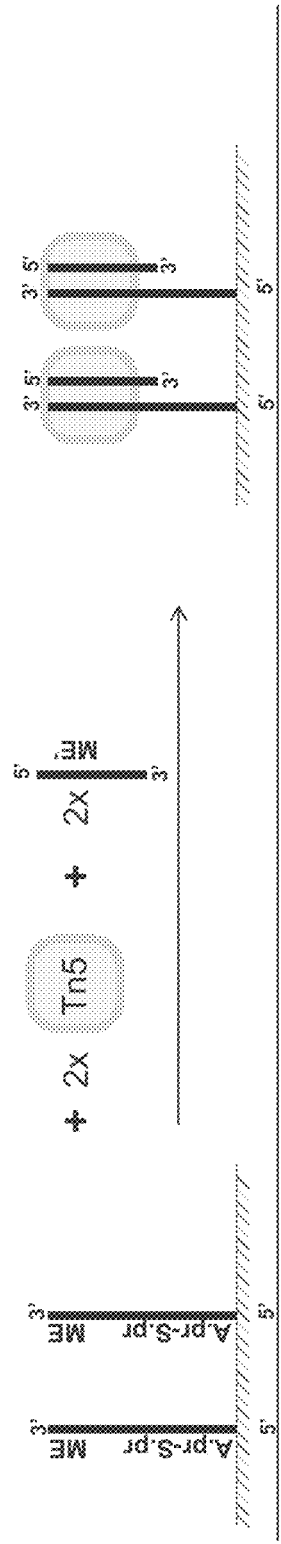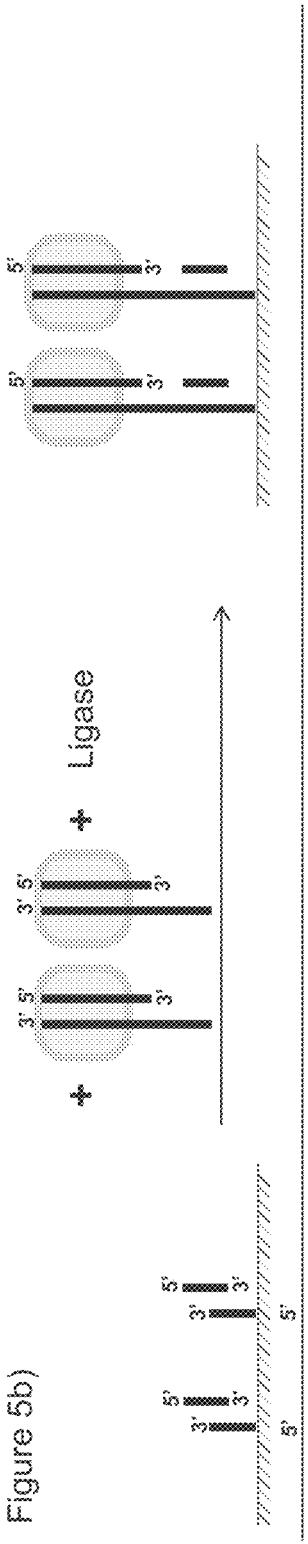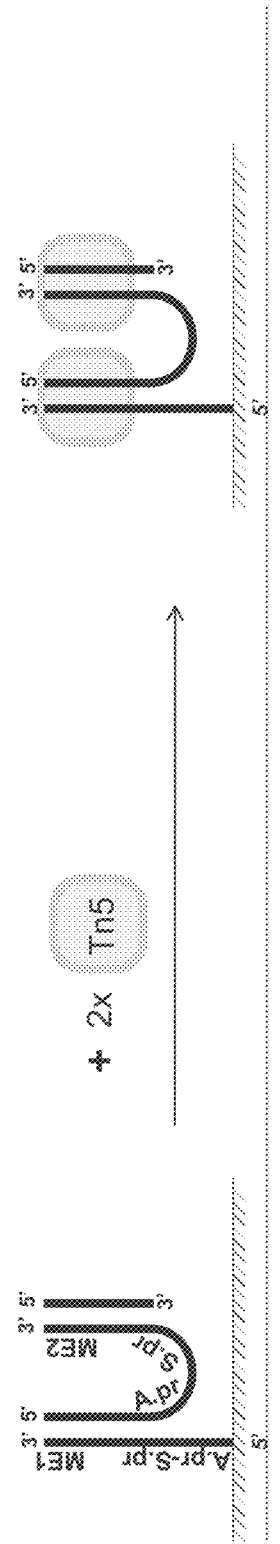

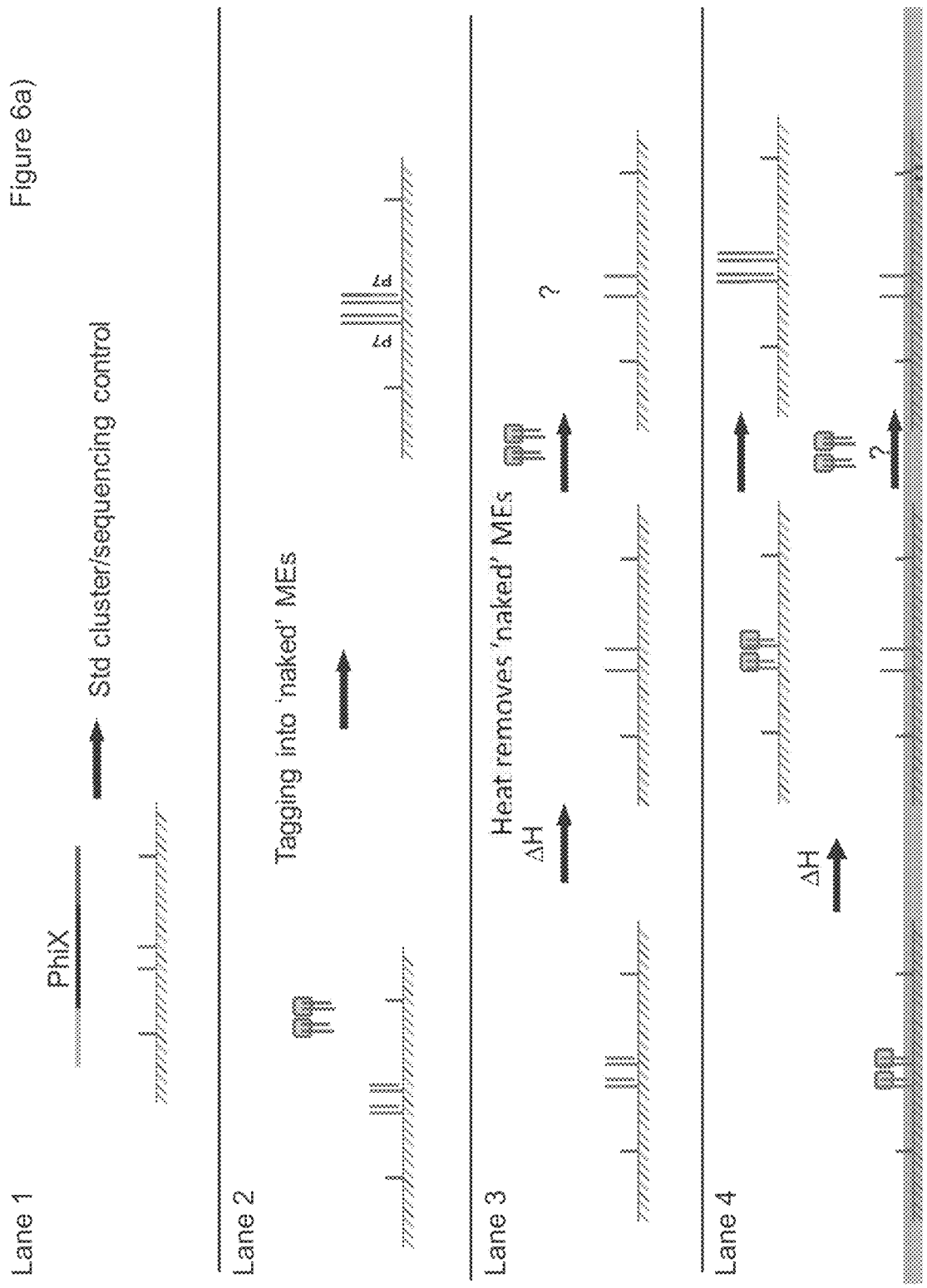

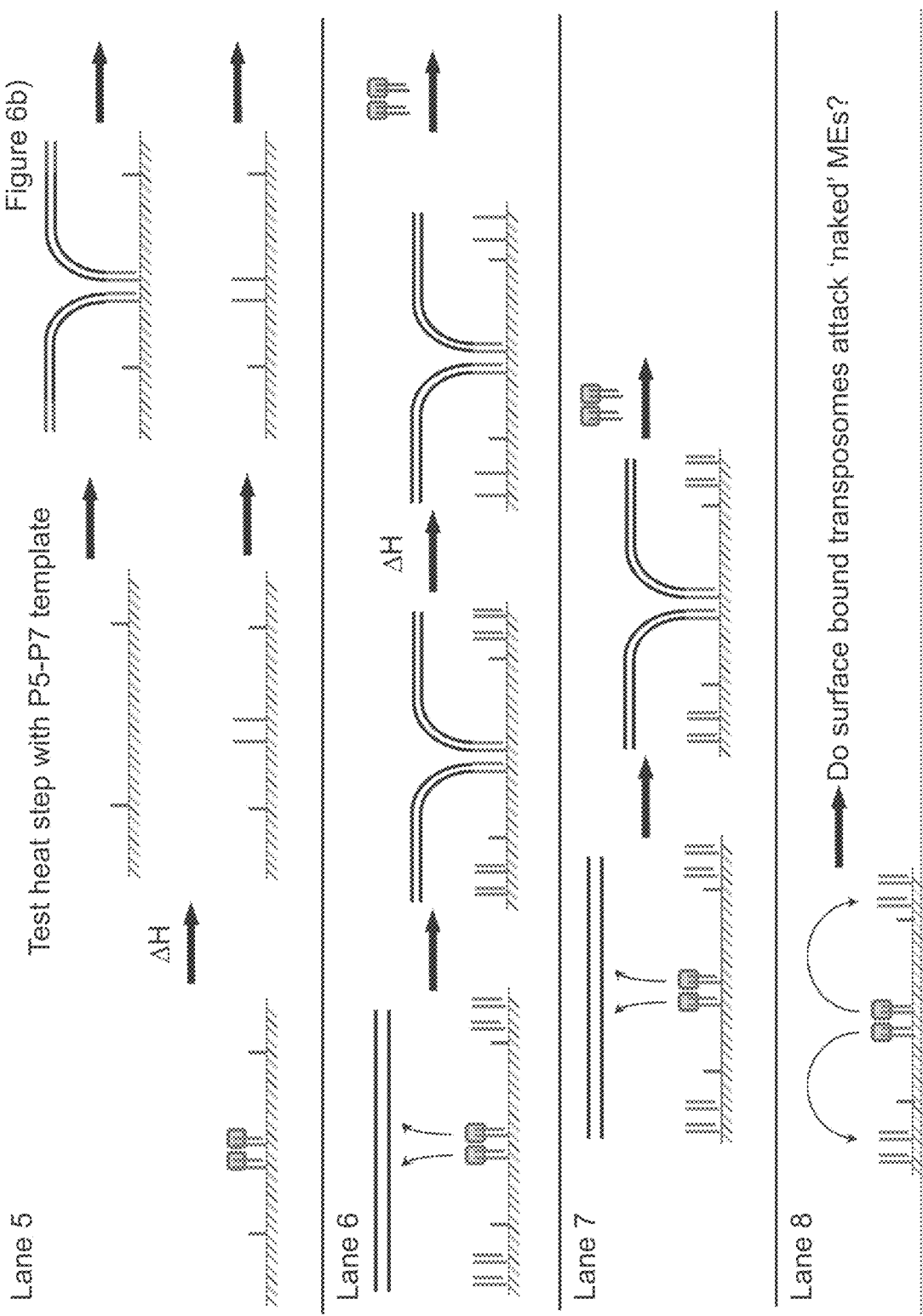

Figure 7 (Lane 6 condition):
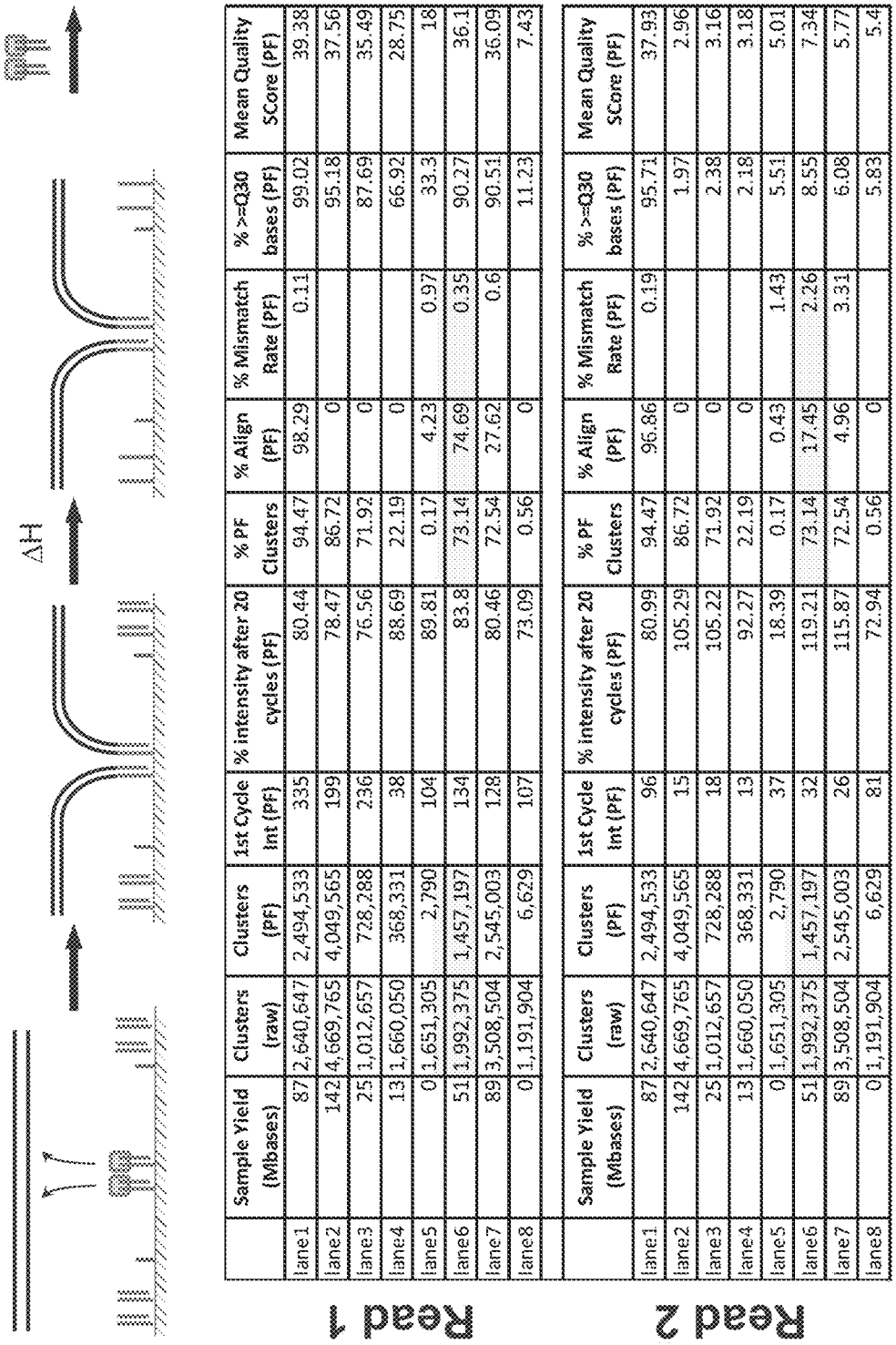
| | Sample Yield (Mbases) | Clusters (raw) | Clusters (PF) | 1st Cycle Int (PF) | % intensity after 20 cycles (PF) | % PF Clusters | % Align (PF) | % Mismatch Rate (PF) | % >=Q30 bases (PF) | Mean Quality Score (PF) |
|---|---|---|---|---|---|---|---|---|---|---|
| Read 1 | | | | | | | | | | |
| lane1 | 87 | 2,640,647 | 2,494,533 | 335 | 80.44 | 94.47 | 98.29 | 0.11 | 99.02 | 39.38 |
| lane2 | 142 | 4,669,765 | 4,049,565 | 199 | 78.47 | 86.72 | 0 | | 95.18 | 37.56 |
| lane3 | 25 | 1,012,657 | 728,288 | 236 | 76.56 | 71.92 | 0 | | 87.69 | 35.49 |
| lane4 | 13 | 1,660,050 | 368,331 | 38 | 88.69 | 22.19 | 0 | | 66.92 | 28.75 |
| lane5 | 0 | 1,651,305 | 2,790 | 104 | 89.81 | 0.17 | 4.23 | 0.97 | 33.3 | 18 |
| lane6 | 51 | 1,992,375 | 1,457,197 | 134 | 83.8 | 73.14 | 74.69 | 0.35 | 90.27 | 36.1 |
| lane7 | 89 | 3,508,504 | 2,545,003 | 128 | 80.46 | 72.54 | 27.62 | 0.6 | 90.51 | 35.09 |
| lane8 | 0 | 1,191,904 | 6,629 | 107 | 73.09 | 0.56 | 0 | | 11.23 | 7.43 |
| Read 2 | | | | | | | | | | |
| lane1 | 87 | 2,640,647 | 2,494,533 | 96 | 80.99 | 94.47 | 96.86 | 0.19 | 95.71 | 37.93 |
| lane2 | 142 | 4,669,765 | 4,049,565 | 15 | 105.29 | 86.72 | 0 | | 1.97 | 2.96 |
| lane3 | 25 | 1,012,657 | 728,288 | 18 | 105.22 | 71.92 | 0 | | 2.38 | 3.16 |
| lane4 | 13 | 1,660,050 | 368,331 | 13 | 92.27 | 22.19 | 0 | | 2.18 | 3.18 |
| lane5 | 0 | 1,651,305 | 2,790 | 37 | 18.39 | 0.17 | 0.43 | 1.43 | 5.51 | 5.01 |
| lane6 | 51 | 1,992,375 | 1,457,197 | 32 | 119.21 | 73.14 | 17.45 | 2.26 | 8.55 | 7.34 |
| lane7 | 89 | 3,508,504 | 2,545,003 | 26 | 115.87 | 72.54 | 4.96 | 3.31 | 6.08 | 5.77 |
| lane8 | 0 | 1,191,904 | 6,629 | 81 | 72.94 | 0.56 | 0 | | 5.83 | 5.4 |

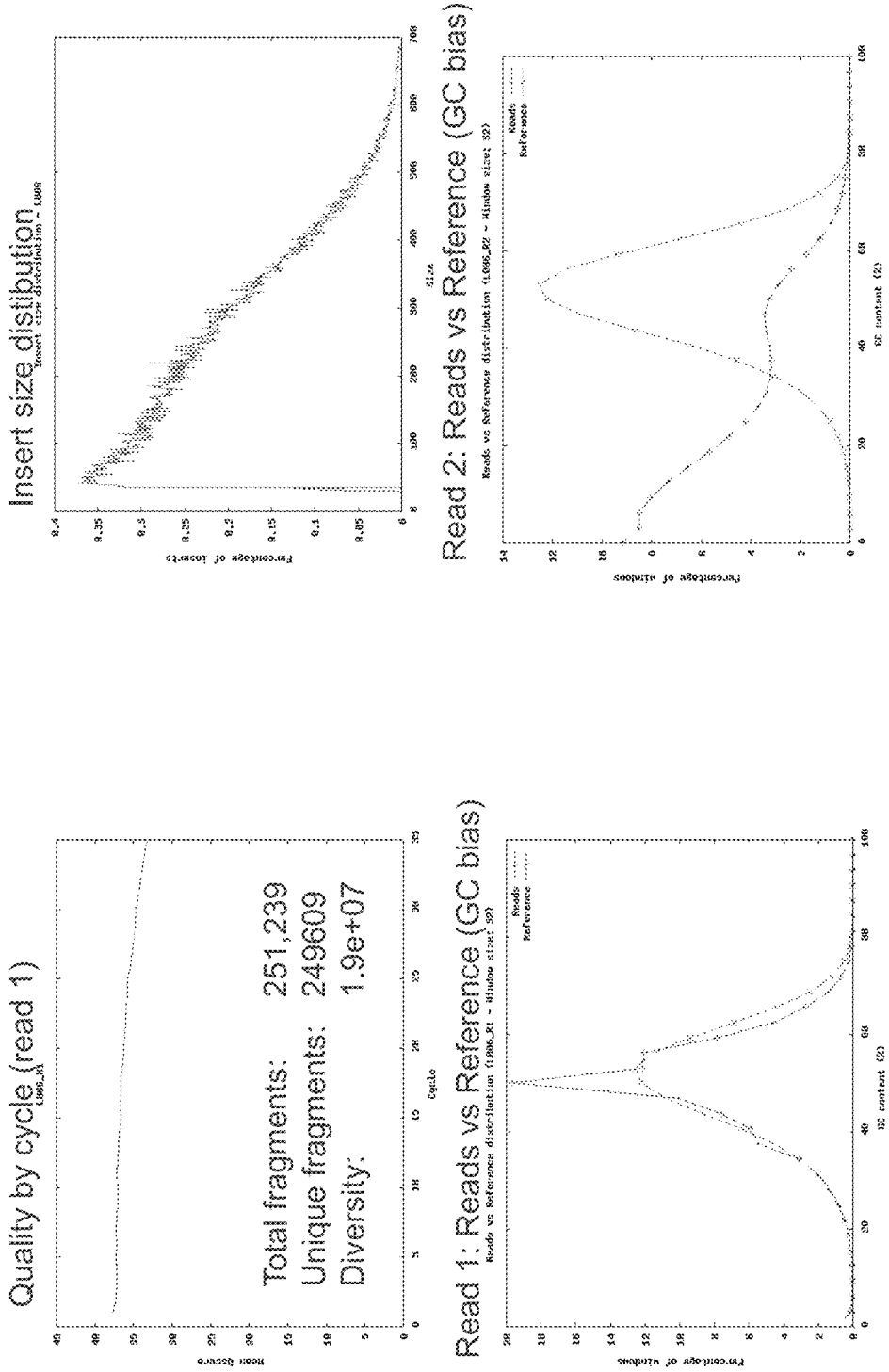
Figure 8 (Lane 6 condition): Primary analysis metrics of lane 6

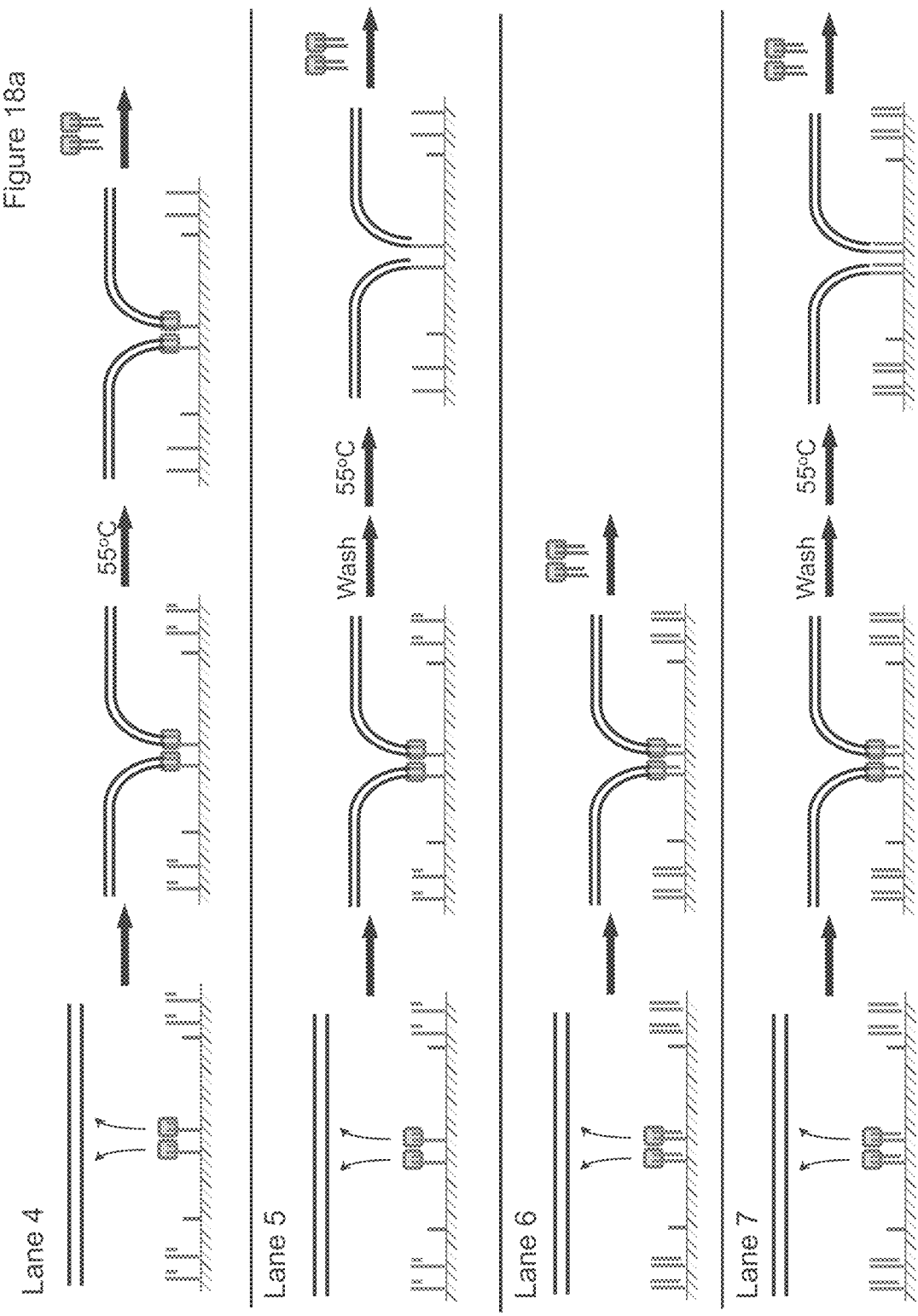

Figure 18b

Read 1

| | Yield (Mb) | Clusters (raw) | Clusters (PF) | 1st Cycle Int (PF) | % int after 20 cycles (PF) | % PF Clusters | % Align (PF) | % Mismatch Rate (PF) | % >=Q30 bases (PF) | Mean Quality Score (PF) |
|---|---|---|---|---|---|---|---|---|---|---|
| lane 1 | 204 | 6,172,822 | 5,821,910 | 226 | 84.42 | 94.32 | 98.24 | 0.04 | 98.75 | 39.16 |
| lane 2 | 178 | 5,676,854 | 5,096,648 | 170 | 84.02 | 89.78 | 93.81 | 0.08 | 97.78 | 38.74 |
| lane 3 | 261 | 8,915,997 | 7,450,306 | 168 | 82.73 | 83.56 | 89.9 | 0.13 | 95.42 | 37.7 |
| lane 4 | 89 | 2,963,760 | 2,542,838 | 120 | 85.56 | 85.8 | 96.47 | 0.11 | 95.99 | 38.14 |
| lane 5 | 96 | 3,223,900 | 2,728,667 | 103 | 83.66 | 84.64 | 96.41 | 0.12 | 95.22 | 37.82 |
| lane 6 | 109 | 3,801,294 | 3,103,977 | 105 | 85.96 | 81.66 | 22.59 | 0.11 | 95.21 | 37.69 |
| lane 7 | 123 | 4,239,062 | 3,513,343 | 112 | 85.31 | 82.88 | 15.52 | 0.17 | 95.64 | 37.82 |
| lane 8 | 0 | 2,230,575 | 0 | 0 | 0 | 0 | | | | |

SAMPLE PREPARATION ON A SOLID SUPPORT

RELATED APPLICATIONS

This application is a continuation of U.S. patent application Ser. No. 16/027,052, filed on Jul. 3, 2018, which is a continuation of U.S. patent application Ser. No. 14/671,071, filed on Mar. 27, 2015, now U.S. Pat. No. 10,041,066, which is a continuation of U.S. patent application Ser. No. 13/790,220, filed on Mar. 8, 2013, now U.S. Pat. No. 9,683,230, which claims priority to U.S. Provisional Application No. 61/750,682, filed on Jan. 9, 2013, which are hereby incorporated by reference in their entirety.

BACKGROUND

There are a variety of methods and applications for which it is desirable to generate a library of fragmented and tagged DNA molecules from double-stranded DNA (dsDNA) target molecules. Often, the purpose is to generate smaller DNA molecules (e.g., DNA fragments) from larger dsDNA molecules for use as templates in DNA sequencing reactions.

Many of the methods currently used for fragmentation and tagging of double-stranded DNA for use in next-generation sequencing are wasteful of the DNA, require expensive instruments for fragmentation, and the procedures for fragmentation, tagging and recovering tagged DNA fragments are difficult, tedious, laborious, time-consuming, inefficient, costly, require relatively large amounts of sample nucleic acids. In addition, many of these methods generate tagged DNA fragments that are not fully representative of the sequences contained in the sample nucleic acids from which they were generated. Thus, what is needed in the art are methods that provide speed and ease of use when generating libraries of tagged DNA fragments from target DNA and which can be easily applied to nucleic acid analysis methods such as next-generation sequencing and amplification methods.

BRIEF SUMMARY

Presented herein are methods and compositions for nucleic acid sample preparation on a solid support. The methods and compositions especially relate to methods and compositions for fragmenting and tagging DNA using transposon compositions immobilized to a solid support. The methods and compositions presented herein are useful, for example, for generating libraries of tagged DNA fragments for use, e.g., in next generation sequencing methods, and the like. In some preferred embodiments, the present invention relates to preparation of linear ssDNA fragments on a solid support from target DNA comprising any dsDNA of interest (including double-stranded cDNA prepared from RNA), from any source, for genomic, subgenomic, transcriptomic, or metagenomic analysis, or analysis of RNA expression.

Accordingly, presented herein are methods of preparing an immobilized library of tagged DNA fragments comprising: (a) providing a solid support having transposome complexes immobilized thereon, wherein the transposome complexes comprise a transposase bound to a first polynucleotide, the first polynucleotide comprising (i) a 3' portion comprising a transposon end sequence, and (ii) a first tag comprising a first tag domain; and (b) applying a target DNA to the solid support under conditions whereby the target DNA is fragmented by the transposome complexes, and the 3' transposon end sequence of the first polynucleotide is transferred to a 5' end of at least one strand of the fragments; thereby producing an immobilized library of double-stranded fragments wherein at least one strand is 5'-tagged with the first tag. In some embodiments, the transposome complexes comprise a second polynucleotide comprising a region complementary to said transposon end sequence. The methods can further comprise (c) providing transposome complexes in solution and contacting the transposome complexes with the immobilized fragments under conditions whereby the target DNA is fragmented by the transposome complexes in solution; thereby obtaining immobilized nucleic acid fragments having one end in solution. In some embodiments, the transposome complexes in solution can comprise a second tag, such that the method generates immobilized nucleic acid fragments having a second tag, the second tag in solution. The first and second tags can be different or the same.

Also presented herein are solid supports having a library of tagged DNA fragments immobilized thereon prepared according to the above methods or other methods. For example, presented herein are solid supports having transposome complexes immobilized thereon, wherein the transposome complexes comprise a transposase bound to a first polynucleotide, the polynucleotide comprising (i) a 3' portion comprising a transposon end sequence, and (ii) a first tag comprising a first tag domain.

Also presented herein are methods of generating a flowcell, comprising immobilizing a plurality of transposome complexes to a solid support, the transposome complexes comprising a transposase bound to a first polynucleotide, the first polynucleotide comprising (i) a 3' portion comprising a transposon end sequence, and (ii) a first tag comprising a first tag domain.

The methods can further comprise providing a solid support having a plurality the first polynucleotides immobilized thereon, and contacting the solid support with transposase holoenzyme and a second polynucleotide, the second polynucleotide comprising a region complementary to the transposon end sequence. In some embodiments of the methods, immobilizing comprises (a) providing a solid support having amplification primers coupled thereto; (b) hybridizing a second polynucleotide to one of the amplification primers, the second oligonucleotide comprising a region complementary to a transposon end sequence and a region complementary to the first tag; (c) extending the amplification primer using a polymerase to generate a duplex comprising the first polynucleotide hybridized to the second polynucleotide, the first polynucleotide immobilized directly to the solid support; and (d) contacting the solid support with transposase holoenzyme, thereby assembling a transposome complex on the solid support.

Also presented herein is a population of microparticles having transposome complexes immobilized thereto, the transposome complexes comprising a transposase bound to a first polynucleotide and a second polynucleotide; wherein the first polynucleotide is immobilized at its 5' end to the surface of the microparticle and the second polynucleotide is hybridized to the 3' end of the first polynucleotide; and wherein the first polynucleotide comprises: (i) a 3' portion comprising a transposon end sequence, and (ii) a first tag comprising a first tag domain. Also presented herein are methods of producing an immobilized library of tagged DNA fragments comprising contacting a target DNA with the above population of microparticles to generate immobilized tagged DNA fragments.

Also presented herein are methods of generating a library of tagged DNA fragments for index-directed assembly into a longer sequence read, the method comprising: providing a population of microparticles having transposome complexes immobilized thereto, the transposome complexes comprising a transposase bound to a first polynucleotide comprising an index domain associated with the microparticle and a second polynucleotide; applying a target DNA to the population of microparticles, thereby generating immobilized DNA fragments that are tagged with the index domain. In certain embodiments of the above methods, the first polynucleotide is immobilized at its 5' end to the surface of the microparticle and the second polynucleotide is hybridized to the 3' end of the first polynucleotide; and wherein the first polynucleotide comprises: (i) a 3' portion comprising a transposon end sequence, and (ii) the index domain; and wherein the population of microparticles comprises at least a plurality of index domains, and wherein the first polynucleotides on an individual microparticle share the same index domain.

Also presented herein is a method for sequencing a plurality of target DNA molecules, comprising: applying a plurality of target DNA to a solid support having transposome complexes immobilized thereon under conditions whereby the target DNA is fragmented by the transposome complexes; thereby producing an immobilized library of double-stranded fragments, wherein a first portion of each target DNA is attached to said solid support at a first location on said solid support and a second portion of each target DNA is attached to said solid support at a second location on said solid support; and mapping said immobilized library of double-stranded fragments to generate a set of locations that are linked by each target DNA; determining the sequences of said first and second portions of the target DNA; and correlating said set of locations to determine which first and second portions are linked by said target DNA and to determine the sequence of the target DNA molecules.

In some embodiments of the methods and compositions presented herein, the transposome complexes are present on the solid support at a density of at least $10^3$, $10^4$, $10^5$, $10^6$ complexes per $mm^2$. In some embodiments, the transposome complex comprises a hyperactive transposase, such as Tn5 transposase.

In some embodiments of the methods and compositions presented herein, the tag domain can comprise, for example, a region for cluster amplification. In some embodiments, the tag domain can comprise a region for priming a sequencing reaction.

In some embodiments of the methods and compositions presented herein, the solid support can comprise, for example, microparticles, a patterned surface, wells and the like. In some embodiments, the transposome complexes are randomly distributed upon the solid support. In some embodiments, the transposome complexes are distributed on a patterned surface.

The details of one or more embodiments are set forth in the accompanying drawings and the description below. Other features, objects, and advantages will be apparent from the description and drawings, and from the claims.

BRIEF DESCRIPTION OF THE DRAWINGS

FIG. 1b shows the general concept according to one embodiment.

FIG. 2b is a schematic with the resulting bridge redrawn to clarify the nature of the resulting bridge.

In FIG. 4a, only one form of surface bound transposome (e.g. P5 transposome) is present, resulting in bridges having the same tag sequence at each end. Additional transposomes are added to further fragment the bridge structures and incorporate an additional tag sequence (P7).

FIG. 4b shows amplification to generate pairs of clusters resulting from each transposome stump which represent two adjacent fragments in the original intact DNA sample (FIG. 4b).

FIGS. 5a, 5b, 5c and 5d illustrate different methods for assembling surface bound transposome complexes. FIG. 5a shows one embodiment of this method for assembling the surface bound transposome complexes. FIG. 5b shows transposome complexes are assembled in solution and immobilizing comprises a further step of ligating the first polynucleotide to an immobilized oligonucleotide coupled to the solid support. FIG. 5c shows a transposome dimer is assembled by hybridizing a looped oligonucleotide to an immobilized first polynucleotide. FIG. 5d shows transposome complexes can be assembled on a standard paired end flow cell with amplification primers immobilized thereto.

FIG. 6a sets forth the design for an experiment set forth as Example 1. FIG. 6b sets forth the design for an experiment set forth as Example 1.

FIG. 7 sets forth representative data obtained in an experiment conducted according to the design set forth in Example 1.

FIG. 8 sets forth representative data obtained in an experiment conducted according to the design set forth in Example 1.

FIG. 18a is an illustration of transposome assembly as described in Example 3.

FIG. 18b sets forth results using transposome assembly as described in Example 3.

DETAILED DESCRIPTION

Figure 1A:
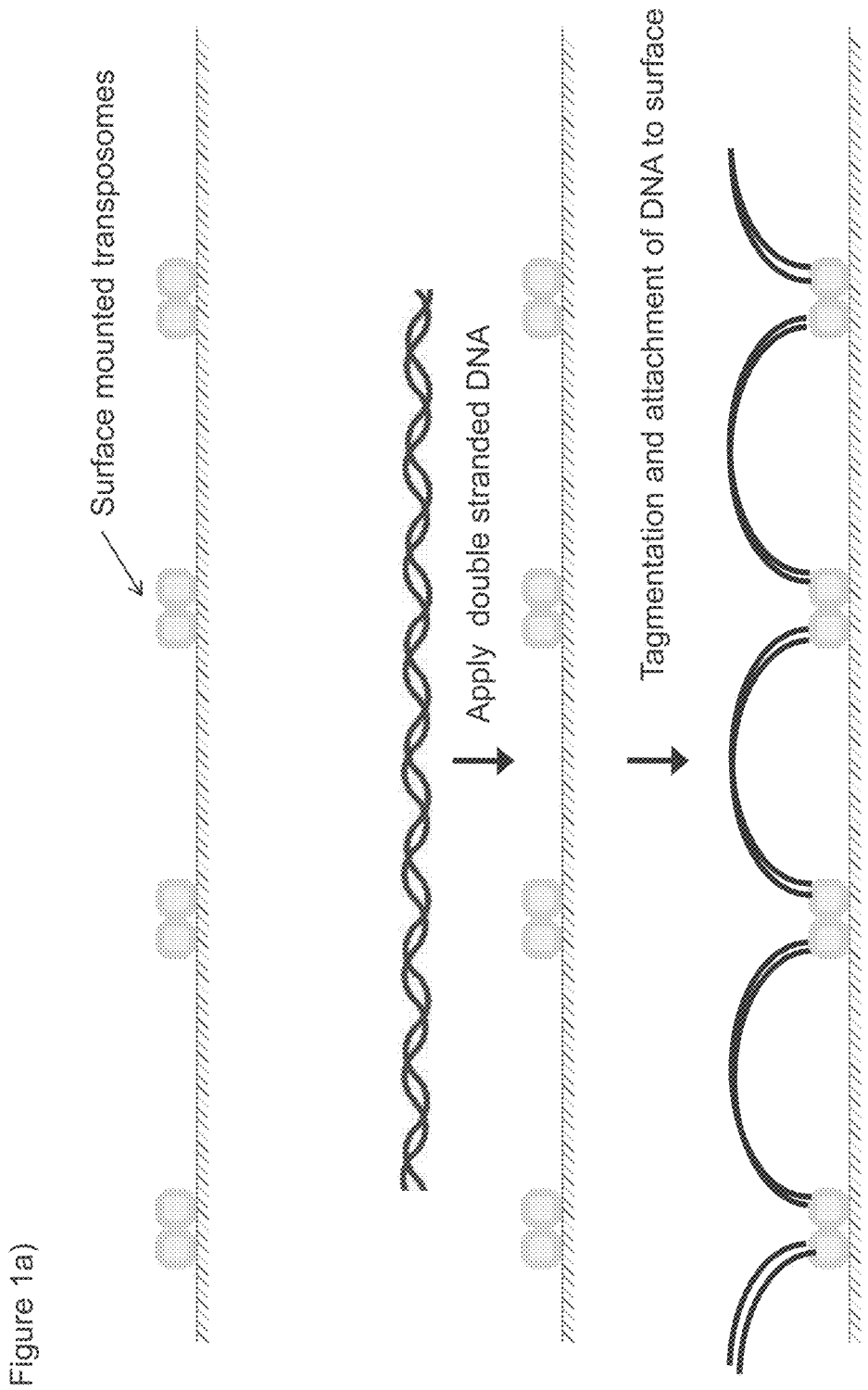
FIG. 1a shows the general concept according to one embodiment.

Current protocols for sequencing nucleic acid samples routinely employ a sample preparation process that converts DNA or RNA into a library of templates. These methods can result in loss of DNA sample and often require expensive instruments for fragmentation. In addition, the sample preparation methods are often difficult, tedious, and inefficient.

In standard sample preparation methods, each template contains an adaptor at either end of the insert and often a number of steps are required to both modify the DNA or RNA and to purify the desired products of the modification reactions. These steps are performed in solution prior to the addition of the adapted fragments to a flowcell where they are coupled to the surface by a primer extension reaction that copies the hybridized fragment onto the end of a primer covalently attached to the surface. These 'seeding' templates then give rise to monoclonal clusters of copied templates through several cycles of amplification.

The number of steps required to transform DNA into adaptor-modified templates in solution ready for cluster formation and sequencing can be minimized by the use of transposase mediated fragmentation and tagging. This process, referred to herein as 'tagmentation,' often involves the modification of DNA by a transposome complex comprising transposase enzyme complexed with adaptors comprising transposon end sequence. Tagmentation results in the simultaneous fragmentation of the DNA and ligation of the adaptors to the 5' ends of both strands of duplex fragments. Following a purification step to remove the transposase enzyme, additional sequences are added to the ends of the adapted fragments by PCR.

Solution-based tagmentation has drawbacks and requires several labor-intensive steps. Additionally, bias can be introduced during PCR amplification steps. The methods and compositions presented herein overcome those drawbacks and allow unbiased sample preparation, cluster formation and sequencing to occur on a single solid support with minimal requirements for sample manipulation or transfer.

The present disclosure relates to the surprising discovery that transposome complexes pre-coupled to the surface of a flowcell can effectively fragment, tag and immobilize intact DNA within the flowcell. In specific embodiments, one or more of the strands that comprise the transposome adaptors are attached to the surface of the flowcell via their 5' end. When intact DNA is pumped onto the flowcell, the tagmentation reaction occurs in the same manner as occurs in solution-based tagmentation reactions, but the resulting product fragments are physically attached to the surface of the flowcell by their ends. The transposome adaptor sequences can contain sequences that enable subsequent cluster generation and sequencing.

The methods and compositions presented herein provide several advantages over solution-based tagmentation methods. For example, purified, partially purified or even unpurified intact DNA template can be loaded directly onto a flowcell for generation of clusters, without prior sample preparation. In addition, the contiguity of sequence information in the original intact DNA can be physically preserved by the juxtaposition of tagmented fragments on the surface of the flowcell. As a further advantage, DNA is physically linked to the surface of the flowcell so purification of reagents following further manipulation of the DNA can be achieved by flow-through buffer exchange in the flowcell channel.

Tagmentation on a Solid Support

In accordance with the above, presented herein are methods of preparing an immobilized library of tagged DNA fragments. In some embodiments, the methods can comprise: (a) providing a solid support having transposome complexes immobilized thereon, wherein the transposome complexes comprise a transposase bound to a first polynucleotide, the first polynucleotide comprising (i) a 3' portion comprising a transposon end sequence, and (ii) a first tag comprising a first tag domain; and (b) applying a target DNA to the solid support under conditions whereby the target DNA is fragmented by the transposome complexes, and the 3' transposon end sequence of the first polynucleotide is transferred to a 5' end of at least one strand of the fragments; thereby producing an immobilized library of double-stranded fragments wherein at least one strand is 5'-tagged with the first tag.

As used herein, the term "transposome complex" refers generally to a transposase enzyme non-covalently bound to a double stranded nucleic acid. For example, the complex can be a transposase enzyme preincubated with double-stranded transposon DNA under conditions that support non-covalent complex formation. Double-stranded transposon DNA can include, without limitation, Tn5 DNA, a portion of Tn5 DNA, a transposon end composition, a mixture of transposon end compositions or other double-stranded DNAs capable of interacting with a transposase such as the hyperactive Tn5 transposase.

A "transposase" means an enzyme that is capable of forming a functional complex with a transposon end-containing composition (e.g., transposons, transposon ends, transposon end compositions) and catalyzing insertion or transposition of the transposon end-containing composition into the double-stranded target DNA with which it is incubated, for example, in an in vitro transposition reaction. A transposase as presented herein can also include integrases from retrotransposons and retroviruses. Transposases, transposomes and transposome complexes are generally known to those of skill in the art, as exemplified by the disclosure of US 2010/0120098, the content of which is incorporated herein by reference in its entirety. Although many embodiments described herein refer to Tn5 transposase and/or hyperactive Tn5 transposase, it will be appreciated that any transposition system that is capable of inserting a transposon end with sufficient efficiency to 5'-tag and fragment a target DNA for its intended purpose can be used in the present invention. In particular embodiments, a preferred transposition system is capable of inserting the transposon end in a random or in an almost random manner to 5'-tag and fragment the target DNA.

The term "transposon end" refers to a double-stranded nucleic acid DNA that exhibits only the nucleotide sequences (the "transposon end sequences") that are necessary to form the complex with the transposase or integrase enzyme that is functional in an in vitro transposition reaction. In some embodiments, a transposon end is capable of forming a functional complex with the transposase in a transposition reaction. As non-limiting examples, transposon ends can include the 19-bp outer end ("OE") transposon end, inner end ("IE") transposon end, or "mosaic end" ("ME") transposon end recognized by a wild-type or mutant Tn5 transposase, or the R1 and R2 transposon end as set forth in the disclosure of US 2010/0120098, the content of which is incorporated herein by reference in its entirety. Transposon ends can comprise any nucleic acid or nucleic acid analogue suitable for forming a functional complex with the transposase or integrase enzyme in an in vitro transposition reaction. For example, the transposon end can comprise DNA, RNA, modified bases, non-natural bases, modified backbone, and can comprise nicks in one or both strands. Although the term "DNA" is used throughout the present disclosure in connection with the composition of transposon ends, it should be understood that any suitable nucleic acid or nucleic acid analogue can be utilized in a transposon end.

The term "transferred strand" refers to the transferred portion of both transposon ends. Similarly, the term "non-transferred strand" refers to the non-transferred portion of both "transposon ends." The 3'-end of a transferred strand is joined or transferred to target DNA in an in vitro transposition reaction. The non-transferred strand, which exhibits a transposon end sequence that is complementary to the transferred transposon end sequence, is not joined or transferred to the target DNA in an in vitro transposition reaction.

In some embodiments, the transferred strand and non-transferred strand are covalently joined. For example, in some embodiments, the transferred and non-transferred strand sequences are provided on a single oligonucleotide, e.g., in a hairpin configuration. As such, although the free end of the non-transferred strand is not joined to the target DNA directly by the transposition reaction, the non-transferred strand becomes attached to the DNA fragment indirectly, because the non-transferred strand is linked to the transferred strand by the loop of the hairpin structure. Additional examples of transposome structure and methods of preparing and using transposomes can be found in the disclosure of US 2010/0120098, the content of which is incorporated herein by reference in its entirety.

The terms "tag" and "tag domain" as used herein refer to a portion or domain of a polynucleotide that exhibits a sequence for a desired intended purpose or application. Some embodiments presented herein include a transposome complex comprising a polynucleotide having a 3' portion comprising a transposon end sequence, and tag comprising a tag domain. Tag domains can comprise any sequence provided for any desired purpose. For example, in some embodiments, a tag domain comprises one or more restriction endonuclease recognition sites. In some embodiments, a tag domain comprises one or more regions suitable for hybridization with a primer for a cluster amplification reaction. In some embodiments, a tag domain comprises one or more regions suitable for hybridization with a primer for a sequencing reaction. It will be appreciated that any other suitable feature can be incorporated into a tag domain. In some embodiments, the tag domain comprises a sequence having a length between 5 and 200 bp. In some embodiments, the tag domain comprises a sequence having a length between 10 and 100 bp. In some embodiments, the tag domain comprises a sequence having a length between 20 and 50 bp. In some embodiments, the tag domain comprises a sequence having a length between 5, 6, 7, 8, 9, 10, 20, 30, 40, 50, 60, 70, 80, 90, 100, 150 and 200 bp.

In the methods and compositions presented herein, transposome complexes are immobilized to the solid support. In some embodiments, the transposome complexes are immobilized to the support via one or more polynucleotides, such as a polynucleotide comprising a transposon end sequence. In some embodiments, the transposome complex may be immobilized via a linker molecule coupling the transposase enzyme to the solid support. In some embodiments, both the transposase enzyme and the polynucleotide are immobilized to the solid support. When referring to immobilization of molecules (e.g. nucleic acids) to a solid support, the terms "immobilized" and "attached" are used interchangeably herein and both terms are intended to encompass direct or indirect, covalent or non-covalent attachment, unless indicated otherwise, either explicitly or by context. In certain embodiments of the invention covalent attachment may be preferred, but generally all that is required is that the molecules (e.g. nucleic acids) remain immobilized or attached to the support under the conditions in which it is intended to use the support, for example in applications requiring nucleic acid amplification and/or sequencing.

Certain embodiments of the invention may make use of solid supports comprised of an inert substrate or matrix (e.g. glass slides, polymer beads etc.) which has been functionalized, for example by application of a layer or coating of an intermediate material comprising reactive groups which permit covalent attachment to biomolecules, such as polynucleotides. Examples of such supports include, but are not limited to, polyacrylamide hydrogels supported on an inert substrate such as glass, particularly polyacrylamide hydrogels as described in WO 2005/065814 and US 2008/0280773, the contents of which are incorporated herein in their entirety by reference. In such embodiments, the biomolecules (e.g. polynucleotides) may be directly covalently attached to the intermediate material (e.g. the hydrogel) but the intermediate material may itself be non-covalently attached to the substrate or matrix (e.g. the glass substrate). The term "covalent attachment to a solid support" is to be interpreted accordingly as encompassing this type of arrangement.

The terms "solid surface," "solid support" and other grammatical equivalents herein refer to any material that is appropriate for or can be modified to be appropriate for the attachment of the transposome complexes. As will be appreciated by those in the art, the number of possible substrates is very large. Possible substrates include, but are not limited to, glass and modified or functionalized glass, plastics (including acrylics, polystyrene and copolymers of styrene and other materials, polypropylene, polyethylene, polybutylene, polyurethanes, Teflon", etc.), polysaccharides, nylon or nitrocellulose, ceramics, resins, silica or silica-based materials including silicon and modified silicon, carbon, metals, inorganic glasses, plastics, optical fiber bundles, and a variety of other polymers. Particularly useful solid supports and solid surfaces for some embodiments are located within a flow cell apparatus. Exemplary flow cells are set forth in further detail below.

In some embodiments, the solid support comprises a patterned surface suitable for immobilization of transposome complexes in an ordered pattern. A "patterned surface" refers to an arrangement of different regions in or on an exposed layer of a solid support. For example, one or more of the regions can be features where one or more transposome complexes are present. The features can be separated by interstitial regions where transposome complexes are not present. In some embodiments, the pattern can be an x-y format of features that are in rows and columns. In some embodiments, the pattern can be a repeating arrangement of features and/or interstitial regions. In some embodiments, the pattern can be a random arrangement of features and/or interstitial regions. In some embodiments, the transposome complexes are randomly distributed upon the solid support. In some embodiments, the transposome complexes are distributed on a patterned surface. Exemplary patterned surfaces that can be used in the methods and compositions set forth herein are described in U.S. Ser. No. 13/661,524 or US Pat. App. Publ. No. 2012/0316086 A1, each of which is incorporated herein by reference.

In some embodiments, the solid support comprises an array of wells or depressions in a surface. This may be fabricated as is generally known in the art using a variety of techniques, including, but not limited to, photolithography, stamping techniques, molding techniques and microetching techniques. As will be appreciated by those in the art, the technique used will depend on the composition and shape of the array substrate.

The composition and geometry of the solid support can vary with its use. In some embodiments, the solid support is a planar structure such as a slide, chip, microchip and/or array. As such, the surface of a substrate can be in the form of a planar layer. In some embodiments, the solid support comprises one or more surfaces of a flowcell. The term "flowcell" as used herein refers to a chamber comprising a solid surface across which one or more fluid reagents can be flowed. Examples of flowcells and related fluidic systems and detection platforms that can be readily used in the methods of the present disclosure are described, for example, in Bentley et al., Nature 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082, each of which is incorporated herein by reference.

In some embodiments, the solid support or its surface is non-planar, such as the inner or outer surface of a tube or vessel. In some embodiments, the solid support comprises microspheres or beads. By "microspheres" or "beads" or "particles" or grammatical equivalents herein is meant small discrete particles. Suitable bead compositions include, but are not limited to, plastics, ceramics, glass, polystyrene, methylstyrene, acrylic polymers, paramagnetic materials, thoria sol, carbon graphite, titanium dioxide, latex or cross-linked dextrans such as Sepharose, cellulose, nylon, cross-linked micelles and teflon, as well as any other materials outlined herein for solid supports may all be used. "Microsphere Detection Guide" from Bangs Laboratories, Fishers Ind. is a helpful guide. In certain embodiments, the microspheres are magnetic microspheres or beads.

The beads need not be spherical; irregular particles may be used. Alternatively or additionally, the beads may be porous. The bead sizes range from nanometers, i.e. 100 nm, to millimeters, i.e. 1 mm, with beads from about 0.2 micron to about 200 microns being preferred, and from about 0.5 to about 5 micron being particularly preferred, although in some embodiments smaller or larger beads may be used.

FIGS. 1a and 1b generally illustrate the method according to one embodiment. A solid support coated with grafted oligonucleotides is shown, some of which contain the ME sequences, will form active transposome complexes that are physically coupled to the solid support in the presence of Tn5. The density of these surface bound transposomes can be modulated by varying the density of the grafted oligonucleotides containing the ME sequence or by the amount of transposase added to the solid support. For example, in some embodiments, the transposome complexes are present on the solid support at a density of at least $10^3$, $10^4$, $10^5$, or at least $10^6$ complexes per $mm^2$.

When double stranded DNA is added to the solid support, the transposome complexes will tagment added DNA, thus generating ds fragments coupled at both ends to the surface. In some embodiments, the length of bridged fragments can be varied by changing the density of the transposome complexes on the surface. In certain embodiments, the length of the resulting bridged fragments is less than 100 bp, 200 bp, 300 bp, 400 bp, 500 bp, 600 bp, 700 bp, 800 bp, 900 bp, 1000 bp, 1100 bp, 1200 bp, 1300 bp, 1400 bp, 1500 bp, 1600 bp, 1700 bp, 1800 bp, 1900 bp, 2000 bp, 2100 bp, 2200 bp, 2300 bp, 2400 bp, 2500 bp, 2600 bp, 2700 bp, 2800 bp, 2900 bp, 3000 bp, 3100 bp, 3200 bp, 3300 bp, 3400 bp, 3500 bp, 3600 bp, 3700 bp, 3800 bp, 3900 bp, 4000 bp, 4100 bp, 4200 bp, 4300 bp, 4400 bp, 4500 bp, 4600 bp, 4700 bp, 4800 bp, 4900 bp, 5000 bp, 10000 bp, 30000 bp or less than 100,000 bp. In such embodiments, the bridged fragments can then be amplified into clusters using standard cluster chemistry, as exemplified by the disclosure of U.S. Pat. Nos. 7,985,565 and 7,115,400, the contents of each of which is incorporated herein by reference in its entirety.

In some embodiments, the length of the templates is longer than what can be suitably amplified using standard cluster chemistry. For example, in some embodiments, the length of templates is longer than 100 bp, 200 bp, 300 bp, 400 bp, 500 bp, 600 bp, 700 bp, 800 bp, 900 bp, 1000 bp, 1100 bp, 1200 bp, 1300 bp, 1400 bp, 1500 bp, 1600 bp, 1700 bp, 1800 bp, 1900 bp, 2000 bp, 2100 bp, 2200 bp, 2300 bp, 2400 bp, 2500 bp, 2600 bp, 2700 bp, 2800 bp, 2900 bp, 3000 bp, 3100 bp, 3200 bp, 3300 bp, 3400 bp, 3500 bp, 3600 bp, 3700 bp, 3800 bp, 3900 bp, 4000 bp, 4100 bp, 4200 bp, 4300 bp, 4400 bp, 4500 bp, 4600 bp, 4700 bp, 4800 bp, 4900 bp, 5000 bp, 10000 bp, 30000 bp or longer than 100,000 bp. In such embodiments, then a second tagmentation reaction can be performed by adding transposomes from solution that further fragment the bridges, as illustrated, for example, in FIG. 4a. The second tagmentation reaction can thus remove the internal span of the bridges, leaving short stumps anchored to the surface that can converted into clusters ready for further sequencing steps. In particular embodiments, the length of the template can be within a range defined by an upper and lower limit selected from those exemplified above.

In certain embodiments, prior to cluster generation, the DNA immobilized by surface tagmentation can imaged. For example, the immobilized DNA can be stained with an interchelating dye and imaged to preserve a record of the position of the backbone of the DNA molecule on the surface. Following cluster generation and sequencing, the coordinates of clusters can be associated with their position on the original backbone, thus assisting in alignment of reads along a molecule and genome assembly.

In some embodiments, the step of applying a target DNA comprises adding a biological sample to said solid support. The biological sample can be any type that comprises DNA and which can be deposited onto the solid surface for tagmentation. For example, the sample can comprise DNA in a variety of states of purification, including purified DNA. However, the sample need not be completely purified, and can comprise, for example, DNA mixed with protein, other nucleic acid species, other cellular components and/or any other contaminant. As demonstrated in Example 2 below, in some embodiments, the biological sample comprises a mixture of DNA, protein, other nucleic acid species, other cellular components and/or any other contaminant present in approximately the same proportion as found in vivo. For example, in some embodiments, the components are found in the same proportion as found in an intact cell. In some embodiments, the biological sample has a 260/280 ratio of less than 2.0, 1.9, 1.8, 1.7, 1.6, 1.5, 1.4, 1.3, 1.2, 1.1, 1.0, 0.9, 0.8, 0.7, or less than 0.60. In some embodiments, the biological sample has a 260/280 ratio of at least 2.0, 1.9, 1.8, 1.7, 1.6, 1.5, 1.4, 1.3, 1.2, 1.1, 1.0, 0.9, 0.8, 0.7, or at least 0.60. Because the methods provided herein allow DNA to be bound to a solid support, other contaminants can be removed merely by washing the solid support after surface bound tagmentation occurs. The biological sample can comprise, for example, a crude cell lysate or whole cells. For example, a crude cell lysate that is applied to a solid support in a method set forth herein, need not have been subjected to one or more of the separation steps that are traditionally used to isolate nucleic acids from other cellular components. Exemplary separation steps are set forth in Maniatis et al., Molecular Cloning: A Laboratory Manual, 2d Edition, 1989, and Short Protocols in Molecular Biology, ed. Ausubel, et al, hereby incorporated by reference.

Thus, in some embodiments, the biological sample can comprise, for example, blood, plasma, serum, lymph, mucus, sputum, urine, semen, cerebrospinal fluid, bronchial aspirate, feces, and macerated tissue, or a lysate thereof, or any other biological specimen comprising DNA. One advantage of the methods and compositions presented herein that a biological sample can be added to the flowcell and subsequent lysis and purification steps can all occur in the flowcell without further transfer or handling steps, simply by flowing the necessary reagents into the flowcell. Examples 1 and 2 below demonstrate successful application of crude cell lysates to the methods and compositions provided herein.

Figure 2A:
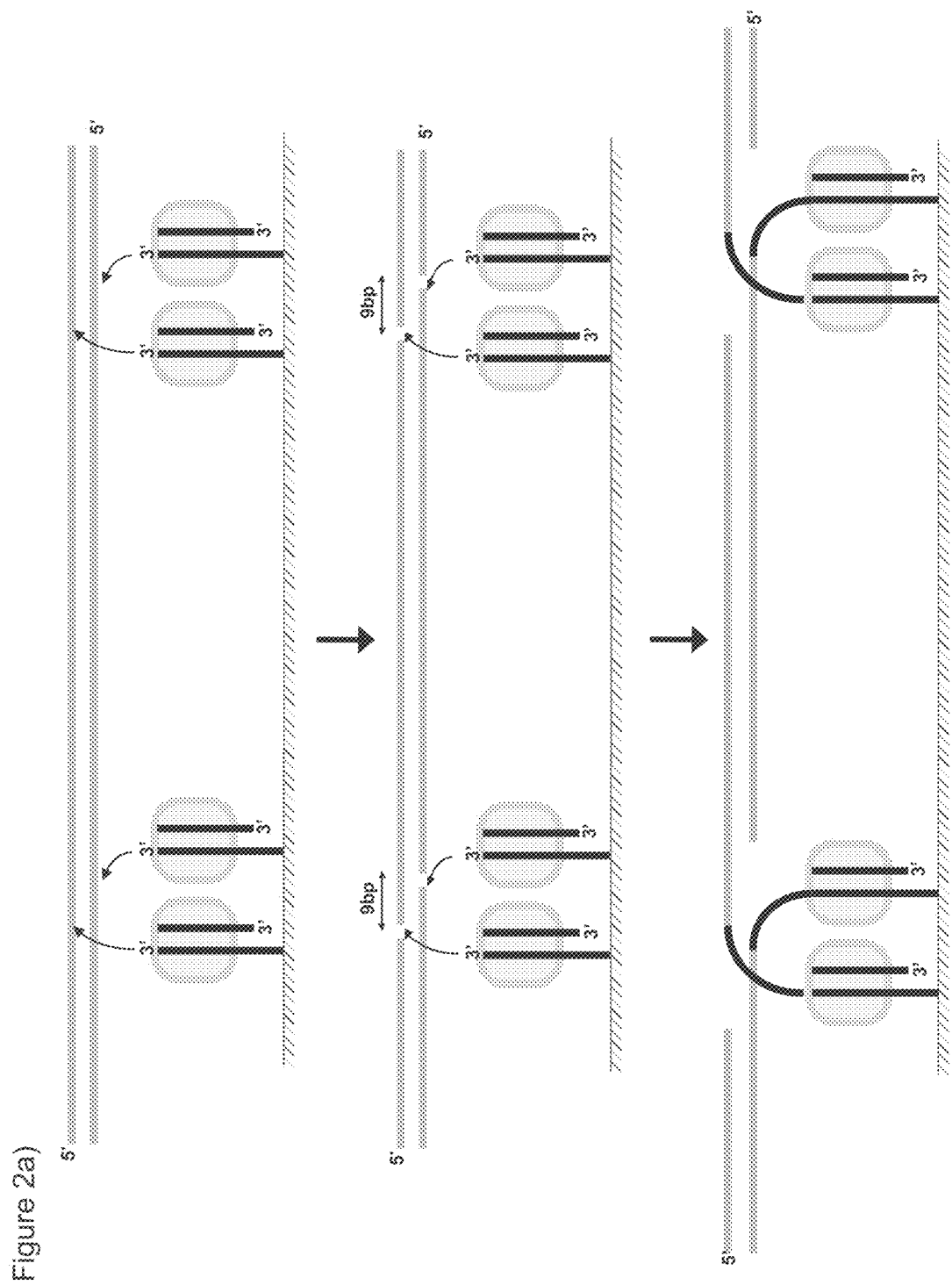
FIG. 2a is a schematic illustrating a tagmentation reaction.

FIGS. 2a and 2b further illustrate the tagmentation reaction according to one embodiment. As shown in FIG. 2a, transposomes comprise a dimer of Tn5 with each monomer binding a double stranded molecule, i.e. the ME adaptor. One strand of the ME adaptor is covalently attached to the surface of a flowcell. Transposomes bind target DNA and generate two nicks in the DNA backbone, 9 bases apart on either strand. Although FIG. 2a shows a 9 bp gap between nicks, in other embodiments, the transposome can generate a gap of 7, 8, 9, 10, 11, or 12 bp between nicks. Only one of the two strands of each ME adaptor is ligated to the 5' strand at each nick position. This strand 'the transferred strand' is grafted to the surface of the flowcell via its 5' end. The resulting bridge of the surface tagmentation is redrawn in FIG. 2b to clarify the nature of the resulting bridge.

Figure 3A:
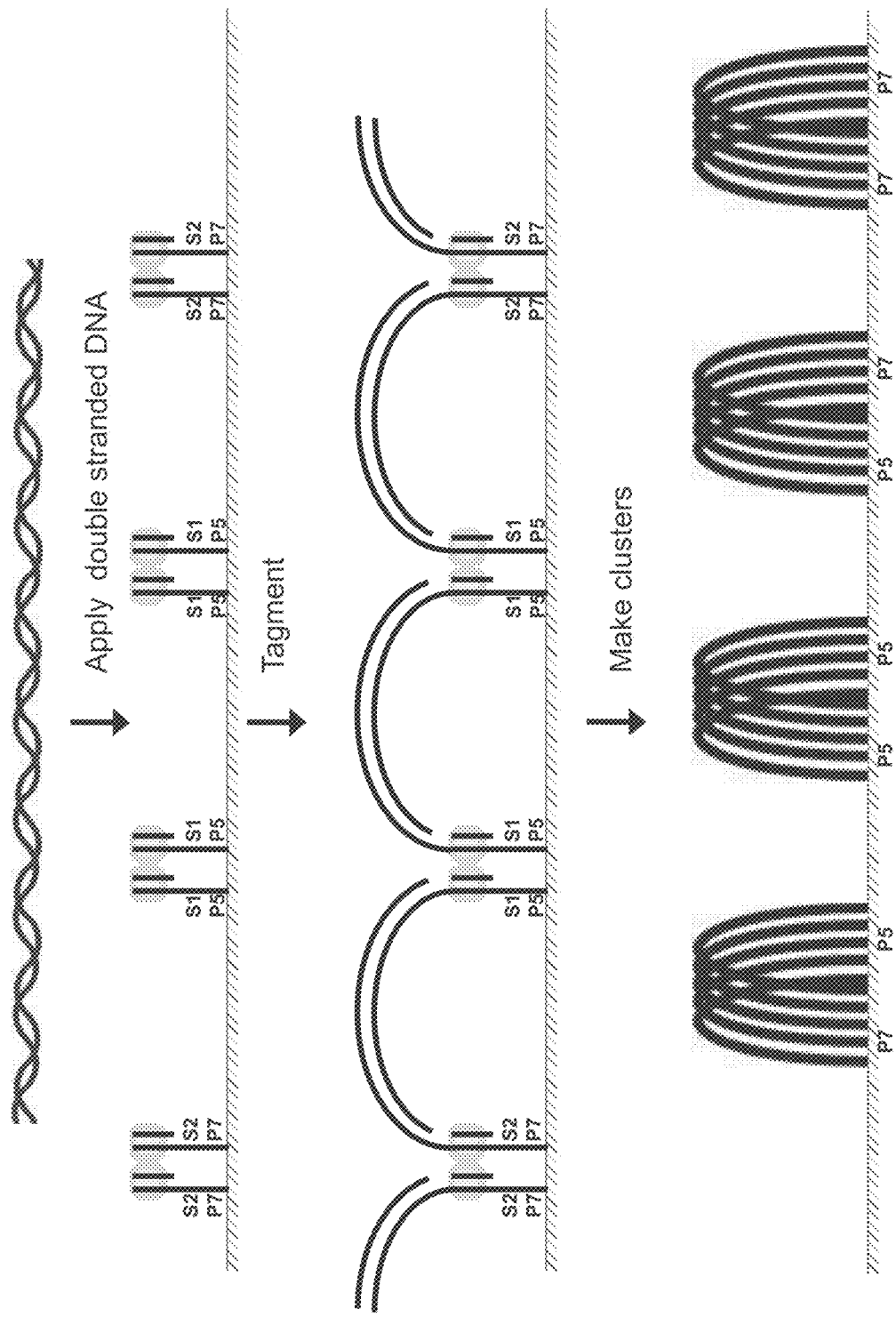
FIG. 3a illustrates an embodiment where two forms of transposome are assembled on the surface of a flowcell. Addition of DNA to the flowcell results in tagmentation and coupling of the DNA to the transposomes. Also shown in FIG. 3a are different types of resulting clusters: P7:P7, P5:P5, and P5:P7 clusters. 3b illustrates an embodiment where two forms of transposome are assembled on the surface of a flowcell.
Figure 3B:
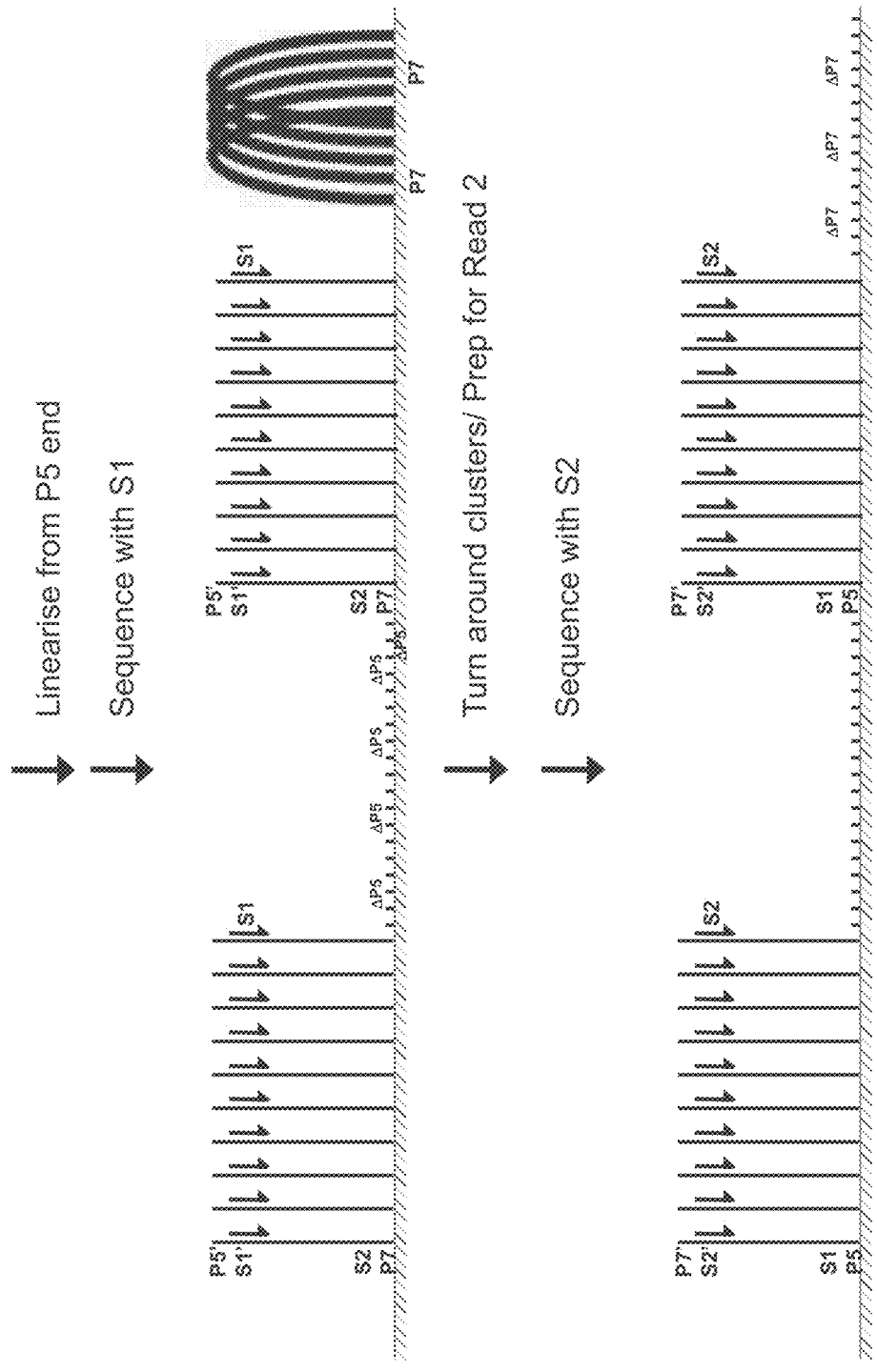

FIGS. 3a and 3b illustrate an example of the invention put into practice. Two forms of transposome are assembled on the surface of a flowcell. The first form comprises a P7 transposome in which the 'transfer strand' of the ME adaptor comprises an extended oligonucleotide sequence linking the transposome to the surface including an amplification domain (P7) and a sequencing primer (S2). The second form comprises a P5 transposome in which the 'transfer strand' of the ME adaptor comprises an extended oligonucleotide sequence linking the transposome to the surface including an amplification domain (P5) and a sequencing primer (S1). Addition of DNA to the flowcell results in tagmentation and coupling of the DNA to the transposomes. Three types of bridges result: P5-P5, P7-P7 and P5-P7. Following cluster formation and linearization (FIG. 3b), either P5-P5 or P7-P7 clusters are removed (depending on linearization). As shown in FIG. 3b, if linearization happens via P5, then only the P5-P7 and P7-P7 bridges remain. P7-P7 clusters are not linearized by this reaction and therefore will not sequence. P7-P7 clusters are subsequently removed during Read 2 linearization for sequencing.

The method presented herein can further comprise an additional step of providing transposome complexes in solution and contacting the solution-phase transposome complexes with the immobilized fragments under conditions whereby the target DNA is fragmented by the transposome complexes solution; thereby obtaining immobilized nucleic acid fragments having one end in solution. In some embodiments, the transposome complexes in solution can comprise a second tag, such that the method generates immobilized nucleic acid fragments having a second tag, the second tag in solution. The first and second tags can be different or the same.

In some embodiments, one form of surface bound transposome is predominantly present on the solid support. For example, in some embodiments, at least 50%, 55%, 60%, 65%, 70%, 75%, 80%, 85%, 90%, 95%, 96%, 97%, 98%, or at least 99% of the tags present on said solid support comprise the same tag domain. In such embodiments, after an initial tagmentation reaction with surface bound transposomes, at least 50%, 55%, 60%, 65%, 70%, 75%, 80%, 85%, 90%, 95%, 96%, 97%, 98%, or at least 99% of the bridge structures comprise the same tag domain at each end of the bridge. A second tagmentation reaction can be performed by adding transposomes from solution that further fragment the bridges. In some embodiments, most or all of the solution phase transposomes comprise a tag domain that differs from the tag domain present on the bridge structures generated in the first tagmentation reaction. For example, in some embodiments, at least 50%, 55%, 60%, 65%, 70%, 75%, 80%, 85%, 90%, 95%, 96%, 97%, 98%, or at least 99% of the tags present in the solution phase transposomes comprise the a tag domain that differs from the tag domain present on the bridge structures generated in the first tagmentation reaction.

Figure 4A:
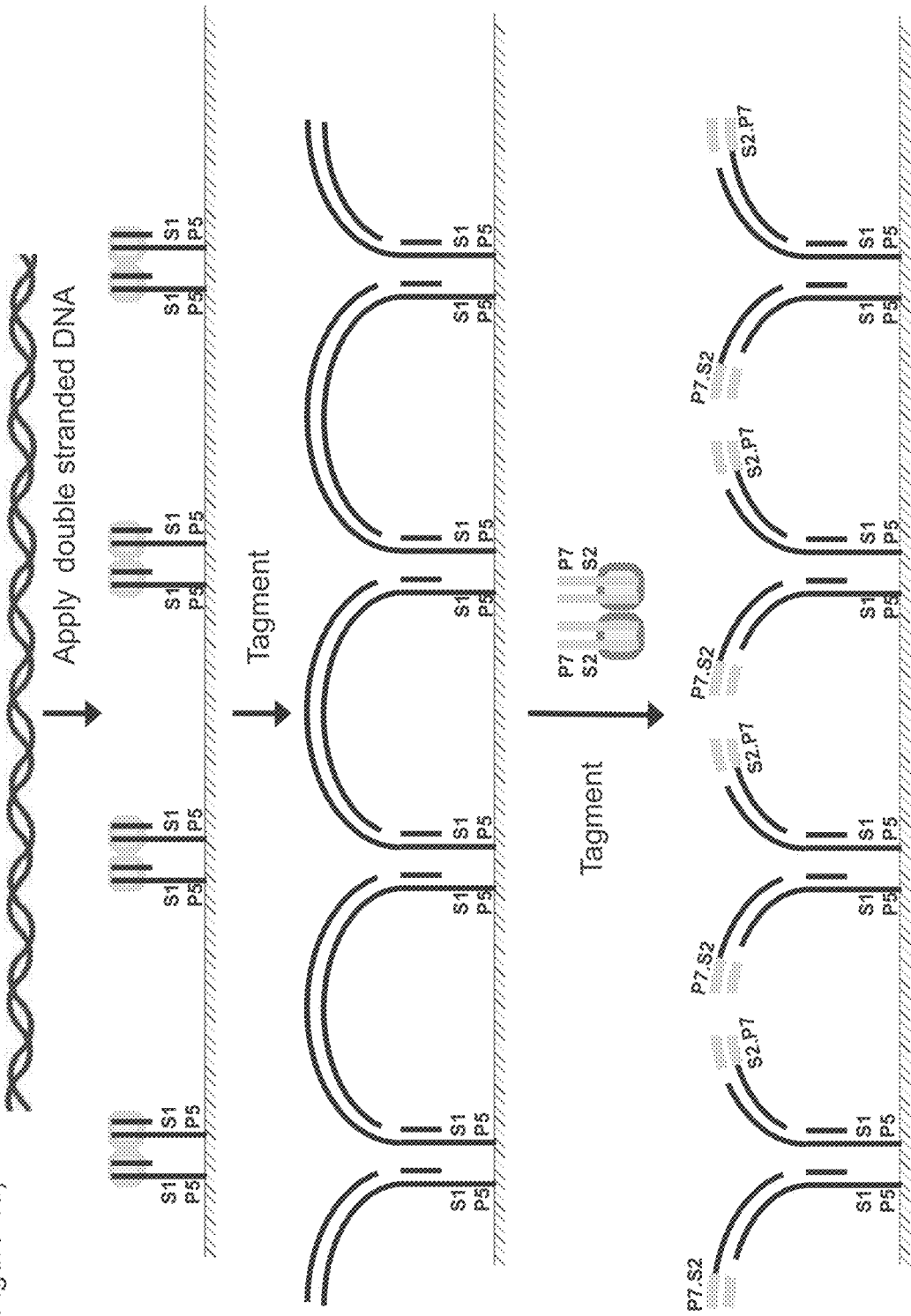
FIG. 4a illustrates another embodiment.

FIGS. 4a and 4b illustrate this embodiment. The solid support shown in FIG. 4a comprises only surface bound transposome comprising a single type of tag sequence (e.g. P5 transposome). In this instance, all tagmented bridges are P5-P5 bridges. A P7 transposome is added from solution and tagments into the bridges making all surface bound molecules P5-P7 templates. The surface bound fragments can be subsequently converted into clusters (see, for example, FIG. 4b). Furthermore, a pair of clusters will result from each transposome stump which represent the two adjacent fragments in the original intact DNA sample (FIG. 4b).

Also presented herein are solid supports having a library of tagged DNA fragments immobilized thereon prepared according to the above methods.

Physical Maps of Immobilized Polynucleotide Molecules

Also presented herein are methods of generating a physical map of immobilized polynucleotides. The methods can advantageously be exploited to identify clusters likely to contain linked sequences (i.e., the first and second portions from the same target polynucleotide molecule). The relative proximity of any two clusters resulting from an immobilized polynucleotide thus provides information useful for alignment of sequence information obtained from the two clusters. Specifically, the distance between any two given clusters on a solid surface is positively correlated with the probability that the two clusters are from the same target polynucleotide molecule, as described in greater detail in WO 2012/025250, which is incorporated herein by reference in its entirety.

As an example, in some embodiments, long dsDNA molecules stretching out over the surface of a flowcell are tagmented in situ, resulting in a line of connected dsDNA bridges across the surface of the flowcell. Further, a physical map of the immobilized DNA can then be generated. The physical map thus correlates the physical relationship of clusters after immobilized DNA is amplified. Specifically, the physical map is used to calculate the probability that sequence data obtained from any two clusters are linked, as described in the incorporated materials of WO 2012/025250.

In some embodiments, the physical map is generated by imaging the DNA to establish the location of the immobilized DNA molecules across a solid surface. In some embodiments, the immobilized DNA is imaged by adding an imaging agent to the solid support and detecting a signal from the imaging agent. In some embodiments, the imaging agent is a detectable label. Suitable detectable labels, include, but are not limited to, protons, haptens, radionuclides, enzymes, fluorescent labels, chemiluminescent labels, and/or chromogenic agents. For example, in some embodiments, the imaging agent is an intercalating dye or non-intercalating DNA binding agent. Any suitable intercalating dye or non-intercalating DNA binding agent as are known in the art can be used, including, but not limited to those set forth in U.S. 2012/0282617, which is incorporated herein by reference in its entirety.

In some embodiments, the immobilized double stranded fragments are further fragmented to liberate a free end (see FIG. 4a) prior to cluster generation (FIG. 4b). Cleaving bridged structures can be performed using any suitable methodology as is known in the art, as exemplified by the incorporated materials of WO 2012/025250. For example, cleavage can occur by incorporation of a modified nucleotide, such as uracil as described in WO 2012/025250, by incorporation of a restriction endonuclease site, or by applying solution-phase transposome complexes to the bridged DNA structures, as described elsewhere herein.

In certain embodiments, a plurality of target DNA molecules is flowed onto a flowcell comprising a plurality of nano-channels, the nano-channel having a plurality of transposome complexes immobilized thereto. As used herein, the term nano-channel refers to a narrow channel into which a long linear DNA molecule is flown. In some embodiments, no more than 1, 2, 3, 4, 5, 6, 7, 8, 9, 10, 11, 12, 13, 14, 15, 16, 17, 18, 19, 20, 30, 40, 50, 60 70, 80, 90, 100, 200, 300, 400, 500, 600, 700, 800, 900 or no more than 1000 individual long strands of target DNA are flowed into each nano-channel. In some embodiments the individual nano-channels are separated by a physical barrier which prevents individual long strands of target DNA from interacting with multiple nano-channels. In some embodiments, the solid support comprises at least 10, 50, 100, 200, 500, 1000, 3000, 5000, 10000, 30000, 50000, 80000 or at least 100000 nano-channels. In some embodiments, transposomes bound to the surface of a nano-channel tagment the DNA. Contiguity mapping can then be performed, for example, by following the clusters down the length of one of these channels. In some embodiments, the long strand of target DNA can be at least 0.1 kb, 1 kb, 2 kb, 3 kb, 4 kb, 5 kb, 6 kb, 7 kb, 8 kb, 9 kb, 10 kb, 15 kb, 20 kb, 25 kb, 30 kb, 35 kb, 40 kb, 45 kb, 50 kb, 55 kb, 60 kb, 65 kb, 70 kb, 75 kb, 80 kb, 85 kb, 90 kb, 95 kb, 100 kb, 150 kb, 200 kb, 250 kb, 300 kb, 350 kb, 400 kb, 450 kb, 500 kb, 550 kb, 600 kb, 650 kb, 700 kb, 750 kb, 800 kb, 850 kb, 900 kb, 950 kb, 1000 kb, 5000 kb, 10000 kb, 20000 kb, 30000 kb, or at least 50000 kb in length. In some embodiments, the long strand of target DNA is no more than 0.1 kb, 1 kb, 2 kb, 3 kb, 4 kb, 5 kb, 6 kb, 7 kb, 8 kb, 9 kb, 10 kb, 15 kb, 20 kb, 25 kb, 30 kb, 35 kb, 40 kb, 45 kb, 50 kb, 55 kb, 60 kb, 65 kb, 70 kb, 75 kb, 80 kb, 85 kb, 90 kb, 95 kb, 100 kb, 150 kb, 200 kb, 250 kb, 300 kb, 350 kb, 400 kb, 450 kb, 500 kb, 550 kb, 600 kb, 650 kb, 700 kb, 750 kb, 800 kb, 850 kb, 900 kb, 950 kb, or no more than 1000 kb in length. As an example, a flowcell having 1000 or more nano-channels with mapped immobilized tagmentation products in the nano-channels can be used to sequence the genome of an organism with short 'positioned' reads. In some embodiments, mapped immobilized tagmentation products in the nano-channels can be used resolve haplotypes. In some embodiments, mapped immobilized tagmentation products in the nano-channels can be used to resolve phasing issues.

Amplification and Sequencing Immobilized DNA Fragments

Amplification. The present disclosure further relates to amplification of the immobilized DNA fragments produced according to the methods provided herein. The immobilized DNA fragments produced by surface bound transposome mediated tagmentation can be amplified according to any suitable amplification methodology known in the art. In some embodiments, the immobilized DNA fragments are amplified on a solid support. In some embodiments, the solid support is the same solid support upon which the surface bound tagmentation occurs. In such embodiments, the methods and compositions provided herein allow sample preparation to proceed on the same solid support from the initial sample introduction step through amplification and optionally through a sequencing step.

For example, in some embodiments, the immobilized DNA fragments are amplified using cluster amplification methodologies as exemplified by the disclosures of U.S. Pat. Nos. 7,985,565 and 7,115,400, the contents of each of which is incorporated herein by reference in its entirety. The incorporated materials of U.S. Pat. Nos. 7,985,565 and 7,115,400 describe methods of solid-phase nucleic acid amplification which allow amplification products to be immobilized on a solid support in order to form arrays comprised of clusters or "colonies" of immobilized nucleic acid molecules. Each cluster or colony on such an array is formed from a plurality of identical immobilized polynucleotide strands and a plurality of identical immobilized complementary polynucleotide strands. The arrays so-formed are generally referred to herein as "clustered arrays". The products of solid-phase amplification reactions such as those described in U.S. Pat. Nos. 7,985,565 and 7,115,400 are so-called "bridged" structures formed by annealing of pairs of immobilized polynucleotide strands and immobilized complementary strands, both strands being immobilized on the solid support at the 5' end, preferably via a covalent attachment. Cluster amplification methodologies are examples of methods wherein an immobilized nucleic acid template is used to produce immobilized amplicons. Other suitable methodologies can also be used to produce immobilized amplicons from immobilized DNA fragments produced according to the methods provided herein. For example one or more clusters or colonies can be formed via solid-phase PCR whether one or both primers of each pair of amplification primers are immobilized.

In other embodiments, the immobilized DNA fragments are amplified in solution. For example, in some embodiments, the immobilized DNA fragments are cleaved or otherwise liberated from the solid support and amplification primers are then hybridized in solution to the liberated molecules. In other embodiments, amplification primers are hybridized to the immobilized DNA fragments for one or more initial amplification steps, followed by subsequent amplification steps in solution. Thus, in some embodiments an immobilized nucleic acid template can be used to produce solution-phase amplicons.

It will be appreciated that any of the amplification methodologies described herein or generally known in the art can be utilized with universal or target-specific primers to amplify immobilized DNA fragments. Suitable methods for amplification include, but are not limited to, the polymerase chain reaction (PCR), strand displacement amplification (SDA), transcription mediated amplification (TMA) and nucleic acid sequence based amplification (NASBA), as described in U.S. Pat. No. 8,003,354, which is incorporated herein by reference in its entirety. The above amplification methods can be employed to amplify one or more nucleic acids of interest. For example, PCR, including multiplex PCR, SDA, TMA, NASBA and the like can be utilized to amplify immobilized DNA fragments. In some embodiments, primers directed specifically to the nucleic acid of interest are included in the amplification reaction.

Other suitable methods for amplification of nucleic acids can include oligonucleotide extension and ligation, rolling circle amplification (RCA) (Lizardi et al., Nat. Genet. 19:225-232 (1998), which is incorporated herein by reference) and oligonucleotide ligation assay (OLA) (See generally U.S. Pat. Nos. 7,582,420, 5,185,243, 5,679,524 and 5,573,907; EP 0 320 308 B1; EP 0 336 731 B1; EP 0 439 182 B1; WO 90/01069; WO 89/12696; and WO 89/09835, all of which are incorporated by reference) technologies. It will be appreciated that these amplification methodologies can be designed to amplify immobilized DNA fragments. For example, in some embodiments, the amplification method can include ligation probe amplification or oligonucleotide ligation assay (OLA) reactions that contain primers directed specifically to the nucleic acid of interest. In some embodiments, the amplification method can include a primer extension-ligation reaction that contains primers directed specifically to the nucleic acid of interest. As a non-limiting example of primer extension and ligation primers that can be specifically designed to amplify a nucleic acid of interest, the amplification can include primers used for the GoldenGate assay (Illumina, Inc., San Diego, Calif.) as exemplified by U.S. Pat. Nos. 7,582,420 and 7,611,869, each of which is incorporated herein by reference in its entirety.

Exemplary isothermal amplification methods that can be used in a method of the present disclosure include, but are not limited to, Multiple Displacement Amplification (MDA) as exemplified by, for example Dean et al., Proc. Natl. Acad. Sci. USA 99:5261-66 (2002) or isothermal strand displacement nucleic acid amplification exemplified by, for example U.S. Pat. No. 6,214,587, each of which is incorporated herein by reference in its entirety. Other non-PCR-based methods that can be used in the present disclosure include, for example, strand displacement amplification (SDA) which is described in, for example Walker et al., Molecular Methods for Virus Detection, Academic Press, Inc., 1995; U.S. Pat. Nos. 5,455,166, and 5,130,238, and Walker et al., Nucl. Acids Res. 20:1691-96 (1992) or hyperbranched strand displacement amplification which is described in, for example Lage et al., Genome Research 13:294-307 (2003), each of which is incorporated herein by reference in its entirety. Isothermal amplification methods can be used with the strand-displacing Phi 29 polymerase or Bst DNA polymerase large fragment, 5'→3' exo⁻ for random primer amplification of genomic DNA. The use of these polymerases takes advantage of their high processivity and strand displacing activity. High processivity allows the polymerases to produce fragments that are 10-20 kb in length. As set forth above, smaller fragments can be produced under isothermal conditions using polymerases having low processivity and strand-displacing activity such as Klenow polymerase. Additional description of amplification reactions, conditions and components are set forth in detail in the disclosure of U.S. Pat. No. 7,670,810, which is incorporated herein by reference in its entirety.

Another nucleic acid amplification method that is useful in the present disclosure is Tagged PCR which uses a population of two-domain primers having a constant 5' region followed by a random 3' region as described, for example, in Grothues et al. Nucleic Acids Res. 21(5):1321-2 (1993), incorporated herein by reference in its entirety. The first rounds of amplification are carried out to allow a multitude of initiations on heat denatured DNA based on individual hybridization from the randomly-synthesized 3' region. Due to the nature of the 3' region, the sites of initiation are contemplated to be random throughout the genome. Thereafter, the unbound primers can be removed and further replication can take place using primers complementary to the constant 5' region.

Sequencing. The present disclosure further relates to sequencing of the immobilized DNA fragments produced according to the methods provided herein. The immobilized DNA fragments produced by surface bound transposome mediated tagmentation can be sequenced according to any suitable sequencing methodology, such as direct sequencing, including sequencing by synthesis, sequencing by ligation, sequencing by hybridization, nanopore sequencing and the like. In some embodiments, the immobilized DNA fragments are sequenced on a solid support. In some embodiments, the solid support for sequencing is the same solid support upon which the surface bound tagmentation occurs. In some embodiments, the solid support for sequencing is the same solid support upon which the amplification occurs.

One preferred sequencing methodology is sequencing-by-synthesis (SBS). In SBS, extension of a nucleic acid primer along a nucleic acid template (e.g. a target nucleic acid or amplicon thereof) is monitored to determine the sequence of nucleotides in the template. The underlying chemical process can be polymerization (e.g. as catalyzed by a polymerase enzyme). In a particular polymerase-based SBS embodiment, fluorescently labeled nucleotides are added to a primer (thereby extending the primer) in a template dependent fashion such that detection of the order and type of nucleotides added to the primer can be used to determine the sequence of the template.

Flow cells provide a convenient solid support for housing amplified DNA fragments produced by the methods of the present disclosure. One or more amplified DNA fragments in such a format can be subjected to an SBS or other detection technique that involves repeated delivery of reagents in cycles. For example, to initiate a first SBS cycle, one or more labeled nucleotides, DNA polymerase, etc., can be flowed into/through a flow cell that houses one or more amplified nucleic acid molecules. Those sites where primer extension causes a labeled nucleotide to be incorporated can be detected. Optionally, the nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for embodiments that use reversible termination, a deblocking reagent can be delivered to the flow cell (before or after detection occurs). Washes can be carried out between the various delivery steps. The cycle can then be repeated n times to extend the primer by n nucleotides, thereby detecting a sequence of length n. Exemplary SBS procedures, fluidic systems and detection platforms that can be readily adapted for use with amplicons produced by the methods of the present disclosure are described, for example, in Bentley et al., Nature 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082, each of which is incorporated herein by reference.

Other sequencing procedures that use cyclic reactions can be used, such as pyrosequencing. Pyrosequencing detects the release of inorganic pyrophosphate (PPi) as particular nucleotides are incorporated into a nascent nucleic acid strand (Ronaghi, et al., *Analytical Biochemistry* 242(1), 84-9 (1996); Ronaghi, *Genome Res.* 11(1), 3-11 (2001); Ronaghi et al. *Science* 281(5375), 363 (1998); U.S. Pat. Nos. 6,210, 891; 6,258,568 and 6,274,320, each of which is incorporated herein by reference). In pyrosequencing, released PPi can be detected by being immediately converted to adenosine triphosphate (ATP) by ATP sulfurylase, and the level of ATP generated can be detected via luciferase-produced photons. Thus, the sequencing reaction can be monitored via a luminescence detection system. Excitation radiation sources used for fluorescence based detection systems are not necessary for pyrosequencing procedures. Useful fluidic systems, detectors and procedures that can be adapted for application of pyrosequencing to amplicons produced according to the present disclosure are described, for example, in WIPO Pat. App. Ser. No. PCT/US11/57111, US 2005/0191698 A1, U.S. Pat. Nos. 7,595,883, and 7,244,559, each of which is incorporated herein by reference.

Some embodiments can utilize methods involving the real-time monitoring of DNA polymerase activity. For example, nucleotide incorporations can be detected through fluorescence resonance energy transfer (FRET) interactions between a fluorophore-bearing polymerase and γ-phosphate-labeled nucleotides, or with zeromode waveguides (ZMWs). Techniques and reagents for FRET-based sequencing are described, for example, in Levene et al. *Science* 299, 682-686 (2003); Lundquist et al. *Opt. Lett.* 33, 1026-1028 (2008); Korlach et al. *Proc. Natl. Acad. Sci. USA* 105, 1176-1181 (2008), the disclosures of which are incorporated herein by reference.

Some SBS embodiments include detection of a proton released upon incorporation of a nucleotide into an extension product. For example, sequencing based on detection of released protons can use an electrical detector and associated techniques that are commercially available from Ion Torrent (Guilford, Conn., a Life Technologies subsidiary) or sequencing methods and systems described in US 2009/0026082 A1; US 2009/0127589 A1; US 2010/0137143 A1; or US 2010/0282617 A1, each of which is incorporated herein by reference. Methods set forth herein for amplifying target nucleic acids using kinetic exclusion can be readily applied to substrates used for detecting protons. More specifically, methods set forth herein can be used to produce clonal populations of amplicons that are used to detect protons.

Another useful sequencing technique is nanopore sequencing (see, for example, Deamer et al. Trends Biotechnol. 18, 147-151 (2000); Deamer et al. Acc. Chem. Res. 35:817-825 (2002); Li et al. Nat. Mater. 2:611-615 (2003), the disclosures of which are incorporated herein by reference). In some nanopore embodiments, the target nucleic acid or individual nucleotides removed from a target nucleic acid pass through a nanopore. As the nucleic acid or nucleotide passes through the nanopore, each nucleotide type can be identified by measuring fluctuations in the electrical conductance of the pore. (U.S. Pat. No. 7,001,792; Soni et al. Clin. Chem. 53, 1996-2001 (2007); Healy, Nanomed. 2, 459-481 (2007); Cockroft et al. J. Am. Chem. Soc. 130, 818-820 (2008), the disclosures of which are incorporated herein by reference).

Exemplary methods for array-based expression and genotyping analysis that can be applied to detection according to the present disclosure are described in U.S. Pat. Nos. 7,582, 420; 6,890,741; 6,913,884 or 6,355,431 or US Pat. Pub. Nos. 2005/0053980 A1; 2009/0186349 A1 or US 2005/0181440 A1, each of which is incorporated herein by reference.

An advantage of the methods set forth herein is that they provide for rapid and efficient detection of a plurality of target nucleic acid in parallel. Accordingly the present disclosure provides integrated systems capable of preparing and detecting nucleic acids using techniques known in the art such as those exemplified above. Thus, an integrated system of the present disclosure can include fluidic components capable of delivering amplification reagents and/or sequencing reagents to one or more immobilized DNA fragments, the system comprising components such as pumps, valves, reservoirs, fluidic lines and the like. A flow cell can be configured and/or used in an integrated system for detection of target nucleic acids. Exemplary flow cells are described, for example, in US 2010/0111768 A1 and U.S. Ser. No. 13/273,666, each of which is incorporated herein by reference. As exemplified for flow cells, one or more of the fluidic components of an integrated system can be used for an amplification method and for a detection method. Taking a nucleic acid sequencing embodiment as an example, one or more of the fluidic components of an integrated system can be used for an amplification method set forth herein and for the delivery of sequencing reagents in a sequencing method such as those exemplified above. Alternatively, an integrated system can include separate fluidic systems to carry out amplification methods and to carry out detection methods. Examples of integrated sequencing systems that are capable of creating amplified nucleic acids and also determining the sequence of the nucleic acids include, without limitation, the MiSeq™ platform (Illumina, Inc., San Diego, Calif.) and devices described in U.S. Ser. No. 13/273,666, which is incorporated herein by reference.

Solid Supports with Immobilized Transposomes and Methods of Preparation

Other embodiments presented herein include solid supports, such as flowcells, having transposome complexes immobilized thereon. In certain embodiments, the transposome complexes comprise a transposase bound to a first polynucleotide, the polynucleotide comprising (i) a 3' portion comprising a transposon end sequence, and (ii) a first tag comprising a first tag domain. The density of these surface bound transposomes can vary. For example, in some embodiments, the transposome complexes are present on the solid support at a density of at least $10^3$, $10^4$, $10^5$, or at least $10^6$ complexes per $mm^2$.

Also presented herein are methods of generating a flow-cell for tagmentation. The methods can comprise, for example, immobilizing a plurality of transposome complexes to a solid support, the transposome complexes comprising a transposase bound to a first polynucleotide, the first polynucleotide comprising (i) a 3' portion comprising a transposon end sequence, and (ii) a first tag comprising a first tag domain.

Transposome complexes can be immobilized to a solid support in a variety of methods, which will be appreciated by one of skill in the art. In one embodiment, the method comprises providing a solid support having a plurality of first polynucleotides immobilized thereon, and contacting the solid support with transposase holoenzyme and a second polynucleotide, the second polynucleotide comprising a region complementary to the transposon end sequence. In some embodiments, the second polynucleotide is hybridized to the immobilized first polynucleotide before the transposase holoenzyme is added. In some embodiments, the second polynucleotide and the transposase holoenzyme are provided together. FIG. 5a shows one embodiment of this method for assembling the surface bound transposome complexes. In one method, transposase holoenzyme is added along with the non-transferred strand of the ME adaptor to a flowcell containing oligonucleotides comprising from the 5' surface grafted end: a cluster amplification primer (A.pr) and sequencing primer (S.pr) and the ME sequence (FIG. 5a). Alternatively, the non-transferred ME' strand can hybridized to the surface grafted ME strand first and then the transposase added to the flowcell.

In some embodiments, the transposome complexes are assembled in solution and immobilizing comprises a further step of ligating the first polynucleotide to an immobilized oligonucleotide coupled to the solid support. This embodiment is illustrated in FIG. 5b. In some embodiments, a splint oligonucleotide can be extended using a polymerase before a ligating step occurs.

In some embodiments, transposome dimer is assembled by hybridizing a looped oligonucleotide to an immobilized first polynucleotide. For example, a looped oligonucleotide can comprise a first end and a second end, with the first end being complementary to the transposon end sequence of the first polynucleotide. The second end of the looped oligonucleotide can be complementary to a second transposon end sequence. The second transposon end sequence can be, for example, part of a solution-phase first polynucleotide. In some embodiments, the immobilized first polynucleotide and the solution-phase first polynucleotide can comprise dissimilar transposon end sequences or complements thereof. In some such embodiments, the looped oligonucleotide comprises sequences complementary to each of the dissimilar transposon end sequences at the first and second ends. An illustration of this embodiment is shown in FIG. 5c. As shown in FIG. 5c, a contiguous adaptor pair is generated by hybridizing two oligonucleotides to the surface bound oligonucleotide. This can be achieved by employing two dissimilar transposon end sequences (ME1 and ME2). Addition of transposase holoenzyme reconstitutes an active 'looped' transposome complex, where only one of the two adaptors of each transposome is coupled to the surface FIG. 5c.

Figure 5D:
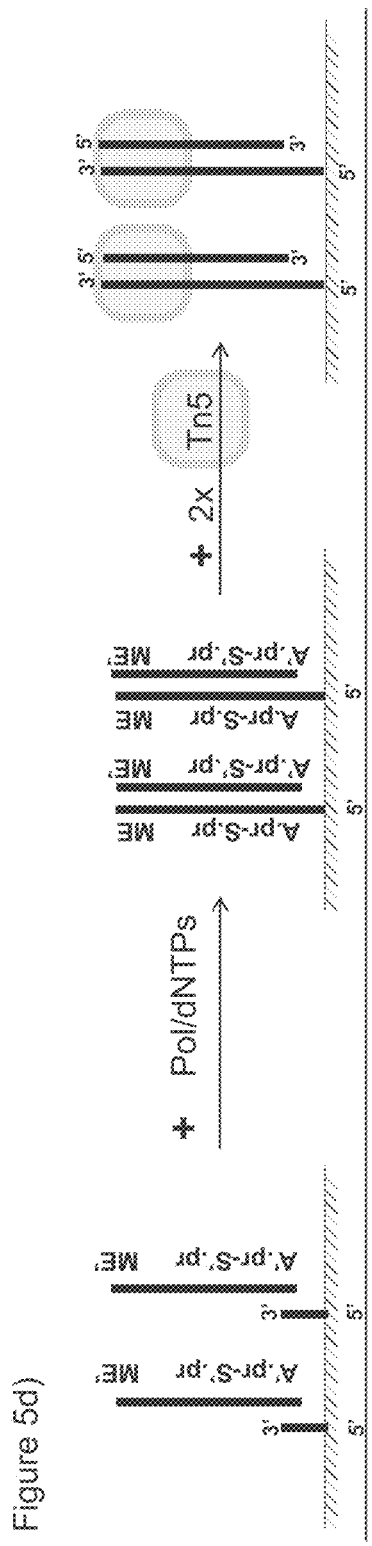

In another embodiment, transposome complexes can be assembled on a standard paired end flow cell with amplification primers immobilized thereto (e.g. a Hi Seq flow cell or MiSeq flow cell sold by Illumina Inc, San Diego, Calif.). This can be accomplished by, for example, hybridization of a 'splint' oligonucleotide that anneals to one or both species of surface grafted amplification primer. The splint acts as a template to then extend the grafted surface primer with a polymerase and dNTPs to form an oligonucleotide duplex that contains a surface amplification primer, a sequencing primer and the transposon end sequences of the transposase. Addition of transposase assembles a transposome of the surface. This embodiment is illustrated in FIG. 5d.

Figure 11:
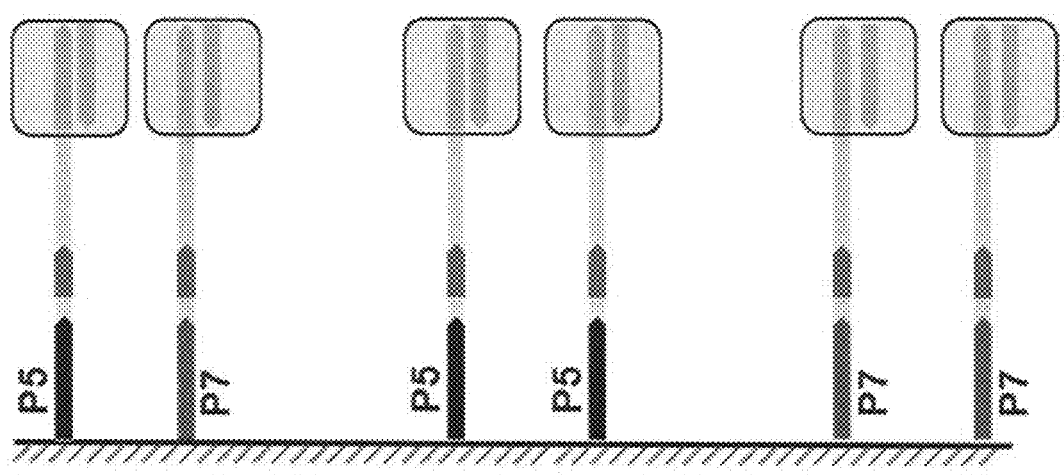
FIG. 11 is an illustration of assembly of bead-bound transposomes and subsequent tagmentation according to one embodiment.

In any of the embodiments provided herein, transposome complexes may be homodimers, or heterodimers. For example, as illustrated in FIG. 11, a homodimeric transposome would comprise two P5-ME adaptors at both sites or alternatively, two P7-ME adaptors. Similarly, a heterodimeric transposome complex would comprise both P5-ME and P7-ME adaptors, as shown in FIG. 11.

Tagmentation Using Transposome Beads

One embodiment presented herein is a population of microparticles having transposome complexes immobilized thereto. The use of a solid support such as beads can provide several advantages over solution-based tagmentation. For example, in standard solution-based tagmentation, it is difficult to control the final fragment size of the tagmentation reaction. Fragment size is a function of the ratio of transposomes to the amount and size of DNA and to the duration of the reaction. Even if these parameters are controlled, size selection fractionation is commonly required as an additional step to remove excess small fragments shorter than the combined paired-read lengths. The methods provided herein avoid those disadvantages. Specifically, bead-immobilized transposomes allow for selection of final fragment size as a function of the spatial separation of the bound transposomes, independent of the quantity of transposome beads added to the tagmentation reaction. An additional limitation of solution-based tagmentation is that it is typically necessary to do some form of purification of the products of the tagmentation reaction both before and after PCR amplification. This typically necessitates some transfer of reactions from tube to tube. In contrast, tagmentation products on the bead based transposomes can be washed and later released for amplification or other downstream processing, thus avoiding the need for sample transfer. For example, in embodiments where transposomes are assembled on paramagnetic beads, purification of the tagmentation reaction products can easily be achieved by immobilizing the beads with a magnets and washing. Thus, in some embodiments, tagmentation and other downstream processing such as PCR amplification can all be performed in a single tube, vessel, droplet or other container. In some embodiments, tagmentation and downstream processing of samples takes place on a microfluidic droplet based device, as exemplified in the disclosure of U.S. application Ser. No. 13/670,318, filed on Nov. 6, 2012 entitled "INTEGRATED SEQUENCING APPARATUSES AND METHODS OF USE" which is incorporated herein by reference in its entirety. For example, in a microfluidic droplet based device, a droplet containing target nucleic acid, wash buffer or other reagents may be passed over a surface comprising immobilized transposome complexes. Likewise, a droplet comprising beads having transposomes immobilized thereon may be contacted with target nucleic acid, wash buffer or other reagents in a microfluidic droplet based device.

In some embodiments, the immobilized transposome complexes comprise a transposase bound to a first polynucleotide and a second polynucleotide; wherein the first polynucleotide is immobilized at its 5' end to the surface of the microparticle and the second polynucleotide is hybridized to the 3' end of the first polynucleotide; and wherein the first polynucleotide comprises: (i) a 3' portion comprising a transposon end sequence, and (ii) a first tag comprising a first tag domain.

Figure 9:
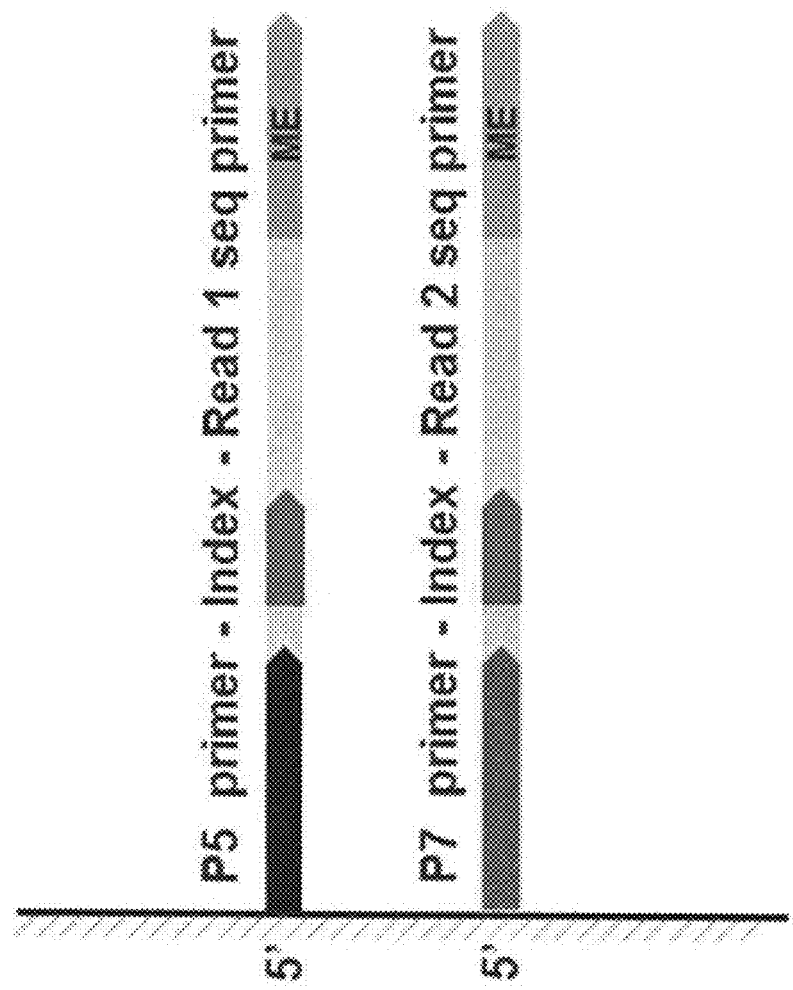
FIG. 9 is an illustration of assembly of bead-bound transposomes and subsequent tagmentation according to one embodiment.

FIGS. 9-12 provide an illustration of transposomes assembled on the surface of paramagnetic beads. FIG. 9 shows a bead surface with two different first polynucleotides immobilized thereto. The first polynucleotides that are shown comprise a transposon end sequence (ME). One of the first polynucleotides shown in comprises a tag domain comprising an amplification primer sequence (P5) and a sequencing primer sequence (Read 1). The other polynucleotide shown in FIG. 9 comprises a different amplification primer sequence (P7) and a sequencing primer sequence (Read 2). The first polynucleotides may also comprise an index tag. The index tag may be unique to the bead, or it may be shared with one or more other beads in the population. A single bead may have only a single index tag immobilized thereto, or it may have a plurality of index tags immobilized thereto.

Figure 10:
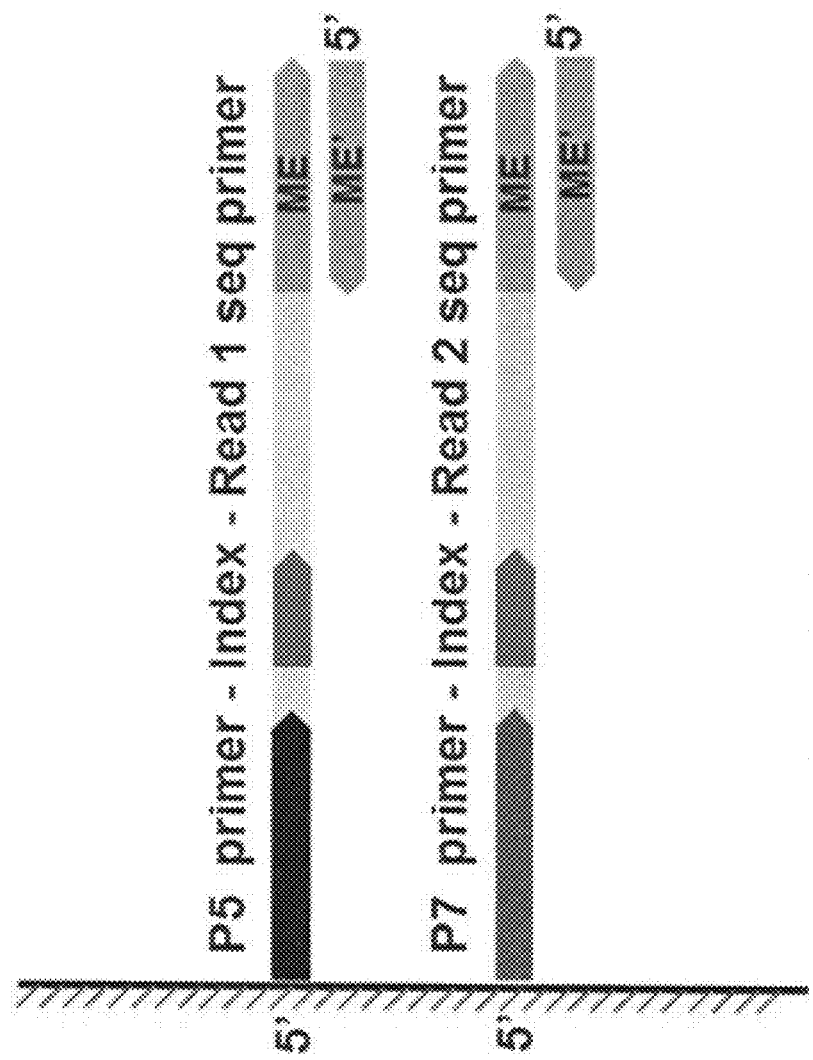
FIG. 10 is an illustration of assembly of bead-bound transposomes and subsequent tagmentation according to one embodiment.

FIG. 10 shows a second polynucleotide hybridized to each first polynucleotide. The second polynucleotide comprises a region complementary to the transposon end sequence of the first polynucleotide. In some embodiments, the second polynucleotide is 15 bp in length. In some embodiments, the second polynucleotide can be approximately 10, 11, 12, 13, 14, 15, 16, 17, 18, 19, 20 bp or more than 20 bp in length. In some embodiments, the second polynucleotide is phosphorylated at its 5' end.

FIG. 11 illustrates assembly of transposomes on the surface of the bead, where transposase enzyme is contacted with the immobilized oligonucleotides. As shown in FIG. 11, when the transposase is added to the beads, three types of transposome complexes are formed: a P5:P5, a P7:P7, and a P5:P7 complex (FIG. 11).

When the transposome beads are added to a solution of target DNA in a tagmentation buffer, tagmentation takes place, linking the DNA to the surface of the beads. An immobilized library of tagged DNA fragments is generated.

Figure 12:
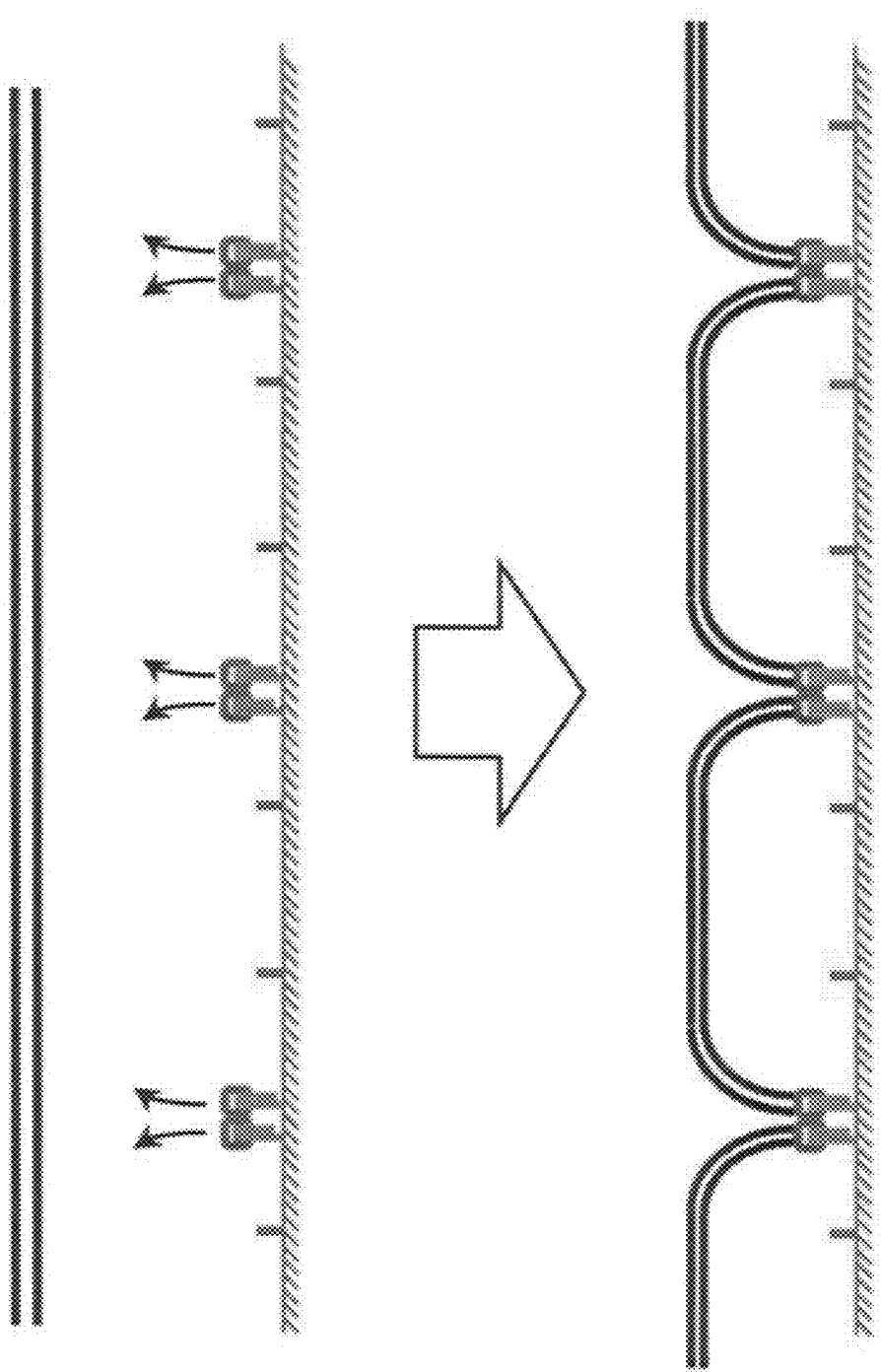
FIG. 12 is an illustration of assembly of bead-bound transposomes and subsequent tagmentation according to one embodiment.

FIG. 12 illustrates an embodiment where successive tagmentation into the DNA results in bridged molecules between transposomes. Where three types of transposomes are present (as in FIG. 11), three types of bridge complexes result: a P5:P5, P7:P7 and P5:P7 complex in a ratio of 25:25:50, respectively.

In some embodiments, the length of the bridged fragments can be dictated by the density of the transposomes on the surface of the bead. This density is tunable via the amount of oligonucleotide on the surface, the amount of duplex transposon end complexes on the surface and the amount of transposase enzyme added during the transposome assembly. Once tagmentation is complete, the P5:P7 tagmentation products can be liberated from the surface of the bead using any suitable method. In some embodiments, the tagmentation products are liberated from the beads using an amplification method such as suppression PCR, step-out PCR and the like. In some embodiments, the tagmentation products are liberated from the beads by cleavage. The cleavage can be, for example, chemical, enzymatic, photochemical or a combination thereof. It will be appreciated that any suitable method for releasing one or more tagmentation products from a solid support can be utilized in the methods provided herein.

DNA can be efficiently contacted with surface bound transposomes using any suitable method for increasing the probability of contact. For example, in some embodiments, precipitation of DNA onto the solid surface can be utilized to increase contact between the target DNA and the transposome complexes on the solid surface. Any one of a number of methods that are known in the art for contacting DNA with a solid support can be utilized, as exemplified by the disclosure of WO 2010/115122, which is incorporated by reference in its entirety. As will be appreciated by one of skill in the art, DNA can be precipitated onto a solid support by the addition of PEG, ethanol or any one of a variety of other agents known to precipitate DNA onto surfaces, including, for example, any one of a number of buffers used in solid phase reversible immobilization (SPRI) technology.

In some embodiments, a population of beads bearing immobilized transposome complexes can be mixed with an excess of beads that bear no transposomes or oligonucleotides, thereby reducing the likelihood of tagmentation across two or more different beads. Another method to reduce the likelihood of tagmentation across two or more different beads includes immobilizing beads so contact between beads is minimized. Immobilization of beads can be accomplished by any of a number of techniques known in the art, including, for example, immobilizing the beads via magnetism to the sides of a solid surface such as a microcentrifuge tube, or any other immobilization technique as exemplified by the incorporated materials of WO 2010/115122.

In some embodiments, transposome beads can be used to isolate and identify nucleic acids from a single cell, such as a prokaryotic or eukaryotic cell. For example, in some embodiments, particles such as beads are coated with indexed transposomes which share the same index (all of the transposomes present on a particular bead carry the same index, which is different from the index present on another bead). The beads can then be placed inside cells through any one of variety of methodologies known in the art. For example, methods for delivering beads inside cells include, but are not limited to gene guns, photothermal nanoblades (Wu et al. Anal Chem. (2011) 4:1321-7), and peptides used in conjunction with cell permeabilizing substances (Nitin et al Ann Biomed Eng. (2009) 37:2018-2027) and the like. It will be appreciated that any suitable method for associating DNA from a single cell with a particle bearing indexed transposomes can be used in the methods presented herein.

In some embodiments, transposomes can be covalently attached to the beads as described in detail hereinabove. Additionally or alternatively, transposomes can be released from the beads upon the application of a chemical or physical stimulus. Some examples of stimuli which can trigger release of transposome from a solid support include light and/or temperature changes. In some embodiments, the transposomes are released from the solid support using the activity of an enzyme such as a restriction endonuclease. In certain embodiments, the transposomes can be detached from the beads and move freely inside the cell. Once the beads (or alternatively, the released transposomes) come into contact with chromatin or DNA, tagmentation can take place. It will be understood that in eukaryotic and prokaryotic systems, not all genomic DNA will always be accessible and/or available for tagmentation. In some embodiments, up to 0.001%, 0.01%, 0.1%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95% or 99% or more that 99% of the total DNA in a cell is tagmented by the transposomes. The use of uniquely tagged beads makes it possible to identify reads from the same cell by grouping together reads that share the same indices. These reads can be considered as derived from the same bead (and therefore from the same cell). Additionally or alternatively, in some embodiments, a cross-linking step can be performed to cross-link cellular DNA while it is still inside the cell's nucleus. Such a step ensures that the DNA from a single cell is held together. After extracting the DNA from cells, it can then mixed with the indexed beads and subjected to tagmentation as described in detail hereinabove. Additionally or alternatively, variations of the method include the tagmentation of flow sorted chromosomes. Flow sorted chromosomes can be mixed with the indexed beads described above. A particular chromosome would adhere to one bead and the fragments generated through tagmentation would contain the same index. This could enable phasing of SNPs from whole chromosomes (haplotyping).

In some such embodiments, the total number of indices is greater than the total number of cells that are successfully tagmented. In some embodiments, a dual index approach can be implemented, for example, as a way to increase the number of possible combinations of indices. As one example, the use of two 8 base indices would give a theoretical number of combinations of $4^8 \times 4^8 = 4.3 \times 10^9$.

In some embodiments, an approach can be used to ensure that an individual cell is not tagmented by multiple beads. For example, one approach is to use beads of a size which is similar to that of the cell. This would ensure that a cell would not be able to accommodate multiple beads. Additionally or alternatively, another approach is to make use of a cell to bead ratio which favors single cell targeting. For example, if there are far more cells than beads, then the poison distribution of beads inside the cells means that the cells that have taken up a single bead far outnumber the cells that have taken up two or more beads.

In some embodiments, the single cell approach described above can be used to determine whether two SNPs (or structural rearrangements) are present in the same cell. For example, in the case of heterogeneous populations of cancer cells, knowing whether two SNPs are present in the same cell or in different cells could aid in implementing the right cancer therapy.

In some embodiments, the single cell approach described above can be used to study RNA. For example, by coating the beads with suitable enzymes (i.e. reverse transcriptase) and oligonucleotides for a reverse transcription step, gene expression at the single cell level can be analyzed. In one embodiment, after introducing the beads coated with reverse transcriptase, oligonucleotides and transposomes, the cytoplasmic RNA can be converted into cDNA, tagged and prepared inside the cells.

Methods of Assembling Long Reads Using Barcodes on Immobilized Transposomes

Barcode-assisted assembly of DNA fragments enables isolation of individual long DNA molecules within a population of DNA molecules and conversion of each molecule into a uniquely barcoded sub-fragment library. When the entire population of sub-fragmented DNA molecules is sequenced, the subfragments can be assembled back into their original long molecule by reference to the barcodes they contain.

Various methods of barcoding individual DNA molecules are known. For example, the 'dilution method,' isolates individual long molecules by extreme dilution and aliquoting into separate compartments (e.g., wells of a plate); such that each well contains only one or just a few molecules of DNA. Because each well is physically separate, a library preparation can be done in each well with a unique barcode. Thereafter the contents of the wells are pooled and sequenced. Another method employs an emulsion wherein each droplet contains long DNA molecules, library preparation reagents and a barcode unique to each droplet. Another approach uses a large library of indexed looped transposome complexes to insert multiple twin barcodes along the length of the DNA while preserving the intactness of the molecule. Subsequent cleavage between the barcode 'twins' yields fragments that can be sequenced and reassembled by matching up the twin barcodes. Each of the above-mentioned barcoding methods carries with it disadvantages that are overcome by the barcoding methods presented herein.

Presented herein are alternative methods to the above described ways of isolating and barcoding individual long molecules. The methods presented herein achieve advantages of physical isolation similar to the emulsion method without using emulsions, and at the same time provide a complexity that is much greater than that provided by the large number of 'wells' used in the dilution method. The unique barcodes of the present methods are in some ways analogous to the 'wells' of the dilution method except that the number of beads in the bead-based method can often be much higher than the number of wells in the dilution method. An additional advantage over the emulsion methods is that in the bead-based method, the barcodes are deterministically distributed (i.e., one barcode per bead) and not random (i.e. Poisson distributed). The methods presented herein also achieve the same initial preservation of molecule intactness and contiguity but without the need for looped transposome complexes as used in some other methods. Additionally, the methods presented herein do not require as large a code space as used in some other methods.

Accordingly, in some embodiments presented herein, barcoding method comprise providing a population of microparticles having transposome complexes immobilized thereto, the transposome complexes comprising a transposase bound to a first polynucleotide and second polynucleotide. In some embodiments, the first polynucleotide comprises an index domain associated with the microparticle. In some embodiments, the index domain can be unique to the microparticle. In some embodiments, the population of microparticles comprises at least a plurality of index domains. In some embodiments, the index domain is present on more than one microparticle in the population of microparticles. In some embodiments, a microparticle in the population of microparticles comprises more than one index domain.

The barcoding methods presented herein further comprise applying a target DNA to the population of microparticles, thereby generating immobilized DNA fragments that are tagged with the index domain. DNA can be efficiently contacted with surface bound transposomes using any suitable method for increasing the probability of contact as discussed hereinabove, as exemplified by the incorporated materials of WO 2010/115122.

The methods can be performed using any one of a variety of known formats, for example, with a combination of tagmentation reagents and a bead array for the library preparation, followed by an indexed sequencing run and bespoke data analysis. Any other suitable method that maintains beads in static separation from one another can be used for surface tagmentation and indexing of samples. For example, physical configurations such as wells or small depressions in the substrate that can retain the beads, such that a microsphere can rest in the well, or the use of other forces (magnetic or compressive), or chemically altered or active sites, such as chemically functionalized sites, electrostatically altered sites, hydrophobically and/or hydrophilically functionalized sites, or spots of adhesive.

In some embodiments, the microspheres are non-covalently associated in the wells, although the wells may additionally be chemically functionalized as is generally described below, cross-linking agents may be used, or a physical barrier may be used, e.g., a film or membrane over the beads.

In certain embodiments, the surface of the substrate is modified to contain chemically modified sites that can be used to attach, either covalently or non-covalently, the microspheres of the invention to the discrete sites or locations on the substrate. "Chemically modified sites" in this context includes, but is not limited to, the addition of a pattern of chemical functional groups including amino groups, carboxy groups, oxo groups and thiol groups, that can be used to covalently attach microspheres, which generally also contain corresponding reactive functional groups; the addition of a pattern of adhesive that can be used to bind the microspheres (either by prior chemical functionalization for the addition of the adhesive or direct addition of the adhesive); the addition of a pattern of charged groups (similar to the chemical functionalities) for the electrostatic attachment of the microspheres, e.g., when the microspheres comprise charged groups opposite to the sites; the addition of a pattern of chemical functional groups that renders the sites differentially hydrophobic or hydrophilic, such that the addition of similarly hydrophobic or hydrophilic microspheres under suitable experimental conditions will result in association of the microspheres to the sites on the basis of hydroaffinity. For example, the use of hydrophobic sites with hydrophobic beads, in an aqueous system, drives the association of the beads preferentially onto the sites. As outlined above, "pattern" in this sense includes the use of a uniform treatment of the surface to allow attachment of the beads at discrete sites, as well as treatment of the surface resulting in discrete sites. As will be appreciated by those in the art, this may be accomplished in a variety of ways.

In certain embodiments, a multitude of beads comprising surface bound transposomes are generated, wherein each bead contains many transposomes but all transposomes on any given bead all contain the same barcode. The generation of a population of monoclonal barcoded transposome oligonucleotides on beads can be performed according to any one of a number of techniques as is known in the art, as exemplified by the disclosure of U.S. Pat. No. 5,604,097, which is incorporated by reference in its entirety.

Figure 13:
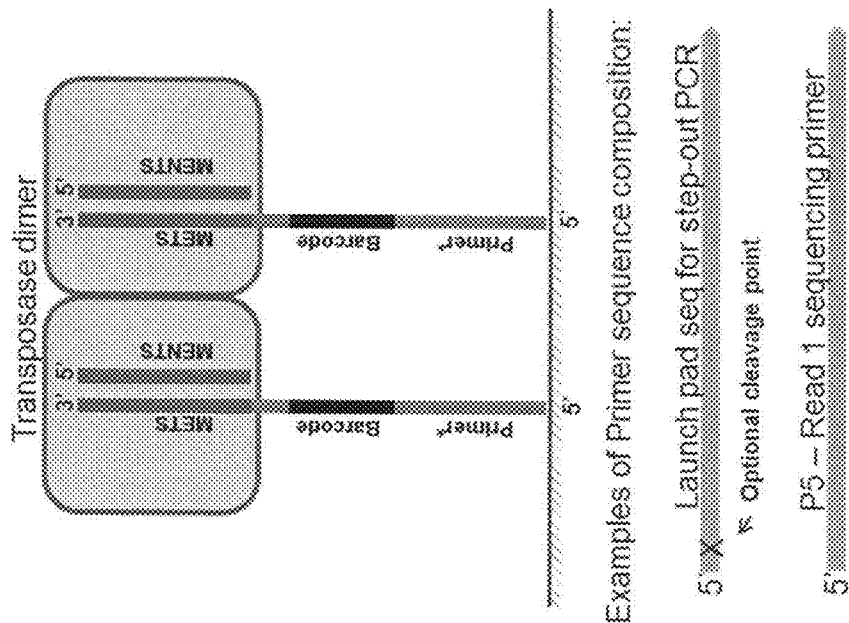
FIG. 13 is an illustration of surface bound transposomes according to one embodiment.

FIG. 13 illustrates one embodiment, where a surface bound transposome contains long oligonucleotides attached to the surface via their 5' end. As set forth in FIG. 13, the 3' end of the oligonucleotide comprises the Mosaic End (MFTS) sequences of the Tn5 transposase enzyme. Upstream of this sequence (closer to the 5' end) is a barcode sequence of typically 6-8 bases in length. Further upstream is a primer sequence. Additionally, the oligonucleotide can further comprise a cleavage site to enable the oligonucleotide to be cleaved off the surface: its presence in the oligonucleotide is optional to the overall method. A second short oligonucleotide (the non-transferred strand, MENTS) is hybridized to the METS sequence at the 3' end of the long surface grafted oligonucleotide. Finally, a transposase dimer is assembled at the 3' end of the oligonucleotides to form a functional transposome.

Figure 14:
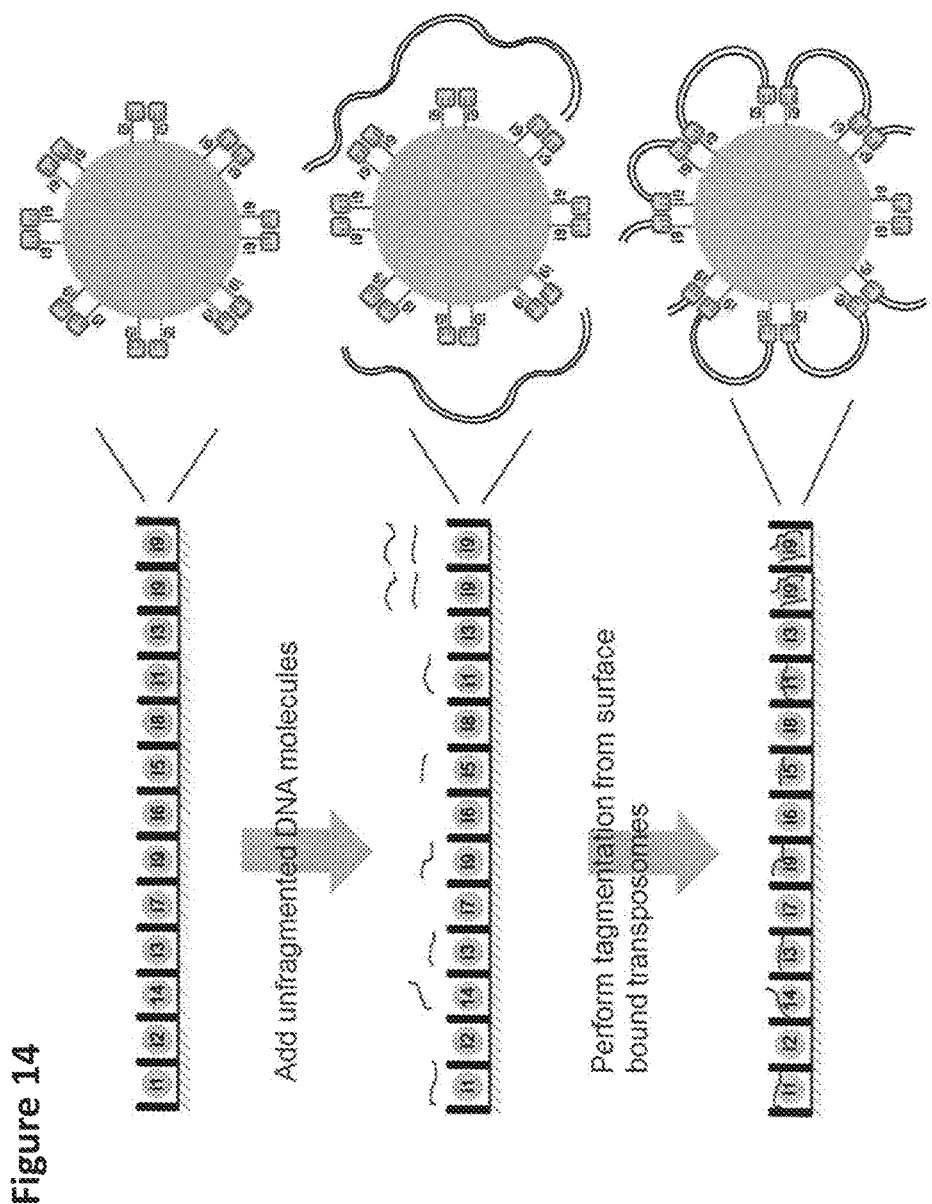
FIG. 14 is an illustration of tagmentation performed on bead-bound transposomes according to one embodiment.

FIG. 14 illustrates barcoding on beads in an array of wells. As shown in FIG. 14, when long molecules of dsDNA are added to an array of bead-immobilized transposomes, a given molecule encounters a bead and gets tagmented many times by the transposomes on the bead. Each fragment becomes immobilized to the bead and tagged with the barcode associated with that bead. In the particular embodiment shown in FIG. 14, the physical separation of beads in the array chip prevents a DNA molecule from reaching between two beads. In other embodiments, the beads are in close contact and one or more DNA molecules may stretch between two or more beads. In some embodiments, more than one DNA molecule can be tagmented per bead. The probability of two alleles being tagmented onto the same bead is low and is a function of the concentration of the DNA added, the number of beads and the number of barcodes. For example, to avoid two alleles occurring in the same well, 0.1× haplome equivalents (50,000 genomes equivalents) would need to be loaded to 1 million beads each with a unique barcode.

Figure 15:
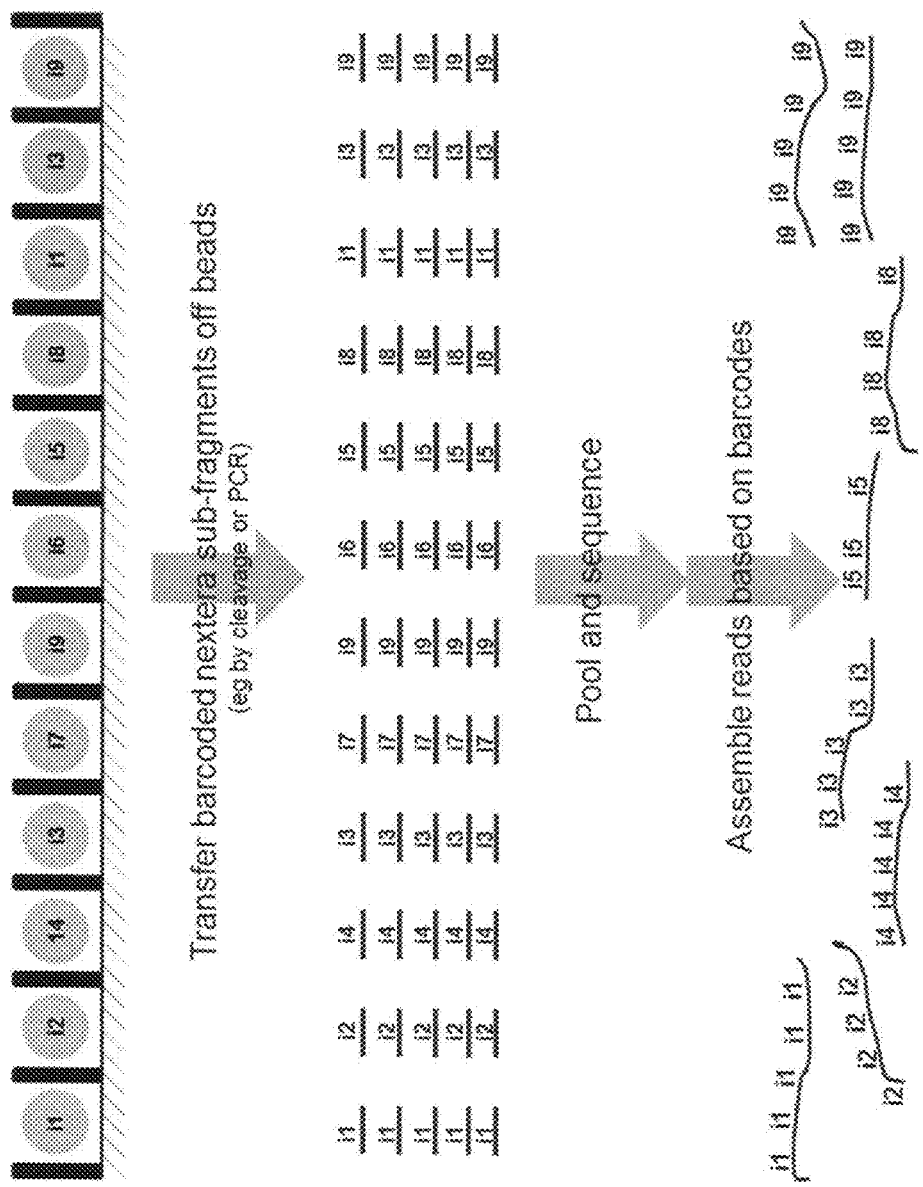
FIG. 15 is an illustration of tagmentation and barcoding of sub-fragments performed on bead-bound transposomes according to one embodiment.

FIG. 15 illustrates transfer of barcoded tagged molecules to a sequencing reaction. As shown in FIG. 15, once the tagmentation is complete the DNA is transferred from the bead surface to solution so that individual fragments can be pooled and prepared for sequencing. Sequencing and assembly by reference to the barcodes enables the sequence of the original long tagmented DNA molecules to be re-created, thus enabling long or pseudo-long reads and phasing of SNPs.

Release of the barcoded surface tagmented fragments to the solutions can be achieved using any suitable methodology as is known in the art. For example, in some embodiments, the tagmented molecules can be cleaved off the surface of the beads via a cleavage moiety present at the 5' end of the surface bound oligonucleotides (see FIG. 13). The cleavage moiety can be any moiety suitable for cleavage of a nucleic acid strand from a solid support. Examples of methods that utilize a cleavage moiety include, but are not limited to, restriction endonuclease cleavage, chemical cleavage, RNase cleavage, photochemical cleavage, and the like, including those cleavage methods and cleavage moieties set forth in WO 2006/064199, which is incorporated by reference in its entirety.

Cleavage using a cleavage moiety yields a molecule having the following format:

5'-Primer-Barcode-ME-Insert-ME-Barcode-Primer-3'

The "Primer" regions can be used as hybridization points to hybridize PCR step-out primers that enable additional sequences to be added such as amplification and sequencing primers. For example, amplification primers P5 and P7 can be added. Once added, suppression PCR can be used, for example, to enrich for molecules that have P5 adaptors on one end and P7 on the other.

In some embodiments, amplification can be performed directly off the beads with step-out primers that add P5 and P7 adaptor sequences by suppression PCR. In another embodiment, each bead can have two types of surface grafted oligonucleotides where the primer sequence (as in FIG. 13) is either P5-Read1 sequencing primer or P7-Read 2 sequencing primer. This will result in mixed P5-P7 transposomes. These can either be cleaved off the beads and followed by suppression PCR to enrich the P5/P7 molecules or amplified directly off the beads, as described above.

Figure 16:
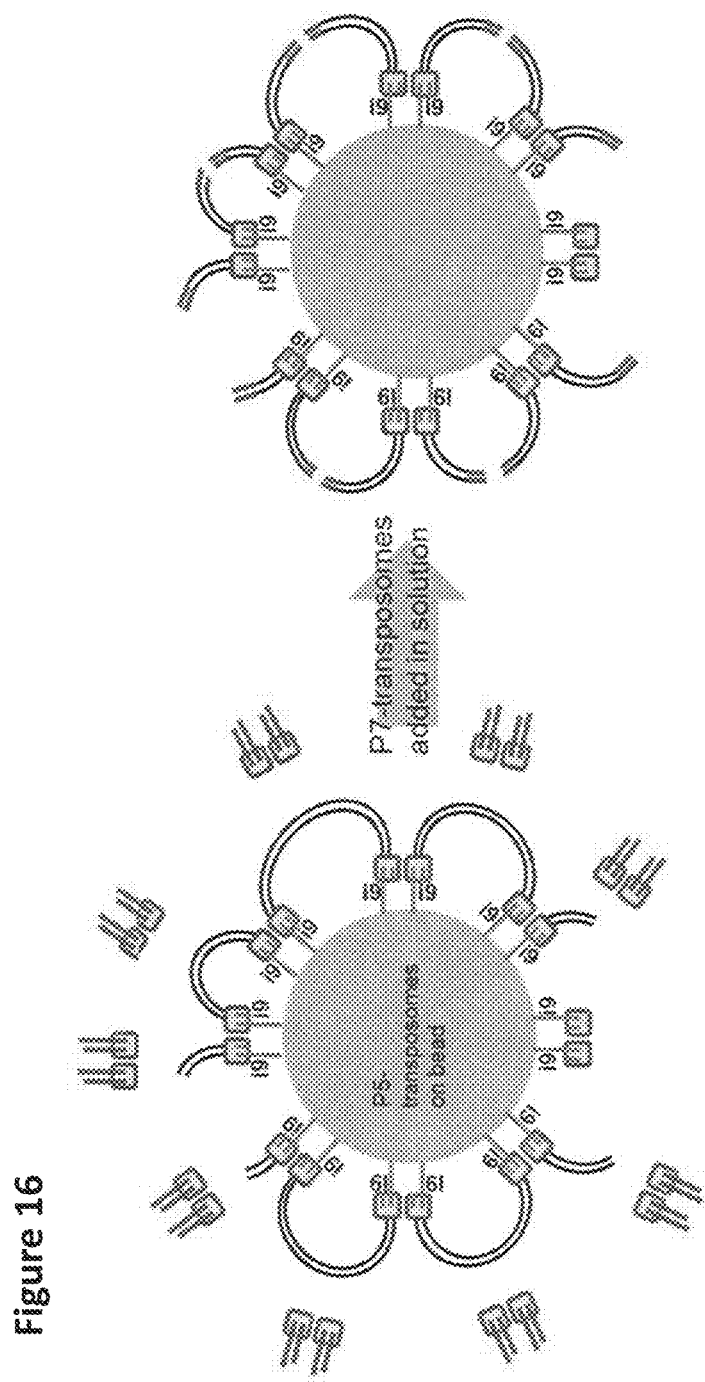
FIG. 16 is an illustration of tagmentation and barcoding of sub-fragments performed on bead-bound transposomes according to one embodiment.

In some embodiments, a single transposome type (e.g. P5-Read 1-barcode) may be present on the surface of the bead. Once surface tagmentation is complete, a second transposome bearing a different amplification and/or sequencing primer can be added in solution to cleave the bridged molecules. This yields all molecules with the same adaptor format that can either be cleaved or amplified off the bead surface. An additional sample-specific barcode could be added to the solution transposome such that multiple samples can be pooled by the method. FIG. 16 is an illustration of this embodiment. As shown in FIG. 16, solution-phase transposomes bearing a P7 amplification primer sequence are added to a bead with immobilized bridged tagmentation products. The immobilized fragments are tagged with a polynucleotide sequence comprising a P5 amplification primer sequence and an barcode index tag (i9) that is unique to the bead. As shown in FIG. 16, after the second tagmentation reaction, each fragment has a free end bearing a P7 primer sequence and an immobilized end bearing a P5 primer sequence.

Example 1

Surface Tagmentation on a Flowcell

This example describes an experiment confirming the embodiment illustrated in FIGS. 4a and 4b (surface tagmentation followed by solution tagmentation).

An experiment on an 8 lane flowcell was carried out using a list of conditions and controls as shown in FIGS. 6a and 6b. Lane 6 indicates the complete end to end exposition of the method: unfragmented E. coli genomic DNA was added to a flowcell where upon it was tagmented by the surface bound transposomes. Next heat was applied to the flowcell to selectively dehybridize the naked ME sequences thus abolishing them as a target for a second tagmentation reaction when transposome was next added from solution. Following the second tagmentation reaction, clusters were generated and 'paired-end' sequenced (2×36 base reads) was performed. Sequencing metrics are given in slide 7 which show that in lane 6, 73.14% of clusters passed filters and 74.69 of these aligned. This provides enough data to yield a gap size plot of the inserts and an estimation of library diversity (see FIG. 8).

Other lanes included controls which are listed below:

Lane 1 comprises PhiX DNA as a positive control to ensure everything has been pumping correctly and cluster generation and sequencing works as expected.

Lane 2 is another control lane and illustrates tagmentation into surface bound transposons in the absence of target DNA. The flowcell (FC) comprises a standard paired end FC onto which an oligonucleotide containing the tagmentation primer sequence and ME' sequence (non-transferred ME' strand) was hybridized to the P7 surface oligonucleotide. This oligonucleotide was added at a saturating concentration. First extension resulted in a double stranded transposon with ME ends. A P5 transposome was assembled in solution and flowed onto the FC (6.25 nM/lane). The P5 transposome tagments the double stranded surface bound transposons. The tagmentation products are subsequently converted into clusters.

Lane 3 illustrates tagmentation into surface bound transposons in the absence of target DNA, only in this instance the FC has been heated to 75° C. in order to convert the ds surface bound transposons into single stranded oligonucleotides prior to the addition of the P5 Transposome from solution in order to prevent tagmentation into these constructs, as this was interfering with the tagmentation of the target DNA.

Lane 4 illustrates the addition of a surface bound transposome to the lane 3 conditions. In this lane an oligonucleotide containing the tagmentation primer sequence and ME' sequence was hybridized to the P7 surface oligonucleotide. First extension results in a double stranded transposon with ME ends. Following this a P7 transposome was assembled on the surface of the FC by adding Tn5 enzyme to the lane at 50× concentration and incubating at 30° C. for 30 minutes. The FC was then heated to 75° C. prior to adding P5 Transposome from solution.

Lane 5 comprises the same conditions as lane 4, only in this case instead of adding P5 Transposome from solution, an E. coli 900 bp library (with P5/P7 ends) was added to determine whether the P7 surface bound transposome remains active after the heating step.

Lane 6 illustrates an example of the invention put into practice. In this instance the FC comprises of a standard paired end FC onto which an oligonucleotide containing the tagmentation primer sequence and ME' sequence was hybridized to the P7 surface oligonucleotide. First extension results in double stranded transposons with ME ends. P7 transposomes are assembled on the surface of the FC by adding Tn5 enzyme to the lane at 50× concentration and incubating at 30° C. for 30 minutes. Target DNA (300 ng of unfragmented E. coli genomic DNA) was added onto the FC lane and an incubation step of 15 min at 55° C. was carried out in order for tagmentation to take place. The P7 surface bound transposome was washed off using PBI (Qiagen) and the FC was then heated to 75° C. prior to adding P5 transposome from solution. Following addition of P5 transposome from solution and an incubation step of 15 min at 55° C., a stand displacement extension reaction was carried out in order to fill in the 9-bp gaps generated in the DNA backbone by the transposition reaction. The stand displacement extension reaction comprises of the addition of a Bst and dNTP mix and incubation at 65° C. for 5 min. The P5 transposome was washed off in the final step. At this point all surface bound molecules should be P5-P7 templates and can therefore be converted into clusters.

Lane 7 comprises of the same conditions as lane 6, only in this instance the heat step has been left out in order to highlight the effect of heat on the cluster number and % align.

Lane 8 comprises a negative control where the P7 transposome has been assembled on the surface at 50× concentration in the presence of a saturating concentration of ds surface bound transposons, however, no target DNA has been added. This allows an assessment of whether the surface bound P7 transposome tagments into its neighboring ds surface bound transposons.

Example 2

Surface Bound Sample Preparation from an E. coli Scrape

An E. coli sample (5 mm by 2 mm scrape from a lawn on an agar plate) was scraped and resuspended in a tube containing water and glass beads. The suspended cells and beads were mixed using a vortex mixer to break open the cells and then centrifuged to pellet cellular debris. The supernatant (containing the cell lysate, including proteins and nucleic acids) was removed and added to a Genome Analyzer flowcell (Illumina, Inc., San Diego, Calif.) having immobilized transposomes according to the protocol described in Example 1.

Cluster generation was performed on the flowcell using a Cluster Station sample preparation device (Illumina, Inc., San Diego, Calif.). After cluster generation, a paired-end sequencing run was performed with reads of 36 bases in each direction.

For Read 1, 58.99% of clusters passed filters and 92.16 of these aligned. For Read 2, 58.99% of clusters passed filters and 55.08 of these aligned. These data confirm that unpurified cell lysates can be added directly to a flowcell having immobilized transposomes with surprisingly robust sequencing results.

Example 3

This example describes methods to avoid tagmentation of surface-bound oligonucleotide duplexes when solution phase transposomes are added to a flowcell.

One method for assembling transposomes on the surface of a flow cell is to take a standard paired end flow cell, hybridize a 'splint' oligonucleotide against the P5 and/or P7 surface grafted oligonucleotides forming an extendable overhang that can be extended with a polymerase to make a duplex containing a double stranded ME sequence. At this stage transposase enzyme can be added to form a functional surface bound transposome (FIG. 5d). If only a portion of the duplexes form a transposome, remaining 'naked' ME duplexes may subsequently become targets for tagmentation by either nearby surface-bound transposomes or transposomes added from solution. Furthermore, fully assembled surface transposomes contain dsDNA portions upstream of the ME sequences that can also become targets for tagmentation by nearby surface-bound transposomes or transposomes added from solution. This undesired tagmentation manifests itself in a reduction of the percentage of clusters passing purity filters that align to the target genome.

An example of this effect can be seen by comparing lanes 4 and 5 versus lanes 6 and 7 in FIG. 18b. In lanes 6 and 7 transposomes were assembled as described above with the long splint oligonucleotides that, after extension and transposome assembly, produced surface bound duplexes that have at least 50 double stranded bases. Upon use in a surface tagmentation reaction (FIG. 18a) and subsequent sequencing, only 22.59 and 15.52% of clusters aligned to the target E. coli respectively (FIG. 18b).

Figure 17:
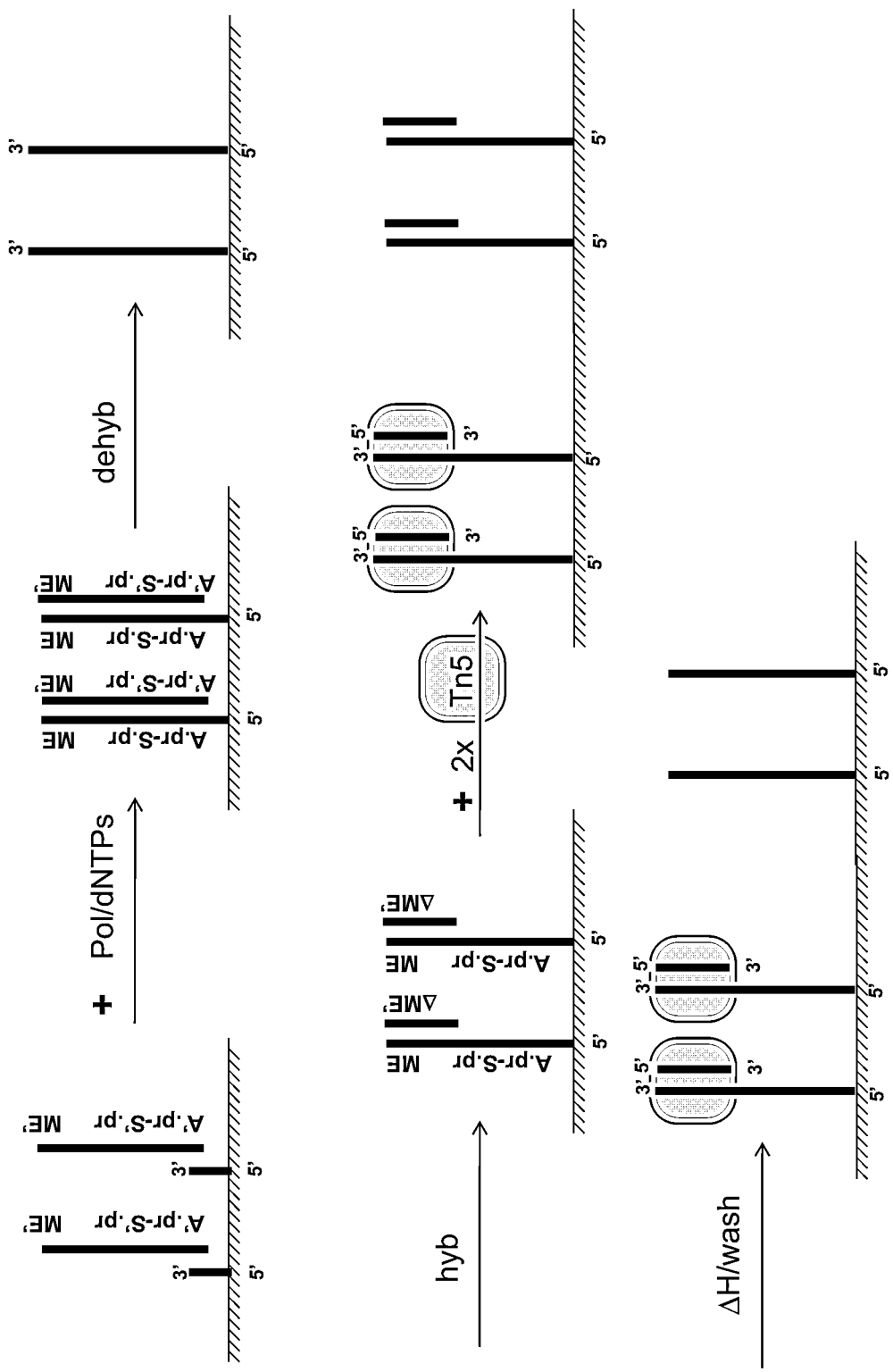
FIG. 17 is an illustration of transposome assembly as described in Example 3.

To avoid producing a population of clusters that contain sequences that do not align to the target genomic DNA, transposome assembly was done as indicated in FIG. 17. A 'splint' oligonucleotide was first hybridized against the P5 and/or P7 surface grafted oligonucleotides forming an extendable overhang that could be extended with a polymerase to make a duplex containing a double stranded ME sequence. Next, the splint oligonucleotide was removed by de-annealing and washing away, and then was replaced by hybridizing a shorter oligonucleotide as little as 12 bases long but preferably 16 bases long to the 3' end of the surface attached ME oligonucleotide. Transposase was added to assemble a transposome that did not contain any exposed dsDNA. Any 'naked' duplexes that did not contain a bound transposase were removed by incubating the flow cell at 60° C. and washing under flow conditions to selectively de-anneal and remove the short duplex DNA.

The beneficial effect of this approach to assembling transposomes can be seen in Lanes 4 and 5 where the surface bound transposomes were assembled by this method and used in a surface tagmentation reaction (FIG. 18a). The percentage of clusters that aligned to E. coli increases from 22.59 and 15.52% for lane 6 and 7 respectively, to 96.47 and 96.41 for lanes 4 and 5 respectively (FIG. 18b).

Throughout this application various publications, patents and/or patent applications have been referenced. The disclosure of these publications in their entireties is hereby incorporated by reference in this application.

The term comprising is intended herein to be open-ended, including not only the recited elements, but further encompassing any additional elements.

A number of embodiments have been described. Nevertheless, it will be understood that various modifications may be made. Accordingly, other embodiments are within the scope of the following claims.

What is claimed is:

1. A method of generating a solid support, the method comprising immobilizing a plurality of transposome complexes to the solid support, said transposome complexes comprising a transposase bound to a first polynucleotide and a second polynucleotide, said first polynucleotide comprising:
   i. a 3' portion comprising a transposon end sequence, and
   ii. a first tag comprising a first tag domain;
   wherein said second polynucleotide comprises a complementary transposon end sequence;
   wherein said transposome complexes are assembled in solution; and wherein said immobilizing comprises (1) providing the transposase, the first polynucleotide, the second polynucleotide, and ligase in solution, and (2) ligating said first polynucleotide to an immobilized polynucleotide coupled to said solid support,
   wherein said immobilized polynucleotide is hybridized to a splint oligonucleotide.

2. The method of claim 1, wherein the splint oligonucleotide is extended using a polymerase before the ligating.

3. The method of claim 1, wherein transposase holoenzyme is contacted with said solid support after said first polynucleotide is ligated to said immobilized polynucleotide.

4. The method of claim 1, wherein transposase holoenzyme and said second polynucleotide are contacted with said solid support concurrently.

5. The method of claim 1, wherein said tag domain comprises a region for cluster amplification and/or a region for priming a sequencing reaction.

6. The method of claim 1, wherein said transposome complex comprises a hyperactive Tn5 transposase.

7. The method of claim 1, wherein the solid support comprises microparticles.

8. The method of claim 1, wherein the solid support comprises a patterned surface or comprises wells.

9. The method of claim 1, wherein the transposome complexes are present on the solid support at a density of at least $10^3$, $10^4$, $10^5$, or $10^6$ complexes per $mm^2$.

10. The method of claim 1, wherein the transposome complexes comprise homodimers, the homodimers comprising a first plurality of homodimers and a second plurality of homodimers, wherein the first polynucleotide of the first plurality of homodimers comprises a first sequence and the first polynucleotide of the second plurality of homodimers comprises a second sequence different than the first sequence.

11. The method of claim 10, wherein the transposome complexes further comprise a plurality of heterodimers, wherein each heterodimer comprised in the plurality of heterodimers comprises a first polynucleotide comprising the first sequence and a first polynucleotide comprising the second sequence.

* * * * *